US012667486B2

(12) United States Patent　　　(10) Patent No.:　US 12,667,486 B2

Heitzmann et al.　　　　　　　　　(45) Date of Patent:　　Jun. 30, 2026

(54) BIORESORBABLE OCULAR DRUG DELIVERY DEVICE

(71) Applicant: Glaukos Corporation, Aliso Viejo, CA (US)

(72) Inventors: Harold Alexander Heitzmann, Irvine, CA (US); David Steven Haffner, Mission Viejo, CA (US); Kenneth Martin Curry, Oceanside, CA (US); Thomas W. Burns, Dana Point, CA (US)

(73) Assignee: Glaukos Corporation, Aliso Viejo, CA (US)

( * ) Notice: Subject to any disclaimer, the term of this patent is extended or adjusted under 35 U.S.C. 154(b) by 1087 days.

(21) Appl. No.: 17/660,306

(22) Filed: Apr. 22, 2022

(65) Prior Publication Data

US 2022/0313486 A1　　Oct. 6, 2022

Related U.S. Application Data

(63) Continuation of application No. 16/095,680, filed as application No. PCT/US2017/028665 on Apr. 20, 2017, now Pat. No. 11,318,043.

(60) Provisional application No. 62/325,378, filed on Apr. 20, 2016.

(51) Int. Cl.
_A61F 9/00_　　　(2006.01)
_A61F 9/007_　　　(2006.01)

(52) U.S. Cl.
CPC ........ _A61F 9/0017_ (2013.01); _A61F 9/00781_ (2013.01); _A61F 2210/0004_ (2013.01); _A61F 2250/0068_ (2013.01)

(58) Field of Classification Search
CPC ............ A61M 9/0017; A61M 9/00781; A61M 2210/0004; A61M 2250/0068
See application file for complete search history.

(56) References Cited

U.S. PATENT DOCUMENTS

| | | | |
|---|---|---|---|
| 663,670 | A | 12/1900 | Wiswall |
| 2,031,754 | A | 2/1936 | Bacigalupi |
| 3,416,530 | A | 12/1968 | Ness |
| 3,710,795 | A | 1/1973 | Higuchi et al. |
| 3,949,750 | A | 4/1976 | Freeman |
| 3,961,628 | A | 6/1976 | Arnold |

(Continued)

FOREIGN PATENT DOCUMENTS

| | | |
|---|---|---|
| AU | 2004264913 | 12/2011 |
| AU | 2019-310003 | 2/2021 |

(Continued)

OTHER PUBLICATIONS

US 7,524,280 B2, 04/2009, Connors et al. (withdrawn)

(Continued)

_Primary Examiner_ — Philip R Wiest
(74) _Attorney, Agent, or Firm_ — Knobbe, Martens, Olson & Bear, LLP

(57) ABSTRACT

Disclosed herein are implantable intraocular drug delivery devices structured to provide targeted and/or controlled release of a drug to a desired intraocular target tissue, and methods of implanting and methods of using such devices for the treatment of ocular diseases and disorders. In certain embodiments, some, most, or essentially all of the device is made of biodegradable materials.

17 Claims, 25 Drawing Sheets

(56)                    References Cited

U.S. PATENT DOCUMENTS

| | | | |
|---|---|---|---|
| 4,034,756 A | 7/1977 | Higuchi et al. |
| 4,093,708 A | 6/1978 | Zaffaroni et al. |
| 4,113,088 A | 9/1978 | Binkhorst |
| 4,207,890 A | 6/1980 | Mamajek et al. |
| 4,328,803 A | 5/1982 | Pape |
| 4,450,150 A | 5/1984 | Sidman |
| 4,468,216 A | 8/1984 | Muto |
| 4,521,210 A | 6/1985 | Wong |
| 4,736,836 A | 4/1988 | Alongi et al. |
| 4,743,248 A | 5/1988 | Bartoo et al. |
| 4,828,439 A | 5/1989 | Giannuzi |
| 4,846,793 A | 7/1989 | Leonard et al. |
| 4,853,224 A | 8/1989 | Wong |
| 4,863,457 A | 9/1989 | Lee |
| 4,878,905 A | 11/1989 | Blass |
| 4,883,864 A | 11/1989 | Scholz |
| 4,955,881 A | 9/1990 | Eckenhoff |
| 4,997,652 A | 3/1991 | Wong |
| 5,017,381 A | 5/1991 | Maruyama et al. |
| 5,098,443 A | 3/1992 | Parel et al. |
| 5,128,145 A | 7/1992 | Edgren et al. |
| 5,164,188 A | 11/1992 | Wong |
| 5,248,231 A | 9/1993 | Denham et al. |
| 5,324,280 A | 6/1994 | Wong et al. |
| 5,364,374 A | 11/1994 | Morrison et al. |
| 5,378,474 A | 1/1995 | Morella et al. |
| 5,378,475 A | 1/1995 | Smith et al. |
| 5,380,290 A | 1/1995 | Makower et al. |
| 5,384,333 A | 1/1995 | Davis et al. |
| 5,443,505 A | 8/1995 | Wong et al. |
| 5,464,450 A | 11/1995 | Buscemi et al. |
| 5,466,233 A | 11/1995 | Weiner et al. |
| 5,500,465 A | 3/1996 | Krishnan et al. |
| 5,502,052 A | 3/1996 | DeSantis |
| 5,516,522 A | 5/1996 | Peyman et al. |
| 5,547,993 A | 8/1996 | Miki |
| 5,599,534 A | 2/1997 | Himmelstein et al. |
| 5,629,008 A | 5/1997 | Lee |
| 5,643,321 A | 7/1997 | McDevitt |
| 5,645,856 A | 7/1997 | Lacy et al. |
| 5,652,014 A | 7/1997 | Galin et al. |
| 5,652,236 A | 7/1997 | Krauss |
| 5,663,205 A | 9/1997 | Ogawa et al. |
| 5,665,114 A | 9/1997 | Weadock et al. |
| 5,670,161 A | 9/1997 | Healy et al. |
| 5,686,425 A | 11/1997 | Lee |
| 5,709,854 A | 1/1998 | Griffith-Cima et al. |
| 5,725,493 A | 3/1998 | Avery et al. |
| 5,725,529 A | 3/1998 | Nicholson et al. |
| 5,733,327 A | 3/1998 | Igaki et al. |
| 5,766,242 A | 6/1998 | Wong et al. |
| 5,767,079 A | 6/1998 | Glaser et al. |
| 5,773,019 A | 6/1998 | Ashton et al. |
| 5,814,620 A | 9/1998 | Robinson et al. |
| 5,824,072 A | 10/1998 | Wong |
| 5,869,079 A | 2/1999 | Wong et al. |
| 5,869,468 A | 2/1999 | Freeman |
| 5,891,084 A | 4/1999 | Lee |
| 5,893,837 A | 4/1999 | Eagles et al. |
| 5,902,598 A | 5/1999 | Chen et al. |
| 5,925,342 A | 7/1999 | Adorante et al. |
| 5,952,378 A | 9/1999 | Stjerschantz et al. |
| 5,980,928 A | 11/1999 | Terry |
| 5,981,598 A | 11/1999 | Tatton |
| 6,004,302 A | 12/1999 | Brierley |
| 6,007,511 A | 12/1999 | Prywes |
| 6,059,812 A | 5/2000 | Clerc et al. |
| 6,060,463 A | 5/2000 | Freeman |
| 6,063,116 A | 5/2000 | Kelleher |
| 6,063,396 A | 5/2000 | Kelleher |
| 6,110,912 A | 8/2000 | Kaufman et al. |
| 6,129,761 A | 10/2000 | Hubbell |
| 6,159,458 A | 12/2000 | Bowman et al. |
| 6,196,993 B1 * | 3/2001 | Cohan ............... A61F 9/0017 604/93.01 |
| 6,228,873 B1 | 5/2001 | Brandt et al. |
| 6,231,600 B1 | 5/2001 | Zhong |
| 6,231,853 B1 | 5/2001 | Hillman et al. |
| 6,248,363 B1 | 6/2001 | Patel et al. |
| 6,251,090 B1 | 6/2001 | Avery et al. |
| 6,268,398 B1 | 7/2001 | Ghosh et al. |
| 6,274,138 B1 | 8/2001 | Bandman et al. |
| 6,290,684 B1 | 9/2001 | Herrick |
| 6,299,895 B1 | 10/2001 | Hammang et al. |
| 6,306,120 B1 | 10/2001 | Tan |
| 6,328,758 B1 | 12/2001 | Tornier et al. |
| 6,331,313 B1 | 12/2001 | Wong et al. |
| 6,348,042 B1 | 2/2002 | Warren, Jr. |
| 6,369,116 B1 | 4/2002 | Wong et al. |
| 6,375,972 B1 | 4/2002 | Guo et al. |
| 6,378,526 B1 | 4/2002 | Bowman et al. |
| 6,397,849 B1 | 6/2002 | Bowman et al. |
| 6,413,245 B1 | 7/2002 | Yaacobi et al. |
| 6,416,777 B1 | 7/2002 | Yaacobi |
| 6,423,001 B1 | 7/2002 | Abreu |
| 6,436,427 B1 | 8/2002 | Hammang et al. |
| 6,443,893 B1 | 9/2002 | Schnakenberg et al. |
| 6,450,984 B1 | 9/2002 | Lynch et al. |
| 6,454,787 B1 | 9/2002 | Maddalo et al. |
| 6,455,062 B1 | 9/2002 | Olejnik et al. |
| 6,464,724 B1 | 10/2002 | Lynch et al. |
| 6,503,231 B1 | 1/2003 | Prausnitz et al. |
| 6,506,411 B2 | 1/2003 | Hunter et al. |
| 6,517,483 B2 | 2/2003 | Park et al. |
| 6,524,275 B1 | 2/2003 | Lynch et al. |
| 6,533,769 B2 | 3/2003 | Homen |
| 6,548,078 B2 | 4/2003 | Guo et al. |
| 6,551,618 B2 | 4/2003 | Baird et al. |
| 6,562,374 B1 | 5/2003 | Han et al. |
| 6,576,219 B2 | 6/2003 | Brandt et al. |
| 6,589,198 B1 | 7/2003 | Soltanpour et al. |
| 6,589,203 B1 | 7/2003 | Mitrev |
| 6,626,858 B2 | 9/2003 | Lynch et al. |
| 6,638,239 B1 | 10/2003 | Bergheim et al. |
| 6,649,184 B2 | 11/2003 | Hammang et al. |
| 6,656,490 B1 | 12/2003 | Steinemann et al. |
| 6,660,870 B1 | 12/2003 | Ruskinko et al. |
| 6,666,841 B2 | 12/2003 | Gharib et al. |
| 6,682,500 B2 | 1/2004 | Soltanpour et al. |
| 6,692,759 B1 | 2/2004 | Wong et al. |
| 6,693,093 B2 | 2/2004 | Chowdhary et al. |
| 6,699,493 B2 | 3/2004 | Wong |
| 6,712,764 B2 | 3/2004 | Jeffries et al. |
| 6,726,666 B2 | 4/2004 | de Juan, Jr. |
| 6,726,918 B1 | 4/2004 | Wong et al. |
| D490,152 S | 5/2004 | Myall et al. |
| 6,730,056 B1 | 5/2004 | Ghaem et al. |
| 6,736,791 B1 | 5/2004 | Tu et al. |
| 6,758,837 B2 | 7/2004 | Peclat et al. |
| 6,764,698 B1 | 7/2004 | Byun et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,939,298 B2 | 9/2005 | Brown et al. |
| 6,939,299 B1 | 9/2005 | Petersen et al. |
| 6,955,656 B2 | 10/2005 | Bergheim et al. |
| 6,981,958 B1 | 1/2006 | Gharib et al. |
| 6,998,137 B2 | 2/2006 | Shih et al. |
| 7,025,744 B2 | 4/2006 | Utterberg et al. |
| 7,033,603 B2 | 4/2006 | Nelson et al. |
| 7,048,946 B2 | 5/2006 | Wong et al. |
| 7,083,802 B2 | 8/2006 | Peyman |
| 7,094,225 B2 | 8/2006 | Tu et al. |
| 7,094,226 B2 | 8/2006 | Yaacobi |
| 7,101,567 B1 | 9/2006 | Sano et al. |
| 7,135,009 B2 | 11/2006 | Tu et al. |
| 7,163,543 B2 | 1/2007 | Smedley et al. |
| 7,182,747 B2 | 2/2007 | Kwon |
| 7,186,232 B1 | 3/2007 | Smedley et al. |
| 7,192,412 B1 | 3/2007 | Zhou et al. |
| 7,195,774 B2 | 3/2007 | Carvalho et al. |
| 7,220,238 B2 | 5/2007 | Lynch et al. |
| 7,226,435 B2 | 6/2007 | Darnell |

(56) References Cited

U.S. PATENT DOCUMENTS

| | | | |
|---|---|---|---|
| 7,252,006 | B2 | 8/2007 | Tai et al. |
| 7,261,529 | B2 | 8/2007 | Persyn et al. |
| 7,273,475 | B2 | 9/2007 | Tu et al. |
| 7,297,130 | B2 | 11/2007 | Bergheim et al. |
| 7,402,156 | B2 | 7/2008 | Kiehlbauch et al. |
| 7,431,710 | B2 | 10/2008 | Tu et al. |
| 7,445,793 | B2 | 11/2008 | Niwa et al. |
| 7,488,303 | B1 | 2/2009 | Haffner et al. |
| 7,494,487 | B2 | 2/2009 | Timm |
| 7,496,174 | B2 | 2/2009 | Gertner et al. |
| 7,513,893 | B2 | 4/2009 | Soroudi |
| RE40,722 | E | 6/2009 | Chappa |
| 7,563,241 | B2 | 7/2009 | Tu et al. |
| 7,563,255 | B2 | 7/2009 | Adamis et al. |
| 7,585,517 | B2 | 9/2009 | Cooper et al. |
| 7,592,016 | B2 | 9/2009 | Wong et al. |
| 7,638,137 | B2 | 12/2009 | Chauhan et al. |
| 7,678,065 | B2 | 3/2010 | Haffner et al. |
| 7,678,078 | B1 | 3/2010 | Peyman et al. |
| 7,680,244 | B2 | 3/2010 | Gertner et al. |
| 7,680,245 | B2 | 3/2010 | Gertner |
| 7,697,663 | B2 | 4/2010 | Gertner |
| 7,708,711 | B2 | 5/2010 | Tu et al. |
| 7,709,049 | B2 | 5/2010 | Chappa |
| 7,749,528 | B2 | 7/2010 | DeCarvalho et al. |
| 7,776,024 | B2 | 8/2010 | Santini et al. |
| 7,794,751 | B2 | 9/2010 | Chudzik et al. |
| 7,811,252 | B2 | 10/2010 | Dacquay et al. |
| 7,815,592 | B2 | 10/2010 | Coroneo |
| 7,822,175 | B2 | 10/2010 | Gertner |
| 7,846,468 | B2 | 12/2010 | Wong |
| 7,850,637 | B2 | 12/2010 | Lynch et al. |
| 7,857,782 | B2 | 12/2010 | Tu et al. |
| 7,867,186 | B2 | 1/2011 | Haffner et al. |
| 7,867,205 | B2 | 1/2011 | Bergheim et al. |
| 7,879,001 | B2 | 2/2011 | Haffner et al. |
| 7,879,079 | B2 | 2/2011 | Tu et al. |
| 7,887,517 | B2 | 2/2011 | Santos et al. |
| 7,887,521 | B2 | 2/2011 | Dacquey et al. |
| 7,951,155 | B2 | 5/2011 | Smedley et al. |
| 7,953,203 | B2 | 5/2011 | Gertner et al. |
| 7,958,840 | B2 | 6/2011 | Chappa |
| 7,967,772 | B2 | 6/2011 | McKenzie et al. |
| 7,978,819 | B2 | 7/2011 | Gertner et al. |
| 7,985,415 | B2 | 7/2011 | Giroux |
| 7,997,460 | B2 | 8/2011 | Pardes et al. |
| 8,007,459 | B2 | 8/2011 | Haffner et al. |
| D645,489 | S | 9/2011 | Gille et al. |
| D645,490 | S | 9/2011 | Gille et al. |
| 8,012,136 | B2 | 9/2011 | Collins, Jr. et al. |
| 8,059,784 | B2 | 11/2011 | Gertner |
| 8,060,211 | B2 | 11/2011 | Greenberg et al. |
| 8,062,244 | B2 | 11/2011 | Tu et al. |
| 8,062,657 | B2 | 11/2011 | Edelman et al. |
| 8,070,290 | B2 | 12/2011 | Gille et al. |
| 8,071,120 | B2 | 12/2011 | Wong |
| 8,073,105 | B2 | 12/2011 | Gertner et al. |
| 8,075,511 | B2 | 12/2011 | Tu et al. |
| 8,118,768 | B2 | 2/2012 | Tu et al. |
| 8,142,364 | B2 | 3/2012 | Haffner et al. |
| 8,152,752 | B2 | 4/2012 | Lynch et al. |
| 8,235,053 | B2 | 8/2012 | Sanchez et al. |
| 8,241,656 | B2 | 8/2012 | Chudzik et al. |
| 8,273,050 | B2 | 9/2012 | Bergheim et al. |
| 8,273,366 | B2 | 9/2012 | Chauhan et al. |
| 8,277,830 | B2 | 10/2012 | De Juan, Jr et al. |
| 8,282,593 | B2 | 10/2012 | Dacey, Jr. et al. |
| 8,298,578 | B2 | 10/2012 | De Juan, Jr. et al. |
| 8,333,726 | B2 | 12/2012 | Rapaki et al. |
| 8,333,742 | B2 | 12/2012 | Bergheim et al. |
| 8,337,445 | B2 | 12/2012 | Tu et al. |
| 8,343,086 | B2 | 1/2013 | Dacey, Jr. et al. |
| 8,348,877 | B2 | 1/2013 | Tu et al. |
| 8,366,652 | B2 | 2/2013 | Dacey et al. |
| 8,388,568 | B2 | 3/2013 | Lynch et al. |
| 8,404,269 | B2 | 3/2013 | Snyder et al. |
| 8,414,517 | B2 | 4/2013 | Dacey, Jr. et al. |
| 8,414,518 | B2 | 4/2013 | Schieber et al. |
| 8,425,929 | B2 | 4/2013 | Huang et al. |
| 8,440,216 | B2 | 5/2013 | Huang et al. |
| 8,444,589 | B2 | 5/2013 | Silvestrini |
| 8,452,391 | B2 | 5/2013 | Roy |
| 8,454,582 | B2 | 6/2013 | Dejuan et al. |
| 8,475,374 | B2 | 7/2013 | Irazoqui et al. |
| 8,486,031 | B2 | 7/2013 | Bogdan |
| 8,486,052 | B2 | 7/2013 | Varner et al. |
| 8,506,515 | B2 | 8/2013 | Burns et al. |
| 8,529,492 | B2 | 9/2013 | Luke et al. |
| 8,579,846 | B2 | 11/2013 | Tu et al. |
| 8,617,094 | B2 | 12/2013 | Smedley et al. |
| 8,642,066 | B2 | 2/2014 | Abe et al. |
| 8,656,958 | B2 | 2/2014 | Unger et al. |
| 8,657,804 | B2 | 2/2014 | Horne et al. |
| 8,771,217 | B2 | 7/2014 | Lynch et al. |
| 8,801,648 | B2 | 8/2014 | Bergheim et al. |
| 8,808,219 | B2 | 8/2014 | Bergheim et al. |
| 8,814,820 | B2 | 8/2014 | Bergheim et al. |
| 8,882,781 | B2 | 11/2014 | Smedley et al. |
| 9,022,967 | B2 | 5/2015 | Oliver et al. |
| 9,066,782 | B2 | 6/2015 | Tu et al. |
| 9,155,654 | B2 | 10/2015 | Tu et al. |
| 9,173,775 | B2 | 11/2015 | Haffner et al. |
| 9,220,632 | B2 | 12/2015 | Smedley et al. |
| 9,301,875 | B2 | 4/2016 | Tu et al. |
| 9,492,320 | B2 | 11/2016 | Lynch et al. |
| 9,554,940 | B2 | 1/2017 | Haffner et al. |
| 9,561,131 | B2 | 2/2017 | Tu et al. |
| 9,572,963 | B2 | 2/2017 | Tu et al. |
| 9,585,789 | B2 | 3/2017 | Silvestrini et al. |
| 9,592,151 | B2 | 3/2017 | Rangel-Friedman et al. |
| 9,597,230 | B2 | 3/2017 | Haffner et al. |
| 9,603,738 | B2 | 3/2017 | Haffner et al. |
| 9,636,255 | B2 | 5/2017 | Haffner et al. |
| 9,668,915 | B2 | 6/2017 | Haffner et al. |
| 9,730,638 | B2 | 8/2017 | Haffner et al. |
| 9,789,001 | B2 | 10/2017 | Tu et al. |
| 9,827,143 | B2 | 11/2017 | Lynch et al. |
| 9,962,290 | B2 | 5/2018 | Burns et al. |
| 9,987,472 | B2 | 6/2018 | Tu et al. |
| 9,993,368 | B2 | 6/2018 | Bergheim et al. |
| D833,008 | S | 11/2018 | Kalina, Jr. et al. |
| 10,159,601 | B2 | 12/2018 | Berlin |
| 10,188,551 | B2 | 1/2019 | Rangel-Friedman et al. |
| 10,206,813 | B2 | 2/2019 | Haffner et al. |
| D846,738 | S | 4/2019 | Kalina, Jr. et al. |
| 10,245,178 | B1 * | 4/2019 | Heitzmann .......... A61M 31/002 |
| 10,271,989 | B2 | 4/2019 | Haffner et al. |
| 10,285,853 | B2 | 5/2019 | Rangel-Friedman et al. |
| 10,285,856 | B2 | 5/2019 | Tu et al. |
| 10,406,029 | B2 | 9/2019 | Tu et al. |
| 10,485,701 | B2 | 11/2019 | Haffner et al. |
| 10,485,702 | B2 | 11/2019 | Bergheim et al. |
| 10,492,950 | B2 | 12/2019 | Lynch et al. |
| 10,499,809 | B2 | 12/2019 | Kalina, Jr. et al. |
| 10,517,759 | B2 | 12/2019 | Crimaldi et al. |
| 10,568,762 | B2 | 2/2020 | Lynch et al. |
| D886,997 | S | 6/2020 | Kalina, Jr. et al. |
| 10,674,906 | B2 | 6/2020 | Kalina, Jr. et al. |
| 10,813,789 | B2 | 10/2020 | Haffner et al. |
| D901,683 | S | 11/2020 | Kalina, Jr. et al. |
| 10,828,195 | B2 | 11/2020 | Burns et al. |
| 10,828,473 | B2 | 11/2020 | Haffner et al. |
| 10,959,941 | B2 | 3/2021 | Haffner |
| 11,019,996 | B2 | 6/2021 | Kalina, Jr. et al. |
| 11,019,997 | B2 | 6/2021 | Kalina, Jr. et al. |
| 11,116,625 | B2 | 9/2021 | Kalina, Jr. |
| D938,585 | S | 12/2021 | Kalina, Jr. et al. |
| 11,197,780 | B2 | 12/2021 | Haffner et al. |
| 11,253,394 | B2 | 2/2022 | Haffner et al. |
| 11,298,262 | B2 | 4/2022 | Kahook et al. |
| 11,318,043 | B2 * | 5/2022 | Heitzmann ........... A61F 9/0017 |
| 11,376,040 | B2 | 7/2022 | Kalina, Jr. et al. |
| 11,426,306 | B2 | 8/2022 | Haffner et al. |
| 11,523,938 | B2 | 12/2022 | Rangel-Friedman et al. |

(56) References Cited

U.S. PATENT DOCUMENTS

| | | | |
|---|---|---|---|
| 11,559,430 | B2 | 1/2023 | Crimaldi et al. |
| 11,564,833 | B2 | 1/2023 | Burns et al. |
| 11,744,458 | B2 | 9/2023 | Kalina, Jr. et al. |
| 11,771,592 | B2 | 10/2023 | Cable, II et al. |
| 11,779,457 | B2 | 10/2023 | Cable, II et al. |
| 11,806,227 | B2 | 11/2023 | Cable, II et al. |
| 11,813,159 | B2 | 11/2023 | Sussman et al. |
| 11,826,104 | B2 | 11/2023 | Kalina, Jr. et al. |
| 11,883,277 | B2 | 1/2024 | Cable, II et al. |
| 11,903,874 | B2 | 2/2024 | Dennewill et al. |
| 11,925,578 | B2 | 3/2024 | Heitzmann et al. |
| 11,944,573 | B2 | 4/2024 | Haffner et al. |
| 11,992,551 | B2 | 5/2024 | Haffner |
| 12,161,548 | B2 | 12/2024 | Sussman et al. |
| 12,186,237 | B2 | 1/2025 | Burns et al. |
| 12,201,555 | B2 | 1/2025 | Haffner et al. |
| 12,201,557 | B2 | 1/2025 | Haffner et al. |
| 12,208,034 | B2 | 1/2025 | Haffner et al. |
| 12,226,308 | B2 | 2/2025 | Kalina, Jr. |
| 12,279,822 | B2 | 4/2025 | Kalina, Jr. et al. |
| 12,343,288 | B2 | 7/2025 | Haffner et al. |
| 12,376,989 | B2 | 8/2025 | Haffner et al. |
| 12,414,798 | B2 | 9/2025 | Kalina, Jr. et al. |
| 12,419,783 | B2 | 9/2025 | Haffner et al. |
| 12,427,057 | B2 | 9/2025 | Haffner et al. |
| 12,478,503 | B2 | 11/2025 | Haffner et al. |
| 12,478,504 | B2 | 11/2025 | Haffner et al. |
| 12,575,972 | B2 | 3/2026 | Crimaldi et al. |
| 12,599,497 | B2 | 4/2026 | Haffner et al. |
| 2002/0013572 | A1 | 1/2002 | Berlin |
| 2002/0052640 | A1 | 5/2002 | Bigus et al. |
| 2002/0071866 | A1 | 6/2002 | Geerke |
| 2002/0102307 | A1 | 8/2002 | Guo et al. |
| 2002/0106395 | A1 | 8/2002 | Brubaker |
| 2002/0110591 | A1 | 8/2002 | Brubaker et al. |
| 2002/0110592 | A1 | 8/2002 | Brubaker et al. |
| 2002/0110635 | A1 | 8/2002 | Brubaker et al. |
| 2002/0111601 | A1 | 8/2002 | Thompson |
| 2002/0111603 | A1 | 8/2002 | Cheikh |
| 2002/0127250 | A1 | 9/2002 | Guo et al. |
| 2002/0128704 | A1 | 9/2002 | Daum et al. |
| 2002/0133168 | A1 | 9/2002 | Smedley et al. |
| 2002/0143284 | A1 | 10/2002 | Tu et al. |
| 2002/0176844 | A1 | 11/2002 | Ng et al. |
| 2002/0182185 | A1 | 12/2002 | Wong |
| 2002/0188282 | A1 | 12/2002 | Greenberg |
| 2002/0197298 | A1 | 12/2002 | Yaacobi |
| 2003/0003129 | A1 | 1/2003 | Yaacobi |
| 2003/0004209 | A1 | 1/2003 | Hunter et al. |
| 2003/0010638 | A1 | 1/2003 | Hansord et al. |
| 2003/0018295 | A1 | 1/2003 | Henley et al. |
| 2003/0019833 | A1 | 1/2003 | Unger et al. |
| 2003/0021828 | A1 | 1/2003 | Guo et al. |
| 2003/0055372 | A1 | 3/2003 | Lynch et al. |
| 2003/0060752 | A1 | 3/2003 | Bergheim et al. |
| 2003/0060873 | A1 | 3/2003 | Gertner et al. |
| 2003/0064088 | A1 | 4/2003 | Carvalho et al. |
| 2003/0083646 | A1 | 5/2003 | Sirhan et al. |
| 2003/0093063 | A1 | 5/2003 | Carr et al. |
| 2003/0095995 | A1 | 5/2003 | Wong et al. |
| 2003/0097117 | A1 | 5/2003 | Buono |
| 2003/0097151 | A1 | 5/2003 | Smedley et al. |
| 2003/0108588 | A1 | 6/2003 | Chen et al. |
| 2003/0119000 | A1 | 6/2003 | Polansky |
| 2003/0139784 | A1 | 7/2003 | Morimoto et al. |
| 2003/0143274 | A1 | 7/2003 | Viegas et al. |
| 2003/0175324 | A1 | 9/2003 | Robinson et al. |
| 2003/0176854 | A1 | 9/2003 | Rodstrom |
| 2003/0181848 | A1 | 9/2003 | Bergheim et al. |
| 2003/0187384 | A1 | 10/2003 | Bergheim et al. |
| 2003/0195438 | A1 | 10/2003 | Petillo |
| 2003/0203003 | A1 | 10/2003 | Nelson et al. |
| 2003/0208163 | A1 | 11/2003 | Yaron et al. |
| 2003/0211071 | A1 | 11/2003 | Bologna et al. |
| 2003/0229303 | A1 | 12/2003 | Haffner et al. |
| 2003/0236484 | A1 | 12/2003 | Lynch et al. |
| 2004/0013702 | A1 | 1/2004 | Glover |
| 2004/0018238 | A1 | 1/2004 | Shukla |
| 2004/0022853 | A1 | 2/2004 | Ashton et al. |
| 2004/0024345 | A1 | 2/2004 | Gharib et al. |
| 2004/0034357 | A1 | 2/2004 | Beane et al. |
| 2004/0057979 | A1 | 3/2004 | Wong et al. |
| 2004/0082939 | A1 | 4/2004 | Berlin |
| 2004/0092548 | A1 | 5/2004 | Embleton et al. |
| 2004/0092911 | A1 | 5/2004 | Yaacobi |
| 2004/0111050 | A1 | 6/2004 | Smedley et al. |
| 2004/0111080 | A1 | 6/2004 | Harper et al. |
| 2004/0115268 | A1 | 6/2004 | Ashton et al. |
| 2004/0127843 | A1 | 7/2004 | Tu et al. |
| 2004/0131654 | A1 | 7/2004 | Yaacobi |
| 2004/0131655 | A1 | 7/2004 | Yaacobi |
| 2004/0137059 | A1 | 7/2004 | Nivaggioli et al. |
| 2004/0147870 | A1 | 7/2004 | Burns et al. |
| 2004/0151714 | A1 | 8/2004 | Soll |
| 2004/0154946 | A1 | 8/2004 | Solovay et al. |
| 2004/0163652 | A1 | 8/2004 | Watson |
| 2004/0175410 | A1 | 9/2004 | Ashton et al. |
| 2004/0176341 | A1 | 9/2004 | Chou et al. |
| 2004/0176737 | A1 | 9/2004 | Henley et al. |
| 2004/0180075 | A1 | 9/2004 | Robinson et al. |
| 2004/0186533 | A1 | 9/2004 | Greenberg et al. |
| 2004/0186534 | A1 | 9/2004 | Shadduck |
| 2004/0208909 | A1 | 10/2004 | Brubaker et al. |
| 2004/0208910 | A1 | 10/2004 | Ashton et al. |
| 2004/0210185 | A1 | 10/2004 | Tu et al. |
| 2004/0216749 | A1 | 11/2004 | Tu |
| 2004/0219181 | A1 | 11/2004 | Viscasillas |
| 2004/0220537 | A1 | 11/2004 | Embleton et al. |
| 2004/0225250 | A1 | 11/2004 | Yablonski |
| 2004/0249404 | A1 | 12/2004 | Haefliger |
| 2004/0254519 | A1 | 12/2004 | Tu et al. |
| 2004/0254520 | A1 | 12/2004 | Porteous et al. |
| 2004/0254521 | A1 | 12/2004 | Simon |
| 2004/0260228 | A1 | 12/2004 | Lynch et al. |
| 2004/0265356 | A1 | 12/2004 | Mosack |
| 2005/0008673 | A1 | 1/2005 | Snyder et al. |
| 2005/0042293 | A1 | 2/2005 | Jackson et al. |
| 2005/0049578 | A1 | 3/2005 | Tu et al. |
| 2005/0055075 | A1 | 3/2005 | Pinchuk et al. |
| 2005/0064010 | A1 | 3/2005 | Cooper et al. |
| 2005/0069893 | A1 | 3/2005 | Flammer et al. |
| 2005/0107734 | A1 | 5/2005 | Coroneo |
| 2005/0112175 | A1 | 5/2005 | Yaacobi |
| 2005/0119737 | A1 | 6/2005 | Bene et al. |
| 2005/0137538 | A1 | 6/2005 | Kunzler et al. |
| 2005/0159660 | A1 | 7/2005 | Montegrande et al. |
| 2005/0165368 | A1 | 7/2005 | Py et al. |
| 2005/0171490 | A1 | 8/2005 | Weaver et al. |
| 2005/0175708 | A1 | 8/2005 | Carrasquillo et al. |
| 2005/0181018 | A1 | 8/2005 | Peyman |
| 2005/0186245 | A1 | 8/2005 | Hunter et al. |
| 2005/0186279 | A1 | 8/2005 | Guo et al. |
| 2005/0208102 | A1 | 9/2005 | Schultz |
| 2005/0209549 | A1 | 9/2005 | Bergheim et al. |
| 2005/0222537 | A1 | 10/2005 | Dinsmoor et al. |
| 2005/0232972 | A1 | 10/2005 | Odrich |
| 2005/0244461 | A1 | 11/2005 | Nivaggioli et al. |
| 2005/0244464 | A1 | 11/2005 | Hughes |
| 2005/0244465 | A1 | 11/2005 | Nivaggioli et al. |
| 2005/0244467 | A1 | 11/2005 | Nivaggioli et al. |
| 2005/0244470 | A1 | 11/2005 | Hughes et al. |
| 2005/0244475 | A1 | 11/2005 | Edelman et al. |
| 2005/0244477 | A1 | 11/2005 | Hughes et al. |
| 2005/0244500 | A1 | 11/2005 | Whitcup et al. |
| 2005/0244506 | A1 | 11/2005 | Burke et al. |
| 2005/0249710 | A1 | 11/2005 | Wong |
| 2005/0250788 | A1 | 11/2005 | Tu et al. |
| 2005/0261641 | A1 | 11/2005 | Warchol et al. |
| 2005/0266047 | A1 | 12/2005 | Tu et al. |
| 2005/0276841 | A1 | 12/2005 | Davis et al. |
| 2005/0277864 | A1 | 12/2005 | Haffner et al. |
| 2005/0281861 | A1 | 12/2005 | Hughes et al. |
| 2005/0287188 | A1 | 12/2005 | Anderson et al. |
| 2005/0288619 | A1 | 12/2005 | Gharib et al. |

(56) References Cited

U.S. PATENT DOCUMENTS

| | | |
|---|---|---|
| 2006/0009498 A1 | 1/2006 | Whitcup |
| 2006/0020248 A1 | 1/2006 | Prescott |
| 2006/0020253 A1 | 1/2006 | Prescott |
| 2006/0021623 A1 | 2/2006 | Varner et al. |
| 2006/0024350 A1 | 2/2006 | Miller et al. |
| 2006/0032507 A1 | 2/2006 | Tu |
| 2006/0034929 A1 | 2/2006 | Brubaker |
| 2006/0039952 A1 | 2/2006 | Yaacobi |
| 2006/0039979 A1 | 2/2006 | Yamada et al. |
| 2006/0062826 A1 | 3/2006 | Brubaker et al. |
| 2006/0067978 A1 | 3/2006 | Heiler et al. |
| 2006/0067980 A1 | 3/2006 | Hennessy et al. |
| 2006/0069340 A1 | 3/2006 | Simon |
| 2006/0074375 A1 | 4/2006 | Bergheim et al. |
| 2006/0083772 A1 | 4/2006 | DeWitt et al. |
| 2006/0084907 A1 | 4/2006 | Bergheim et al. |
| 2006/0084952 A1 | 4/2006 | Pallikaris et al. |
| 2006/0089590 A1 | 4/2006 | Powell et al. |
| 2006/0100408 A1 | 5/2006 | Higuchi et al. |
| 2006/0110429 A1 | 5/2006 | Reiff et al. |
| 2006/0135918 A1 | 6/2006 | LaRuffa |
| 2006/0136022 A1 | 6/2006 | Wong, Jr. et al. |
| 2006/0167435 A1 | 7/2006 | Adamis et al. |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200097 A1 | 9/2006 | Humayun et al. |
| 2006/0200113 A1 | 9/2006 | Haffner et al. |
| 2006/0210604 A1 | 9/2006 | Dadey et al. |
| 2006/0216329 A1 | 9/2006 | Peyman |
| 2006/0246112 A1 | 11/2006 | Snyder et al. |
| 2006/0246145 A1 | 11/2006 | Chang et al. |
| 2006/0253151 A1 | 11/2006 | Nun |
| 2006/0257450 A1 | 11/2006 | Mudumba et al. |
| 2006/0257451 A1 | 11/2006 | Varner et al. |
| 2006/0258994 A1 | 11/2006 | Avery |
| 2006/0264453 A1 | 11/2006 | Mudumba et al. |
| 2006/0270968 A1 | 11/2006 | Greenberg et al. |
| 2006/0292222 A1 | 12/2006 | Jonasse |
| 2007/0021653 A1 | 1/2007 | Hattenbach et al. |
| 2007/0026037 A1 | 2/2007 | Kloke et al. |
| 2007/0026048 A1 | 2/2007 | Greeberg |
| 2007/0031472 A1 | 2/2007 | Huang et al. |
| 2007/0031473 A1 | 2/2007 | Peyman |
| 2007/0032734 A1 | 2/2007 | Najafi et al. |
| 2007/0038174 A1 | 2/2007 | Hopkins |
| 2007/0059336 A1 | 3/2007 | Hughes et al. |
| 2007/0088014 A1 | 4/2007 | Edelman et al. |
| 2007/0088432 A1 | 4/2007 | Solovay et al. |
| 2007/0092570 A1 | 4/2007 | Missel et al. |
| 2007/0106199 A1 | 5/2007 | Krivoy et al. |
| 2007/0106236 A1 | 5/2007 | Coroneo |
| 2007/0112263 A1 | 5/2007 | Fink et al. |
| 2007/0112318 A1 | 5/2007 | Leahy et al. |
| 2007/0118065 A1 | 5/2007 | Pinchuk et al. |
| 2007/0118066 A1 | 5/2007 | Pinchuk et al. |
| 2007/0123767 A1 | 5/2007 | Montegrande et al. |
| 2007/0129623 A1 | 6/2007 | Fleischman et al. |
| 2007/0190111 A1 | 8/2007 | Robinson et al. |
| 2007/0191863 A1 | 8/2007 | De Juan, Jr. et al. |
| 2007/0197957 A1 | 8/2007 | Hunter et al. |
| 2007/0202186 A1 | 8/2007 | Yamamoto et al. |
| 2007/0212395 A1 | 9/2007 | Donello et al. |
| 2007/0212397 A1 | 9/2007 | Roth |
| 2007/0233037 A1 | 10/2007 | Gifford, III et al. |
| 2007/0243230 A1 | 10/2007 | de Juan et al. |
| 2007/0244442 A1 | 10/2007 | Chowhan |
| 2007/0249984 A1 | 10/2007 | Molteno |
| 2007/0260203 A1 | 11/2007 | Donello et al. |
| 2007/0268340 A1 | 11/2007 | Dacquay et al. |
| 2007/0269487 A1 | 11/2007 | de Juan et al. |
| 2007/0270744 A1 | 11/2007 | Dacquay et al. |
| 2007/0270748 A1 | 11/2007 | Dacquay et al. |
| 2007/0270768 A1 | 11/2007 | Dacquay et al. |
| 2007/0270777 A1 | 11/2007 | Dacquay et al. |
| 2007/0282244 A1 | 12/2007 | Tu et al. |
| 2007/0282245 A1 | 12/2007 | Tu et al. |
| 2007/0292596 A1 | 12/2007 | Chappa et al. |
| 2007/0293807 A1 | 12/2007 | Lynch et al. |
| 2007/0293820 A1 | 12/2007 | Dacquay et al. |
| 2007/0293872 A1 | 12/2007 | Peyman |
| 2007/0293873 A1 | 12/2007 | Chang |
| 2007/0298073 A1 | 12/2007 | Whitcup et al. |
| 2007/0298074 A1 | 12/2007 | Robinson et al. |
| 2007/0299516 A1 | 12/2007 | Cui et al. |
| 2008/0027304 A1 | 1/2008 | Pardo et al. |
| 2008/0038316 A1 | 2/2008 | Wong et al. |
| 2008/0039769 A1 | 2/2008 | Peyman |
| 2008/0039792 A1 | 2/2008 | Meng et al. |
| 2008/0045878 A1 | 2/2008 | Bergheim et al. |
| 2008/0045911 A1 | 2/2008 | Borgia et al. |
| 2008/0051680 A1 | 2/2008 | Luebcke |
| 2008/0057101 A1 | 3/2008 | Roorda |
| 2008/0057102 A1 | 3/2008 | Roorda |
| 2008/0057103 A1 | 3/2008 | Roorda |
| 2008/0057123 A1 | 3/2008 | Grenier et al. |
| 2008/0058704 A1 | 3/2008 | Hee et al. |
| 2008/0058793 A1 | 3/2008 | Pilla et al. |
| 2008/0063687 A1 | 3/2008 | Chou et al. |
| 2008/0063898 A1 | 3/2008 | Lally et al. |
| 2008/0071252 A1 | 3/2008 | Santini, Jr. et al. |
| 2008/0075753 A1 | 3/2008 | Chappa |
| 2008/0081064 A1 | 4/2008 | Jelle et al. |
| 2008/0086101 A1 | 4/2008 | Freilich |
| 2008/0089923 A1 | 4/2008 | Burkstrand et al. |
| 2008/0095822 A1 | 4/2008 | Maquet et al. |
| 2008/0097379 A1 | 4/2008 | Daquay et al. |
| 2008/0097390 A1 | 4/2008 | Daquay et al. |
| 2008/0107694 A1 | 5/2008 | Trogden et al. |
| 2008/0112923 A1 | 5/2008 | Hughes et al. |
| 2008/0113031 A1 | 5/2008 | Moodley et al. |
| 2008/0114076 A1 | 5/2008 | Asgharian et al. |
| 2008/0125712 A1 | 5/2008 | Dacquay et al. |
| 2008/0131372 A1 | 6/2008 | Huang et al. |
| 2008/0131481 A1 | 6/2008 | Hughes |
| 2008/0131482 A1 | 6/2008 | Hughes |
| 2008/0131484 A1 | 6/2008 | Robinson et al. |
| 2008/0131486 A1 | 6/2008 | Huang et al. |
| 2008/0138382 A1 | 6/2008 | Huang et al. |
| 2008/0138408 A1 | 6/2008 | Venkatesh et al. |
| 2008/0140024 A1 | 6/2008 | Yaacobi |
| 2008/0145405 A1 | 6/2008 | Kunzler et al. |
| 2008/0145406 A1 | 6/2008 | Asgharian et al. |
| 2008/0147021 A1 | 6/2008 | Jani |
| 2008/0152694 A1 | 6/2008 | Lobl et al. |
| 2008/0161741 A1 | 7/2008 | Bene et al. |
| 2008/0161907 A1 | 7/2008 | Chen et al. |
| 2008/0167600 A1 | 7/2008 | Peyman |
| 2008/0172014 A1 | 7/2008 | Whitcup et al. |
| 2008/0177153 A1 | 7/2008 | Bachman et al. |
| 2008/0177220 A1 | 7/2008 | Lindgren et al. |
| 2008/0181928 A1 | 7/2008 | Hokimi-Mehr et al. |
| 2008/0181929 A1 | 7/2008 | Robinson et al. |
| 2008/0183121 A2 | 7/2008 | Smedley et al. |
| 2008/0183123 A1 | 7/2008 | Behar-Cohen et al. |
| 2008/0208334 A1 | 8/2008 | Jinkerson et al. |
| 2008/0208557 A1 | 8/2008 | Katano |
| 2008/0210322 A1 | 9/2008 | Unger et al. |
| 2008/0228127 A1 | 9/2008 | Burns et al. |
| 2008/0231485 A1 | 9/2008 | Newlin et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0236669 A1 | 10/2008 | Unger et al. |
| 2008/0241222 A1 | 10/2008 | Whitcup et al. |
| 2008/0241223 A1 | 10/2008 | Nivaggio et al. |
| 2008/0260803 A1 | 10/2008 | Hughes et al. |
| 2008/0277007 A1 | 11/2008 | Unger et al. |
| 2008/0286336 A1 | 11/2008 | Shiah et al. |
| 2008/0286338 A1 | 11/2008 | Rosenthal et al. |
| 2008/0289710 A1 | 11/2008 | Unger et al. |
| 2008/0292679 A1 | 11/2008 | Lyons et al. |
| 2008/0306429 A1 | 12/2008 | Shields et al. |
| 2008/0318843 A1 | 12/2008 | Schultz et al. |

(56) References Cited

U.S. PATENT DOCUMENTS

| | | |
|---|---|---|
| 2009/0003525 A1 | 1/2009 | Gertner et al. |
| 2009/0036768 A1 | 2/2009 | Seehusen et al. |
| 2009/0043250 A1 | 2/2009 | Gonnelli |
| 2009/0043321 A1 | 2/2009 | Conston et al. |
| 2009/0047256 A1 | 2/2009 | Bettinger et al. |
| 2009/0060981 A1 | 3/2009 | Chauhan |
| 2009/0069648 A1 | 3/2009 | Irazoqui et al. |
| 2009/0074786 A1 | 3/2009 | Dor et al. |
| 2009/0076436 A2 | 3/2009 | Gharib et al. |
| 2009/0082321 A1 | 3/2009 | Edelman et al. |
| 2009/0092654 A1 | 4/2009 | de Juan, Jr. et al. |
| 2009/0093780 A1 | 4/2009 | Tuitupou et al. |
| 2009/0093788 A1 | 4/2009 | Sanchez, Jr. et al. |
| 2009/0112190 A1 | 4/2009 | Boyden et al. |
| 2009/0118702 A1 | 5/2009 | Lazar |
| 2009/0123515 A1 | 5/2009 | Taylor et al. |
| 2009/0123546 A1 | 5/2009 | Ashton et al. |
| 2009/0142413 A1 | 6/2009 | Allen et al. |
| 2009/0143752 A1 | 6/2009 | Higuchi et al. |
| 2009/0148498 A1 | 6/2009 | Libin et al. |
| 2009/0149947 A1 | 6/2009 | Frohwitter |
| 2009/0151422 A1 | 6/2009 | Unger et al. |
| 2009/0155338 A1 | 6/2009 | Conway et al. |
| 2009/0157087 A1 | 6/2009 | Wei et al. |
| 2009/0162417 A1 | 6/2009 | Eellis |
| 2009/0177182 A1 | 7/2009 | Hickingbotham et al. |
| 2009/0196903 A1 | 8/2009 | Kilman |
| 2009/0196906 A1 | 8/2009 | Spada et al. |
| 2009/0209945 A1 | 8/2009 | Lobl et al. |
| 2009/0214619 A1 | 8/2009 | Reiff et al. |
| 2009/0220572 A1 | 9/2009 | Deschatelets et al. |
| 2009/0220573 A1 | 9/2009 | Kaufman |
| 2009/0227933 A1 | 9/2009 | Karageozian |
| 2009/0240215 A1 | 9/2009 | Humayun et al. |
| 2009/0246252 A1 | 10/2009 | Arps et al. |
| 2009/0264861 A1 | 10/2009 | Jain et al. |
| 2009/0270308 A1 | 10/2009 | Libin et al. |
| 2009/0274877 A1 | 11/2009 | Chan et al. |
| 2009/0275924 A1 | 11/2009 | Lattanzio et al. |
| 2009/0280155 A1 | 11/2009 | Chappa et al. |
| 2009/0280158 A1* | 11/2009 | Butuner ................ A61P 27/02 |
| | | 424/428 |
| 2009/0286773 A1 | 11/2009 | Spada et al. |
| 2009/0287274 A1 | 11/2009 | De Rodder |
| 2009/0294345 A1 | 12/2009 | Kelly et al. |
| 2009/0306585 A1 | 12/2009 | Pang et al. |
| 2009/0306595 A1 | 12/2009 | Shih et al. |
| 2009/0306608 A1* | 12/2009 | Li ...................... A61F 9/0017 |
| | | 604/294 |
| 2009/0312742 A1 | 12/2009 | Pang et al. |
| 2009/0326432 A1 | 12/2009 | Schmidt et al. |
| 2010/0004581 A1 | 1/2010 | Brigatti et al. |
| 2010/0004639 A1 | 1/2010 | Pang et al. |
| 2010/0015195 A1 | 1/2010 | Jain et al. |
| 2010/0030136 A1 | 2/2010 | Dacquay et al. |
| 2010/0040670 A1 | 2/2010 | Odrich et al. |
| 2010/0056979 A1 | 3/2010 | Smedley et al. |
| 2010/0057003 A1 | 3/2010 | Dos Santos |
| 2010/0068141 A1 | 3/2010 | Kaushal et al. |
| 2010/0069842 A1 | 3/2010 | Dos Santos et al. |
| 2010/0092536 A1 | 4/2010 | Hunter et al. |
| 2010/0100054 A1 | 4/2010 | Cormier et al. |
| 2010/0114039 A1 | 5/2010 | Gazzini |
| 2010/0114309 A1 | 5/2010 | Peyman |
| 2010/0119519 A1 | 5/2010 | Peyman |
| 2010/0119580 A1 | 5/2010 | Guo et al. |
| 2010/0119694 A1 | 5/2010 | Guo et al. |
| 2010/0124565 A1 | 5/2010 | Spada et al. |
| 2010/0129424 A9 | 5/2010 | Byrne et al. |
| 2010/0137780 A1 | 6/2010 | Singh et al. |
| 2010/0145180 A1 | 6/2010 | Abreu |
| 2010/0152676 A1 | 6/2010 | Clements |
| 2010/0152699 A1 | 6/2010 | Ferrari et al. |
| 2010/0158980 A1 | 6/2010 | Kopczynski et al. |
| 2010/0160870 A1 | 6/2010 | Clements et al. |
| 2010/0173866 A1 | 7/2010 | Hee et al. |
| 2010/0174272 A1 | 7/2010 | Weiner |
| 2010/0189765 A1 | 7/2010 | Erickson et al. |
| 2010/0189817 A1 | 7/2010 | Kruger et al. |
| 2010/0191103 A1 | 7/2010 | Stamper et al. |
| 2010/0203155 A1 | 8/2010 | Wei et al. |
| 2010/0204325 A1 | 8/2010 | Blanda et al. |
| 2010/0204699 A1 | 8/2010 | Wei et al. |
| 2010/0211044 A1 | 8/2010 | Dacquay et al. |
| 2010/0222752 A1 | 9/2010 | Collins, Jr. et al. |
| 2010/0225061 A1 | 9/2010 | Bath |
| 2010/0233241 A1 | 9/2010 | Leahy et al. |
| 2010/0234817 A1 | 9/2010 | Nazzaro et al. |
| 2010/0239635 A1 | 9/2010 | McClain et al. |
| 2010/0239637 A1 | 9/2010 | Ciolino et al. |
| 2010/0241046 A1 | 9/2010 | Pinchuk et al. |
| 2010/0241055 A1 | 9/2010 | Dacey, Jr. et al. |
| 2010/0247606 A1 | 9/2010 | Robinson et al. |
| 2010/0249692 A1 | 9/2010 | Dacey, Jr. et al. |
| 2010/0255061 A1 | 10/2010 | de Juan, Jr. et al. |
| 2010/0256578 A1 | 10/2010 | Lust et al. |
| 2010/0256597 A1 | 10/2010 | Prausnitz et al. |
| 2010/0261646 A1 | 10/2010 | Lavik et al. |
| 2010/0266664 A1 | 10/2010 | Asgharian et al. |
| 2010/0274224 A1 | 10/2010 | Jain et al. |
| 2010/0274258 A1 | 10/2010 | Silvestrini et al. |
| 2010/0274259 A1 | 10/2010 | Yaron et al. |
| 2010/0278898 A1 | 11/2010 | Hughes et al. |
| 2010/0318034 A1 | 12/2010 | Goncalves |
| 2010/0331796 A1 | 12/2010 | Leahy et al. |
| 2011/0022007 A1 | 1/2011 | Li et al. |
| 2011/0053905 A1 | 3/2011 | Guo et al. |
| 2011/0054418 A1 | 3/2011 | Pugh et al. |
| 2011/0076318 A1 | 3/2011 | Hughes et al. |
| 2011/0091520 A1 | 4/2011 | Huang et al. |
| 2011/0098632 A1 | 4/2011 | Behar-Cohen et al. |
| 2011/0098640 A1 | 4/2011 | Horne et al. |
| 2011/0104155 A1 | 5/2011 | Rekik |
| 2011/0106006 A1 | 5/2011 | Martin et al. |
| 2011/0112352 A1 | 5/2011 | Pilla et al. |
| 2011/0112470 A1 | 5/2011 | Lingenfelder et al. |
| 2011/0112475 A1 | 5/2011 | Benson |
| 2011/0125090 A1 | 5/2011 | Peyman |
| 2011/0129516 A1 | 6/2011 | Jacob et al. |
| 2011/0129541 A1 | 6/2011 | Chen et al. |
| 2011/0152767 A1 | 6/2011 | Pinedjian |
| 2011/0166500 A1 | 7/2011 | Roy |
| 2011/0172528 A1 | 7/2011 | Gertner |
| 2011/0172587 A1 | 7/2011 | Santini, Jr. et al. |
| 2011/0182966 A1 | 7/2011 | Robinson et al. |
| 2011/0202020 A1 | 8/2011 | Lazar |
| 2011/0207987 A1 | 8/2011 | DiCarlo et al. |
| 2011/0238036 A1 | 9/2011 | Ashton |
| 2011/0238075 A1 | 9/2011 | Clauson et al. |
| 2011/0244010 A1 | 10/2011 | Doshi |
| 2011/0251568 A1 | 10/2011 | Beeley et al. |
| 2011/0288396 A1 | 11/2011 | Iyengar et al. |
| 2012/0022505 A1 | 1/2012 | Dacquay et al. |
| 2012/0035146 A1 | 2/2012 | Wong et al. |
| 2012/0035528 A1 | 2/2012 | Coppeta et al. |
| 2012/0059349 A1 | 3/2012 | Kuo et al. |
| 2012/0078158 A1 | 3/2012 | Haffner et al. |
| 2012/0078224 A1 | 3/2012 | Lerner et al. |
| 2012/0078362 A1 | 3/2012 | Haffner et al. |
| 2012/0083765 A1 | 4/2012 | LaBelle |
| 2012/0089072 A1 | 4/2012 | Cunningham, Jr. |
| 2012/0089073 A1 | 4/2012 | Cunningham, Jr. |
| 2012/0089113 A1 | 4/2012 | Ambati et al. |
| 2012/0100187 A1 | 4/2012 | Chappa et al. |
| 2012/0107371 A1 | 5/2012 | Zion et al. |
| 2012/0136322 A1 | 5/2012 | Alster et al. |
| 2012/0157487 A1 | 6/2012 | Yuan et al. |
| 2012/0165933 A1 | 6/2012 | Haffner et al. |
| 2012/0177717 A1 | 7/2012 | Abe et al. |
| 2012/0179122 A1 | 7/2012 | Eilat et al. |
| 2012/0197217 A1 | 8/2012 | Coldren |
| 2012/0238994 A1 | 9/2012 | Nazzaro et al. |
| 2012/0245505 A1 | 9/2012 | Robinson et al. |
| 2012/0253300 A1 | 10/2012 | Kaufman |

(56) References Cited

U.S. PATENT DOCUMENTS

| | | |
|---|---|---|
| 2012/0257167 A1 | 10/2012 | Gille et al. |
| 2012/0259195 A1 | 10/2012 | Haffner et al. |
| 2012/0265149 A1 | 10/2012 | Lerner et al. |
| 2012/0277733 A1 | 11/2012 | Pang et al. |
| 2012/0321719 A1 | 12/2012 | McDonnell et al. |
| 2013/0004651 A1 | 1/2013 | Fu-Giles |
| 2013/0017244 A1 | 1/2013 | Huang et al. |
| 2013/0017262 A1 | 1/2013 | Mullen et al. |
| 2013/0018295 A1 | 1/2013 | Haffner et al. |
| 2013/0018296 A1 | 1/2013 | Bergheim et al. |
| 2013/0018360 A1 | 1/2013 | Dockendorf et al. |
| 2013/0023838 A1 | 1/2013 | Leahy et al. |
| 2013/0053794 A1 | 2/2013 | Cadden et al. |
| 2013/0060227 A1 | 3/2013 | Singh et al. |
| 2013/0062809 A1 | 3/2013 | Ellis et al. |
| 2013/0071349 A1 | 3/2013 | Robinson et al. |
| 2013/0071462 A1 | 3/2013 | Jarrett et al. |
| 2013/0090534 A1 | 4/2013 | Burns et al. |
| 2013/0090612 A1 | 4/2013 | De Juan, Jr. et al. |
| 2013/0110125 A1 | 5/2013 | Silvestrini et al. |
| 2013/0116523 A1 | 5/2013 | Jung et al. |
| 2013/0142858 A1 | 6/2013 | Kopczynski et al. |
| 2013/0144128 A1 | 6/2013 | De Juan, Jr. et al. |
| 2013/0150770 A1 | 6/2013 | Horvath et al. |
| 2013/0150773 A1 | 6/2013 | Nissan et al. |
| 2013/0150774 A1 | 6/2013 | Field et al. |
| 2013/0156840 A1 | 6/2013 | Basinger et al. |
| 2013/0158561 A1 | 6/2013 | Bhagat |
| 2013/0253404 A1 | 9/2013 | Tu |
| 2013/0253405 A1 | 9/2013 | Tu |
| 2013/0253437 A1 | 9/2013 | Badawi et al. |
| 2013/0281908 A1 | 10/2013 | Schaller et al. |
| 2013/0281910 A1 | 10/2013 | Tu |
| 2013/0289467 A1* | 10/2013 | Haffner ................ A61K 9/2072 |
| | | 604/290 |
| 2013/0310930 A1 | 11/2013 | Tu et al. |
| 2014/0035184 A1 | 2/2014 | Nivaggioli et al. |
| 2014/0037746 A1 | 2/2014 | Ashton et al. |
| 2014/0039456 A1 | 2/2014 | Lerner |
| 2014/0135712 A1 | 5/2014 | Horne et al. |
| 2014/0234389 A1 | 8/2014 | Shiah et al. |
| 2014/0294986 A1 | 10/2014 | Liu et al. |
| 2015/0118279 A1 | 4/2015 | Ghebremeskel et al. |
| 2015/0223981 A1 | 8/2015 | Smedley et al. |
| 2015/0238687 A1 | 8/2015 | Novakovic et al. |
| 2015/0342875 A1 | 12/2015 | Haffner |
| 2016/0045363 A1 | 2/2016 | Haffner et al. |
| 2016/0354245 A1 | 12/2016 | Horvath et al. |
| 2016/0354309 A1 | 12/2016 | Heitzmann et al. |
| 2017/0135857 A1 | 5/2017 | Haffner et al. |
| 2018/0021170 A1 | 1/2018 | Haffner et al. |
| 2018/0028361 A1 | 2/2018 | Haffner et al. |
| 2018/0085065 A1 | 3/2018 | Haffner et al. |
| 2018/0161205 A1 | 6/2018 | Tu et al. |
| 2018/0256393 A1 | 9/2018 | Yamamoto et al. |
| 2018/0280194 A1 | 10/2018 | Heitzmann et al. |
| 2018/0303665 A1 | 10/2018 | Heitzmann et al. |
| 2018/0333296 A1 | 11/2018 | Heitzmann et al. |
| 2019/0000673 A1 | 1/2019 | Fjield et al. |
| 2019/0021991 A9 | 1/2019 | Heitzmann et al. |
| 2019/0053704 A1 | 2/2019 | Burns et al. |
| 2019/0083307 A1 | 3/2019 | Burns et al. |
| 2019/0083313 A1 | 3/2019 | Berlin |
| 2019/0104936 A1 | 4/2019 | Gunn et al. |
| 2019/0125581 A1 | 5/2019 | Heitzmann et al. |
| 2019/0224046 A1 | 7/2019 | Heitzmann et al. |
| 2019/0314199 A1 | 10/2019 | Haffner et al. |
| 2019/0321220 A1 | 10/2019 | Rangel-Friedman et al. |
| 2019/0321225 A1 | 10/2019 | Smedley et al. |
| 2020/0000635 A1 | 1/2020 | Lerner |
| 2020/0155349 A1 | 5/2020 | Haffner et al. |
| 2020/0179171 A1 | 6/2020 | Crimaldi et al. |
| 2020/0367745 A1 | 11/2020 | Kalina, Jr. et al. |
| 2021/0015662 A1 | 1/2021 | Haffner et al. |
| 2021/0137737 A1 | 5/2021 | Burns et al. |
| 2021/0154449 A1 | 5/2021 | Haffner et al. |
| 2021/0298948 A1 | 9/2021 | Haffner et al. |
| 2021/0315806 A1 | 10/2021 | Haffner |
| 2021/0369447 A1 | 12/2021 | Kalina, Jr. |
| 2022/0000663 A1 | 1/2022 | Haffner et al. |
| 2022/0015628 A1 | 1/2022 | Kalina, Jr. et al. |
| 2022/0119350 A1 | 4/2022 | Murphy et al. |
| 2022/0233349 A1 | 7/2022 | Haffner et al. |
| 2022/0233354 A1 | 7/2022 | Haffner et al. |
| 2022/0330979 A1 | 10/2022 | Kalina, Jr. et al. |
| 2023/0053931 A1 | 2/2023 | Haffner et al. |
| 2023/0090539 A1 | 3/2023 | Haffner et al. |
| 2023/0157868 A1 | 5/2023 | Haffner et al. |
| 2023/0210694 A1 | 7/2023 | Crimaldi et al. |
| 2023/0293344 A1 | 9/2023 | Burns et al. |
| 2023/0301830 A1 | 9/2023 | Heitzmann et al. |
| 2023/0372303 A1 | 11/2023 | Liu et al. |
| 2024/0024093 A1 | 1/2024 | Cable, III et al. |
| 2024/0065887 A1 | 2/2024 | Heitzmann et al. |
| 2024/0090762 A1 | 3/2024 | Kalina, Jr. et al. |
| 2024/0207091 A1 | 6/2024 | Heitzmann et al. |
| 2025/0057758 A1 | 2/2025 | Haffner |
| 2025/0107929 A1 | 4/2025 | Haffner et al. |
| 2025/0134714 A1 | 5/2025 | Burns et al. |
| 2025/0161109 A1 | 5/2025 | Haffner et al. |
| 2025/0161110 A1 | 5/2025 | Heitzmann et al. |
| 2025/0161206 A1 | 5/2025 | Haffner |
| 2025/0169986 A1 | 5/2025 | Haffner et al. |
| 2025/0288461 A1 | 9/2025 | Haffner et al. |
| 2025/0312190 A1 | 10/2025 | Haffner et al. |
| 2025/0375314 A1 | 12/2025 | Haffner et al. |
| 2025/0387138 A1 | 12/2025 | Kalina, Jr. et al. |
| 2026/0000537 A1 | 1/2026 | Haffner et al. |

FOREIGN PATENT DOCUMENTS

| | | |
|---|---|---|
| CA | 2442652 | 1/2011 |
| CA | 2830555 | 4/2015 |
| CA | 2762536 | 11/2020 |
| CN | 101396335 | 4/2009 |
| CN | 103209664 | 7/2013 |
| CN | 104540472 | 4/2015 |
| EP | 0180708 | 5/1986 |
| EP | 0387155 | 9/1990 |
| EP | 0613383 | 8/1997 |
| EP | 1100462 | 5/2001 |
| EP | 1296645 | 4/2003 |
| EP | 1339438 | 9/2003 |
| EP | 1420716 | 5/2004 |
| EP | 1477187 | 11/2004 |
| EP | 1534363 | 6/2005 |
| EP | 1550471 | 7/2005 |
| EP | 1592407 | 11/2005 |
| EP | 1621219 | 2/2006 |
| EP | 1637126 | 3/2006 |
| EP | 1521573 | 1/2008 |
| EP | 2902018 | 11/2016 |
| ES | 2048986 | 4/1994 |
| FR | 2297779 | 8/1976 |
| JP | 2003-520077 | 7/2003 |
| JP | 2003-275327 | 9/2003 |
| JP | 2003-290362 | 10/2003 |
| JP | 2003-530964 | 10/2003 |
| JP | 2008-500878 | 1/2008 |
| JP | 2009-523540 | 6/2009 |
| JP | 2009-532132 | 9/2009 |
| JP | 2011-520805 | 7/2011 |
| JP | 2011-522575 | 8/2011 |
| JP | 2011-522695 | 8/2011 |
| JP | 2012-516224 | 7/2012 |
| JP | 2012-198134 | 9/2012 |
| JP | 2013-063308 | 4/2013 |
| JP | 2014-504732 | 2/2014 |
| JP | 2014-236980 | 12/2014 |
| JP | 2016-511108 | 4/2016 |
| WO | WO 1994/02081 | 2/1994 |
| WO | WO 1995/013765 | 5/1995 |
| WO | WO 1996/020742 | 7/1996 |
| WO | WO 1996/038174 | 12/1996 |

(56)                  References Cited

FOREIGN PATENT DOCUMENTS

| WO | WO 1997/035779 | 10/1997 |
| WO | WO 1998/030181 | 7/1998 |
| WO | WO 1998/35639 | 8/1998 |
| WO | WO 1999/11244 | 3/1999 |
| WO | WO 1999/26567 | 6/1999 |
| WO | WO 1999/56637 | 11/1999 |
| WO | WO 2000/007565 | 2/2000 |
| WO | WO 2000/037056 | 6/2000 |
| WO | WO 2000/64389 | 11/2000 |
| WO | WO 2000/64390 | 11/2000 |
| WO | WO 2000/64391 | 11/2000 |
| WO | WO 2000/64393 | 11/2000 |
| WO | WO 2000/72788 | 12/2000 |
| WO | WO 2001/41685 | 6/2001 |
| WO | WO 2001/080825 | 11/2001 |
| WO | WO 2001/97727 | 12/2001 |
| WO | WO 2002/002076 | 1/2002 |
| WO | WO 2002/36052 | 5/2002 |
| WO | WO 2002/043785 | 6/2002 |
| WO | WO 2002/053129 | 7/2002 |
| WO | WO 2002/080811 | 10/2002 |
| WO | WO 2002/087418 | 11/2002 |
| WO | WO 2002/089699 | 11/2002 |
| WO | WO 2003/020172 | 3/2003 |
| WO | WO 2003/061625 | 7/2003 |
| WO | WO 2003/073968 | 9/2003 |
| WO | WO 2004/006890 | 1/2004 |
| WO | WO 2004/043435 | 5/2004 |
| WO | WO 2004/066871 | 8/2004 |
| WO | WO 2004/073552 | 9/2004 |
| WO | WO 2004/098565 | 11/2004 |
| WO | WO 2005/110362 | 11/2005 |
| WO | WO 2005/117780 | 12/2005 |
| WO | WO 2006/014434 | 2/2006 |
| WO | WO 2007/084582 | 7/2007 |
| WO | WO 2007/087061 | 8/2007 |
| WO | WO 2007/115259 | 10/2007 |
| WO | WO 2008/005873 | 1/2008 |
| WO | WO 2008/060359 | 5/2008 |
| WO | WO 2008/083118 | 7/2008 |
| WO | WO 2008/094989 | 8/2008 |
| WO | WO 2008/157614 | 12/2008 |
| WO | WO 2009/012406 | 1/2009 |
| WO | WO 2009/035562 | 3/2009 |
| WO | WO 2009/035571 | 3/2009 |
| WO | WO 2009/063222 | 5/2009 |
| WO | WO 2009/097468 | 8/2009 |
| WO | WO 2009/126569 | 10/2009 |
| WO | WO 2009/137085 | 11/2009 |
| WO | WO 2009/151543 | 12/2009 |
| WO | WO 2010/006053 | 1/2010 |
| WO | WO 2010/065970 | 6/2010 |
| WO | WO 2010/078063 | 7/2010 |
| WO | WO 2010/141729 | 12/2010 |
| WO | WO 2011/127064 | 10/2011 |
| WO | WO 2012/019136 | 2/2012 |
| WO | WO 2013/022801 | 2/2013 |
| WO | WO 2013/119843 | 8/2013 |
| WO | WO 2014/150292 | 9/2014 |
| WO | WO 2015/073571 | 5/2015 |
| WO | WO 2016/023116 | 2/2016 |
| WO | WO 2016/042163 | 3/2016 |
| WO | WO 2017/087713 | 5/2017 |
| WO | WO 2019/200336 | 10/2019 |
| WO | WO 2020/172615 | 8/2020 |
| WO | WO 2025/170932 | 8/2025 |

OTHER PUBLICATIONS

Bucciarelli, Patrice D., "Working Model is Next Step in Team's Long Journey to Commercial Product", Healthfirst, Business First of Louisville, louisville.bizjournals.com, Feb. 27, 2004.
Chen et al., "Implantable Unpowered Parylene MEMS Intraocular Pressure Sensor", Microtechnologies in Medicine and Biology, 2006 International Conference on Publication Date: May 9-12, 2006, 5pp., downloaded from http://ieeezxplore.ieee.org/xpl/freeabs_all.jsp?arnumber=4281361.
Emi et al., "Hydrostatic Pressure of the Suprachoroidal Space", Investigative Ophthalmology & Visual Science, vol. 30, No. 2, Feb. 1989 (pp. 233-239).
https://entokey.com/gonioscopy-2/ Uploaded Oct. 2016.
Jain et al., "Development of polyvinyl alcohol-gelatin membranes for antibiotic delivery in the eye", Drug Development and Industrial Pharmacy, 2011, Informa Healthcare USA, Inc., 12 pages.
Jordan et al., "A Novel Approach to Suprachoroidal Drainage for the Surgical Treatment of Intractable Glaucoma", J Glaucoma, vol. 15, No. 3, Jun. 2006, pp. 200-205.
Katuri et al., "Intraocular Pressure Monitoring Sensors", IEEE Sensors Journal, vol. 8, No. 1, Jan. 2008, 8 pp.
Katz, L. Jay, MD, "A Call for Innovative Operations for Glaucoma", Arch Ophthalmology, Mar. 2000, vol. 118, pp. 412-413.
McLaren et al., "Continuous Measurement of Intraocular Pressure in Rabbits by Telemetry," Investigative Ophthalmology & Visual Science, vol. 37, No. 6, pp. 966-975, May 1996.
Online encyclopedia article "Hyaluronan," section on "Medical Applications" accessed Monday, Sep. 27, 2010. http://en.wikipedia.org/wiki/Hyaluronic_acid.
Rizq, et al., "Intraocular Pressure measurement at the Chroid Surface: A Feasibility Study with Implications for Implantable Microsystems", Br J Ophthalmol 2001; 85:868-871, Jul. 2001.
Ianchulev et al., "Minimally Invasive Ab-Interno Suprachoroidal Device (CyPass) for IOP Control in Open-Angle Glaucoma," presented at the Annual Meeting of the American Academy of Ophthalmology Oct. 16-19, 2010, Chicago, IL.
Ianchulev, Chapter 3: Suprachoroidal Space as a Therapeutic Target, in J.R. Samples & I.I.K. Ahmed (eds.), Surgical Innovations in Glaucoma 33 (Springer Science+Business Media 2014).
Walter et al., "Development of a Completely Encapsulated Intraocular Pressure Sensor", Ophthalmic Res 2000; 32:278-284. Nov. 5, 1999.
Supplementary European Search Report in related European application No. 04779911.9, dated Jul. 18, 2007, 3 pp (GLAUKO.011QEP).
Office Action in related European application No. 04779911.9, dated Apr. 17, 2009, 4 pp. (GLAUKO.011QEP).
Office Action in corresponding EP Application No. 04779911.9 mailed Sep. 30, 2010, 4 pp (GLAUKO.011QEP).
Second Office Action in Chinese Application No. 201080032278.7 dated Nov. 15, 2014.
Office Action in European Application No. 18153863.8 dated Oct. 19, 2018.
Canadian Office Action for Application No. 2,901,476, dated Nov. 13, 2020, in 5 pages.
Examination Report in Australian application No. 2015266850, dated Feb. 12, 2019 (GLAUKO.214AU).
Examination Report in Australian Application No. 2020201236, dated Jul. 8, 2020 (GLAUKO.214AUD1).
Examination Report in Australian Application No. 2018229507, dated Oct. 2, 2019.
Extended Search Report in European Application No. 18183395.5 dated Nov. 14, 2018.
Extended Search Report in European Application No. 18153863.8 dated Jun. 5, 2018.
International Search Report and Written Opinion in PCT/US2011/061967 mailed Jun. 28, 2012.
International Search Report and Written Opinion in PCT/US2014/065283 mailed Feb. 18, 2015.
International Search Report and Written Opinion in PCT/US2016/049996 dated Dec. 16, 2016 (GLAUKO.217WO).
International Search Report and Written Opinion, PCT/US2017/028665, issued Jul. 31, 2017.
International Preliminary Report on Patentability in PCT/US2016/049996 dated Mar. 6, 2018 (GLAUKO.217WO).
International Preliminary Report on Patentability, PCT/US2017/028665, issued Oct. 23, 2018.
International Preliminary Report on Patentability in PCT/US2016/053570 dated Mar. 27, 2018 (GLAUKO.210WO2).

(56)       References Cited

OTHER PUBLICATIONS

Rejection Decision in Chinese Application No. 201610177795.2 mailed Jan. 9, 2019.

Rejection Decision in Japanese Application No. 2012-511975 dated Jan. 9, 2015.

Search Report in European Application No. 10778286.4 dated Dec. 8, 2017.

Examination Report in Japanese Application No. 2016-221183 dated Feb. 8, 2019.

Examination Report in Australian Application No. 2018229507 dated Mar. 20, 2019.

Office Action in Japanese Application No. 2018-211032 dated Nov. 6, 2019.

* cited by examiner

BIORESORBABLE OCULAR DRUG DELIVERY DEVICE

RELATED APPLICATIONS

This application is a continuation of the U.S. National Phase application Ser. No. 16/095,680 filed Oct. 22, 2018, under 35 U.S.C. § 371 of International Application No. PCT/US2017/028665, filed on Apr. 20, 2017, which claims the benefit of U.S. Provisional Application No. 62/325,378, filed Apr. 20, 2016 the entire contents of which is incorporated by reference herein.

BACKGROUND

This disclosure relates to implantable intraocular drug delivery devices structured to provide targeted and/or controlled release of a drug to a desired intraocular target tissue and methods of using such devices for the treatment of ocular diseases and disorders. In certain embodiments, this disclosure also relates particularly to a treatment of ocular diseases with drug delivery devices implanted within the eye wherein some or essentially the entire device is made of biodegradable materials.

The mammalian eye is a specialized sensory organ capable of light reception and is able to receive visual images. Numerous pathologies can compromise or entirely eliminate an individual's ability to perceive visual images, including trauma to the eye, infection, degeneration, vascular irregularities, and inflammatory problems. The central portion of the retina is known as the macula. The macula, which is responsible for central vision, fine visualization, and color differentiation, may be affected by age related macular degeneration (wet or dry), diabetic macular edema, idiopathic choroidal neovascularization, or high myopia macular degeneration, among other pathologies.

Other pathologies, such as abnormalities in intraocular pressure, can affect vision as well. About two percent of people in the United States have glaucoma, which is a group of eye diseases encompassing a broad spectrum of clinical presentations and etiologies but unified by increased intraocular pressure. Glaucoma causes pathological changes in the optic nerve, visible on the optic disk, and it causes corresponding visual field loss, which can result in blindness if untreated. Increased intraocular pressure is the only risk factor associated with glaucoma that can be treated, thus lowering intraocular pressure is the major treatment goal in all glaucomas, and can be achieved by drug therapy, surgical therapy, or combinations thereof.

Many pathologies of the eye progress due to difficulty in administering therapeutic agents to the eye in sufficient quantities and/or for the duration necessary to ameliorate symptoms of the pathology. Often, uptake and processing of the drug occurs prior to the drug reaching an ocular target site. Due to this metabolism, systemic administration may require undesirably high concentrations of the drug to reach therapeutic levels at an ocular target site. This cannot only be impractical or expensive, but may also result in a higher incidence of side effects. Topical administration is potentially limited by limited diffusion across the cornea, or dilution of a topically applied drug by tear-action. Even those drugs that cross the cornea may be unacceptably depleted from the eye by the flow of ocular fluids and transfer into the general circulation. Thus, a means for ocular administration of a therapeutic agent in a controlled and targeted fashion would address the limitations of other delivery routes.

SUMMARY

Various embodiments disclosed herein relate to a drug delivery ocular implant. The ocular implant includes an outer shell having a proximal end and a distal end, and the outer shell is shaped to define an interior lumen. A drug can be positioned within the interior chamber.

There is provided, in several embodiments, a drug delivery ocular implant or device comprising an elongate outer shell having a proximal end, a distal end, the outer shell being shaped to define an interior lumen, and at least a first drug positioned within the interior lumen, wherein the outer shell comprises a biodegradable polymer. The outer shell is preferably tubular or cylindrical in shape.

According the disclosure herein, any of the implants described may comprise a shell of biodegradable polymeric material, which includes homopolymers, polymer blends and copolymers, such as random copolymers and block copolymers.

Biodegradable materials suitable for making the implant and components thereof include, but are not limited to, the following: poly(esters), poly(ester amide) (PEA), poly(ester carbonate) (PEC), polylactide (PLA), poly(L-lactide) (PLLA), poly(D-lactide) (PDLA), poly(DL-lactic acid) (PDLLA), polyglycolide (PGA), polycaprolactone (PCL), copolymers such as polylactideco-glycolide (PLGA), poly (hydroxyalkanoate)s, poly(3-hydroxybutyrate) (PHB), PHB copolymerized with 3-hydroxyvalerate (PHBV), Poly(propylene fumarate) (PPF), poly-(acid anhydride) (PAA), poly (butylene succinate) (PBS), poly(ethylene succinate) (PES), poly(hydroxyalkanoate) (PHA), poly(cyanoacrylate) (PCA), polyacetals, polyorthoesters (POE), polycarbonates including poly(trimethylene carbonate) (PTMC), polyphosphazenes, polyphosphoesters, and blends, copolymers, and combinations of the foregoing; and natural polymers, including but not limited to, modified poly(saccharide)s, e.g., starch, cellulose, and chitosan.

In several embodiments, the device may have a length from 1-7 mm, including 2-5 mm. In some embodiments, the device has a tip that narrows near a distal end of the implant. In other embodiments, the device may have a length of about 15-30 mm, including about 15 to about 18 mm, about 18 to about 21 mm, about 21 to about 23 mm, about 23 to about 25 mm, about 25 mm to about 27 mm, about 27 to about 30 mm, and overlapping ranges thereof. In some embodiments, the outer shell of the device can be flexible and/or curved.

In several embodiments, an ocular implant can be implanted into the eye of a subject. The implant can include an elongate outer shell comprising a bioerodible material and shaped to define an interior lumen, an internal plug positioned within the interior lumen, the internal plug including a hydrogel; and a drug reservoir positioned within the interior lumen, the drug reservoir including a drug. The drug can pass through at least a portion of the internal plug to control elution of the drug through the outer shell.

In several embodiments, the drug reservoir is positioned adjacent to the internal plug. In several embodiments, the internal plug is positioned adjacent a distal-most end of the interior lumen. In several embodiments, the elongate outer shell comprises one or more orifices positioned near a distal end of the outer shell, wherein the orifices are configured to control elution of the drug through the hydrogel and out of the implant. In several embodiments, the implant includes a coating surrounding at least a portion of the outer shell.

In several embodiments, the implant includes a proximal barrier. The proximal barrier can form an end cap of a proximal end of the outer shell. In several embodiments, the proximal barrier is positioned within the outer shell near a proximal side of the drug reservoir.

In several embodiments, the outer shell is configured to begin to bioerode after all or substantially all of the drug is eluted from the interior lumen of the implant. In several embodiments, the outer shell is configured to begin to bioerode while at least a portion of the drug to be eluted from the interior lumen of the implant remains in the interior lumen. In several embodiments, the implant further comprises a fluid flow passageway. In several embodiments, the implant is configured for implantation within the eye of a subject, and wherein the fluid flow passageway drains ocular fluid to a physiological outflow space. In several embodiments, the hydrogel surrounds at least a portion of the drug within the interior lumen.

The ocular implant can include one or more retention features configured to secure or anchor the ocular implant in ocular tissue. Such retention protrusions optionally comprise one or more of ridges, ribs, and/or barbs. In some embodiments, the retention protrusions are flexible.

Implants provided for herein are optionally anchored (e.g., any mechanism or element that allows an implant to become affixed to, secured to or otherwise attached, either permanently or transiently) to a intraocular tissue, such as ciliary muscles, the ciliary tendons, the ciliary fibrous band, the trabecular meshwork, the iris, the iris root, the lens cortex, the lens epithelium, to or within the lens capsule, the sclera, the scleral spur, the choroid, or to or within Schlemm's canal.

The ocular implant may be configured to be positioned in the supraciliary space, suprachoroidal space, Schlemm's canal, anterior chamber, vitreous humor, or capsular bag. The ocular implant may be positioned in the supraciliary space, suprachoroidal space, Schlemm's canal, anterior chamber, vitreous humor, or capsular bag.

In several embodiments, the outer shell has a substantially uniform thickness. In several embodiments, the outer shell is permeable or semi-permeable to the drug contained within, thereby allowing at least about 5%, 10%, 15%, 20% or more of total the elution of the first drug to occur through the portions of the shell having the first thickness. In some embodiments, all or substantially all of the total elution of the drug occurs through the outer shell. In other embodiments, the outer shell is impermeable or substantially impermeable to the drug contained within the device, thereby allowing less than 5%, including less than 2%, less than 1% or substantially no elution occurs through the outer shell.

In some embodiments, the outer shell comprises one or more regions that differ in the rate drug release from the majority of the outer shell. Such regions may allow increased or decreased drug release as compared to the majority of the outer shell. Such regions may be characterized by, for example, the presence or absence of a coating that retards drug release, or being thinner or thicker so as to alter the rate of drug release. In those embodiments having regions of reduced shell thickness, such regions may be created by any suitable means, including one or more of ablation, stretching, etching, grinding, and molding. The region may be in any pattern on or around the implant, including a spiral pattern, patches, rings and/or bands.

In some embodiments, the wall of the outer shell contains at least one aperture, orifice or hole. In some embodiments, the wall of the outer shell contains a plurality of apertures, orifices or holes that may be positioned randomly or in a patterned array. Apertures, orifices or holes in the wall of the outer shell may be patent, or covered by one or more coatings or membranes. In some embodiments, where the device includes a plurality of apertures, orifices or holes through the outer shell, at least a portion of the plurality may occluded by a membrane permeable to a drug.

In several embodiments, elution of a drug (e.g., a protein therapeutic) is regulated by diffusion from the device through orifices (as discussed above) or other apertures, holes, channels, porosities, or preferably micro-porosities that are provided through the tube walls, or through caps or plugs or membranes at the ends of the tube. The diameter of such elution regulating features is configured to be sufficiently large to allow passage of protein drug molecules. In several embodiments, these features are at least about 0.05, about 0.1, about 0.15, about 0.2, about 0.25, about 0.3 micrometers (or larger) in diameter). In several embodiments, the thickness of the tube walls, caps, plugs, or membranes may range from about 10 micrometers to about 2 mm, for example about 10 micrometers to about 50 micrometers, about 50 to about 100 micrometers, about 100 to about 150 micrometers, about 150 to about 200 micrometers, and any range in between those listed. In some preferable embodiments, the range is between about 50 and about 200 micrometers.

In several embodiments, elution or diffusion of drug through the elution features (apertures, holes, channels, porosities, or preferably micro-porosities, etc.) generally follows the Fick Equation at any point in time, such that the elution rate is proportional to the concentration gradient from inside the device to outside the device. In several embodiments the combined open area of the elution features and the diffusion coefficient of the protein drug define the rate, in conjunction with the elution rate being inversely proportional to the length and tortuosity of the elution features.

The elution features may be formed by laser machining; or by extraction of highly soluble materials of suitable particle size blended into the bioresorbable matrix; or by sintering bioresorbable powder, depending on the embodiment.

The elution features are designed to provide an elution rate of protein drug, that, combined with the clearance rate from the eye, yields a therapeutic concentration of protein drug in the eye. Such an elution rate may range from about 0.1 to about 20 micrograms per week, including about 0.1 to about 20 micrograms, about 0.5 to about 20 micrograms, about 1.0 to about 20 micrograms, about 5.0 to about 20 micrograms, about 10.0 to about 20 micrograms, about 10.0 to about 15 micrograms, about 7 to about 15 micrograms, about 2 to about 10 micrograms, and preferably 2 to 6 micrograms per week. Other amounts between those ranges listed are also achieved, in several embodiments.

In several embodiments, the surface erosion of the bioresorbable material of the implant provides a self-cleansing function, such that adherent proteins, polysaccharides, cells, or other biomaterials may be sloughed off the device such that the elution features do not become blocked.

In some embodiments disclosed herein, there are provided coatings, preferably polymeric coatings that are biodegradable. In some embodiments, two or more polymeric coatings are positioned on a surface of the outer shell and, in some such embodiments, each coating has a unique rate of biodegradation in ocular fluid (including being substantially non-biodegradable). In some embodiments, the coating alters the rate of release of the drug (increasing or lessening) and/or alters the rate of biodegradation of the material covered by the coating (increasing or lessening).

Embodiments of the device may elute one or more drugs through the shell only, through one or more caps (including drug release elements) only, through one or more patent openings or perforations in the shell and/or cap membrane, or through any combination of the foregoing.

In several embodiments, at least the distal-most about 5 mm to about 10 mm of the interior lumen houses the drug.

In several embodiments, the elution of the first drug from the implant continues for at least a period of at least one year, including two years, three years, four years, five years, or longer.

Some embodiments provided for herein result in elution of drug from the implant with zero-order or pseudo zero-order kinetics.

In several embodiments, the implants as described herein optionally further comprise a lumen configured to transport ocular fluid from a first location in an eye to one or more other locations, thereby reducing intraocular pressure. In some such embodiments, the outer shell includes two lumens, which may be coaxial or side-by-side, wherein one lumen is the interior lumen for containing at least one drug and the other lumen serves as a conduit to facilitate the transmission of aqueous humor from the anterior chamber to another location in the eye, such as the suprachoroidal space or Schlemm's canal, such that the intraocular pressure is reduced.

In several embodiments, the device includes a cap structure for releasing or eluting one or more drugs. In some embodiments, the cap is a special type of cap referred to herein as a drug release element. The cap may be placed on either or both of the proximal or distal ends of the outer shell of the device. Several embodiments include one or two caps or drug release elements. Depending on the placement of the element(s), the device may deliver drug anteriorly, posteriorly, or both. Accordingly, the device may treat conditions of the anterior and/or posterior segments of the eye.

In several embodiments, the implant comprises a cap configured for reversible or irreversible interaction with the proximal end of the outer shell. The cap comprises at least one aperture, and in some embodiments a plurality of apertures are provided. The overall surface area of the one or more apertures can be selected in a particular embodiment, based on the desired rate of elution of the first drug from the implant.

In several embodiments, the placement of the cap over the proximal end of the outer shell enables the retention of the membrane between the cap and the proximal end of the outer shell. In some embodiments the cap is a press-fit cap, while other embodiments employ a crimp cap, screw cap or other type of cap. In several embodiments, the membrane is permeable to the at least a first drug as well as to ocular fluid (and/or the water component of ocular fluid). In several embodiments, the membrane (once the cap is positioned) occludes the at least one aperture, such that elution of the at least a first drug occurs only through the membrane (e.g., the compression of the membrane by the cap also functions to seal the implant to other routes of unintended drug release). In several embodiments, a distally positioned seal is placed within the lumen to limit the fluid communication between the interior lumen and the ocular space to that occurring through the membrane. In several embodiments, selected combinations of the membrane and the dimensions (e.g., surface area) of the aperture(s) are tailored to a specifically desired elution rate of the first active agent. In several embodiments, the membrane has a thickness of between about 50 and about 100 microns.

The ocular implant can include a special type of cap referred to herein as a drug release element that is configured to release the drug from the interior chamber, also referred to herein as the inner lumen or interior lumen. The drug release element can include a distal seal member that includes at least one opening, a proximal seal member that includes at least one opening, and a membrane compressed between the distal seal member and the proximal seal member. A retainer can be configured to retain the drug release element in place relative to the outer shell. The drug release element can be configured such that the drug passes through the at least one opening in the distal seal member, through the compressed membrane, through the at least one opening in the proximal seal member, and out the proximal end of the outer shell.

The retainer can include one or more tabs that can be folded to engage the proximal seal member. In some embodiments, the one or more tabs can be folded to engage the membrane. The outer shell can include one or more slots and the retainer can extend into the one or more slots and can be positioned proximally of the proximal seal member. The retainer can have a lateral length that is greater than an inner diameter of the interior chamber adjacent the retainer and that is less than or equal to an outer diameter of the outer shell adjacent the retainer. In some embodiments, the interior chamber can include a shelf, and the distal seal member can be seated against the shelf.

The membrane of the cap or drug release element can include ethylene vinyl acetate, which can have a concentration of vinyl acetate between about 10% and about 30%, although other concentrations can be used as discussed herein. Other membranes may be used, including those which are biodegradable. Membranes may also have biodegradable or nonbiodegradable coatings. The ocular implant can be configured such that the membrane in the compressed state has a thickness of between about 75 microns and about 125 microns and/or such that the membrane is compressed from an uncompressed state by an amount between about 20 microns and about 40 microns, although other thicknesses and amounts of compression can be used as discussed herein.

The drug release element can provide an elution rate between about 15 nanograms per day and about 35 nanograms per day, although other elution rates can be used. The ocular implant can be configured to hold a volume of the drug between about 40 nanoliters and about 150 nanoliters, although other volumes can be used.

In several embodiments, there is a valve within the outer shell wherein that is reversibly openable to enable passage of at least a first drug into the inner lumen. In some embodiments, there is a valve positioned at the distal-most end of the outer shell wherein the valve is reversibly openable to enable passage of at least a first drug from the interior lumen to a target site external to the implant.

Various embodiments of the implants disclosed herein may comprise one or more barriers placed within the interior lumen to limit anterior (or, in some embodiments, posterior) elution of the drug, and/or a barrier that comprises a one-way valve positioned to allow fluid passage through the implant in a proximal to distal direction. In some embodiments having one or more barriers placed within the interior lumen, the one or more barriers may facilitate the simultaneous (or sequential) elution of one or more drugs to the anterior and/or posterior chamber for targeted effects.

In several embodiments, the first drug is a beta-adrenergic receptor antagonist. The beta-adrenergic receptor antagonist may be either a selective beta-adrenergic antagonist, or a non-selective beta-adrenergic receptor antagonist. In several embodiments, the selective beta-adrenergic receptor antagonist is selected from the group consisting of betaxolol and levobetaxolol, and combinations thereof. In several embodiments the non-selective beta-adrenergic antagonist is selected from the group consisting of timolol, levobunolol, certeolol, and metipranolol, and combinations thereof. In several embodiments, at least one drug is used, and in some embodiments that at least one first drug is timolol.

In some embodiments, the drug can be formulated as an oil.

In some embodiments, the drug can include a prostaglandin, a prostaglandin analog, a prostaglandin inhibitor, a beta-adrenergic receptor antagonist, or combinations thereof, although other drugs can be used as discussed herein. In some embodiments, the drug can include travoprost and/or a prodrug thereof. In other embodiments, the drug includes alprostadil and/or a modified or prodrug form thereof.

Additionally, in several embodiments, a second agent may optionally be provided. In several embodiments, the second (or third, etc.) agent results in synergistic effects when combined with the first agent. In other embodiments, the second agent reduces one or more side effects associated with the first agent.

In some embodiments, one or more drugs are contained within a micelle or vesicular structure or compounded with a biodegradable polymer configured to release the drug at a known rate.

In several embodiments, the first drug is present as one or more micro-tablets, wherein the micro-tablets have a density of about 0.7 g/cc to about 1.6 g/cc, an aspect ratio of length to diameter of about 2.8 to 3.6, and/or minor axis of about 0.28 to 0.31 mm and a major axis of about 0.8 to 1.1 mm. In several embodiments, the first drug is present in an amount of at least 70% by weight of a total weight of the one or more micro-tablets. In several embodiments, the micro-tablets have a surface area to volume ratio of about 13 to 17. In several embodiments, the micro-tablets have dimensions allowing passage of the micro-tablets through a conduit having an inner diameter of about 23 to 25 gauge.

In further embodiments, the micro-tablets are optionally coated with a coating that regulates the release of the first drug from the micro-tablet. In some embodiments, the coating is a polymeric coating.

There is also provided herein methods for treating an ocular condition or disorder in an intraocular target tissue comprising making an opening in the temporal portion of an eye to access an anterior chamber of the eye, advancing a delivery device associated with a drug delivery ocular implant through the opening and across the anterior chamber of the eye, inserting the drug delivery ocular implant into eye tissue, positioning the implant at a desired location in the eye, and withdrawing the delivery device from the eye, wherein the drug elutes from the implant in sufficient quantity to treat an ocular condition or disorder. In some embodiments, a therapeutic effect is achieved for a period of at least one year up to five years.

In some embodiments, the device is positioned such that at least one of the one or more regions of drug release or a cap structure are located proximate an intraocular target. In several embodiments, the intraocular target is in the posterior chamber of the eye. In some embodiments, the intraocular target is selected from the group consisting of the macula, the retina, the optic nerve, the ciliary body, and the intraocular vasculature. In several other embodiments, the intraocular target is in the anterior chamber of the eye.

In several embodiments, inserting the drug delivery ocular implant into eye tissue comprises placing at least a portion of the implant in a portion of the eye selected from the group consisting of uveoscleral outflow pathway, suprachoroidal space, anterior chamber, capsular bag, vitreous humor, and Schlemm's canal.

BRIEF DESCRIPTION OF THE DRAWINGS

These and other features, aspects, and advantages of the present disclosure will now be described with reference to the drawings of embodiments, which embodiments are intended to illustrate and not to limit the disclosure. One of ordinary skill in the art would readily appreciated that the features depicted in the illustrative embodiments are capable of combination in manners that are not explicitly depicted, but are both envisioned and disclosed herein.

FIG. 21A depicts changes in drug concentration over time and 21B depicts changes in drug elution rate over time from a prophetic implant.

FIG. 22A depicts change in drug elution rate over time from an implant. FIG. 22B depicts change in drug elution rate over time from an implant.

DETAILED DESCRIPTION

Figure 1:
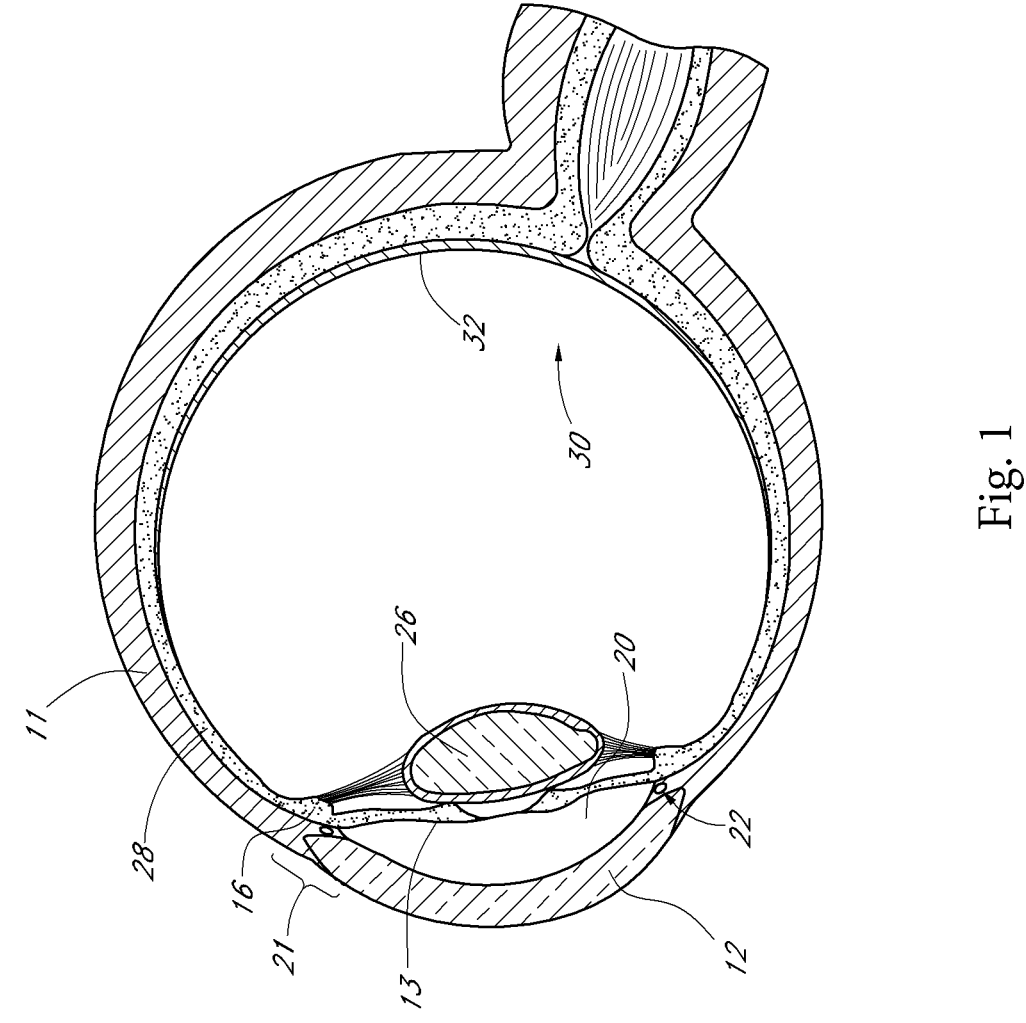
FIG. 1 illustrates a schematic cross sectional view of an eye.

FIG. 1 illustrates the anatomy of an eye, which includes the sclera 11, which joins the cornea 12 at the limbus 21, the iris 13 and the anterior chamber 20 between the iris 13 and the cornea 12. The eye also includes the lens 26 disposed behind the iris 13, the ciliary body 16 and Schlemm's canal 22. The eye also includes a uveoscleral outflow pathway, which functions to remove a portion of fluid from the anterior chamber and which includes a suprachoroidal or supraciliary space positioned between the choroid 28 and the sclera 11. The eye also includes the posterior region 30 including the macula 32.

Achieving local ocular administration of a drug may require direct injection or application, but could also include the use of a drug eluting implant, a portion of which, could be positioned in close proximity to the target site of action within the eye or within the chamber of the eye where the target site is located (e.g., anterior chamber, posterior chamber, or both simultaneously). Use of a drug eluting implant could also allow the targeted delivery of a drug to a specific ocular tissue, such as, for example, the macula, the retina, the ciliary body, the optic nerve, or the vascular supply to certain regions of the eye. Use of a drug eluting implant could also provide the opportunity to administer a controlled amount of drug for a desired amount of time, depending on the pathology. For instance, some pathologies may require drugs to be released at a constant rate for just a few days, others may require drug release at a constant rate for up to several months, still others may need periodic or varied release rates over time, and even others may require periods of no release (e.g., a "drug holiday").

In some instances, implants may serve additional functions once the delivery of the drug is complete such as maintaining the patency of a fluid flow passageway within an ocular cavity, functioning as a reservoir for future administration of the same or a different therapeutic agent, or may also function to maintain the patency of a fluid flow pathway or passageway from a first location to a second location, e.g. function as a stent. Conversely, it may be desirable that the implant be partially or completely biodegradable so that it is eliminated from the eye following delivery of all or almost all of the drug.

For bioresorbable drug delivery of protein drugs, such as Anti-VEGF proteins, and/or monoclonal antibody or antibody fragment, among other drugs, various methods exist, for example protein molecules blended with bioresorbable polymer, such as PLA, PLGA, Polyvinyl Alcohols (PVA), Crosslinked Polyacrylic Acids (Carbopols), and Hydroxypropyl Methylcelluloses (HPMC), and other polyesters or polyetheramides. Various configurations have previously been disclosed, including rods, gels, micelles, nanoparticles, and combinations of these materials. Applicants have discovered that there are disadvantageous to these approaches due to, for example possible protein inactivation and aggregation when generating those formulations. Aggregation can be disadvantageous, for example, by inhibiting a desired elution profile that reduces the lifespan of the delivered protein drugs. Also, such approaches may not extend the residence time of the protein in the eye to a significant relative to clearance rate of the protein alone.

In several embodiments disclosed herein, however, the bioresorbable (e.g., biodegradable or bioeridable) devices address such limitations. In several embodiments, the bioresorbable material used to construct all (or substantially all, or a portion of) the device may comprise PLA, PLGA, poly caprolactone, other polyester, polyetheramide, or other polyamide. Combinations may also be used in several embodiments. The bioresorbable material may be a hydrogel, comprising one or more of polyethylene glycol, polyethylene oxide, polyethylene oxide-co-propylene oxide, co-polyethylene oxide block or random copolymers, polyacrylamide, and polyvinyl alcohol, poly (vinyl pyrrolidinone). The hydrogel can instead or in addition, comprise one or more polymers such as hydroxypropylmethylcelulose, hydroxypropylcellulose, hydroxyethylcellulose, ethylhydroxyethylcellulose, polyvinyl acetate, polyvinyl alcohol, gelatin, and polyvinylpyrrolidone. Such polymers can, for example, form an interprentrating network. In some embodiments, the polymers can help to increase the mechanical strength of the hydrogel. In some embodiments, a particular polymer can be selected to adjust the permeability of the hydrogel. In some embodiments, the hydrogel is beneficially non-toxic, water-soluble, bioerodible, hydrophilic, highly absorbent and/or flexible. In some embodiments, the hydrogel can be optically clear to reduce or minimize interference with the patient's vision.

Hydrogels may be manufactured through various methods and can be implemented in various forms. In some embodiments, hydrogels can be formed from synthetic (e.g., poly (ethylene glycol), poly (hydroxyethyl methacrylate)) and/or naturally occurring polymers (e.g., collagen, hyaluronan, heparin). Depending on the reactivity of the constituent materials, gelation can be induced using pH, temperature, coulombic interactions, covalent bonding, non-covalent interactions, and/or polymerization, among other methods. Covalent bonding and/or polymerization, for example, may be accomplished by chemical reactions, such as free radical polymerization of vinyl groups; amide bond formation between amine and ester groups (such as active esters utilizing n-hydroxy succinimide); and/or Diels-Alder reaction between furan and maleimide moieties. The reaction components may be delivered into molds or tubes. For example, the hydrogel can form with the shape of the mold (e.g. a shape of the tube). In some embodiments, the hydrogel can be removed from the molds and/or extruded from the tubes. In some embodiments, the hydrogel can be transferred into the outer shell of the implant. In some embodiments, the reaction components can be delivered directly into the outer shell. For example, the hydrogel can form within the outer shell.

In some embodiments, the hydrogel can form a coating material that covers the implant (wholly or partially) and/or any orifice(s) (wholly or partially). In some embodiments, as discussed in more detail below, the implant can include a plug of hydrogel. For example, the drug can pass through the hydrogel. In some embodiments, the hydrogel can be formed in vitro or in situ. In some embodiments, the drug is embedded in the hydrogel. For example a hydrogel-drug mixture can include individual solutions of polymers and protein stabilizers. The hydrogel composition can be selected based on a number of factors, such as cross-link density (e.g., ratio of the mass of a cross-linker to the mass of a selected monomer), porosity, thickness, tortuosity, volume fraction of polymer in the hydrogel, and/or a diffusive permeability of the protein drug.

Some examples of protein stabilizers can include gelatins, sugars (e.g., trehalose, sucrose, among others), amino acids, non-ionic surfactants (e.g., Poloxamers), and/or buffer salts, among others. The protein stabilizers can advantageously prevent and/or limit aggregation and degradation of the protein drugs. This can improve the lifespan of the protein drug, as described above. Various formulations can be created by mixing the individual solutions of the polymers and protein stabilizers. Anti-VEGF drug ingredients and/or proteins, for example, can be added to the formulations and the protein drug molecules can be embedded in the polymer hydrogel matrices.

Example formulations comprising embedded protein drug molecules can be lyophilized. In some embodiments, the lyophilized materials may be directly compressed into tablets of sizes suitable for injection into vitreous chamber of human eye as soluble implants. For example, the tablets may be generally shaped as one or more cylindrical, and/or rectangular discs and/or tiles. The compression force applied to the lyophilized materials, including the formulations described herein, can be controlled or adjusted. Beneficially, the density of the tablets can be controlled by adjusting the applied compression force. Since dissolution rate of a tablet, for example, can be related to its density, dissolution rate of the tablets can be controlled by adjusting the compression force. For example, the compression force can translate to controlled release rate of the protein drug molecules.

In several embodiments, implants can be injected by a specially designed inserter. In some embodiments, the one or more tablets may be placed in a reservoir comprising elution controlling membrane or gel material to control the dissolution and diffusion rates and/or to contain the material delivered into the eye. Advantageously, this can minimize the impact on the visual field. The implant, once injected, can slowly dissolve in the uveoscleral outflow pathway, suprachoroidal space, anterior chamber, capsular bag, vitreous humor, and/or Schlemm's canal, for example. The implant gradually releases the protein drugs at concentrations that can provide therapy to the patient. In some embodiments, the concentration of protein drugs can optionally be in the range of about 100 to about 150 mg/mL, about 150 to about 200 mg/mL, about 200 to about 250 mg/mL, about 250 to about 300 mg/mL, about 300 to about 350 mg/mL, about 350 to about 400 mg/mL, about 400 to about 450 mg/mL, about 450 to about 500 mg/mL, and/or concentrations in between those listed. In some preferred embodiments, the concentration ranges from about 200 to about 300 mg/mL. The release rate can be for an extended duration, for example for 1 to 2 hours, 2 to 6 hours, 6 to 12 hours, 12 to 24 hours, 1 to 2 days, 1 to 7 days, 1 to 2 months, 1 to 6 months, 6 to 12 months, and/or 12 to 24 months or longer. The implant may be used to treat various posterior ocular diseases, such as age related macular degeneration, diabetic macular edema, and/or diabetic retinopathy, among other diseases.

In several embodiments, hybrid configurations comprising both bioresorbable and non-bioresorbable materials are employed for the delivery device. In several embodiments, possible non-bioresorbable component include, but are not limited to, a fritted material of steel, titanium, or non-bioresorbable polymer. In several embodiments, the non-bioresorbable material could form the tubular portion of the device, or the end cap, or membrane, as discussed structurally in more detail below. In such embodiments, the bioresorbable material could optionally form the remaining portions of the device.

As discussed in more detail below, several embodiments of the present invention provides near zero order elution of protein drug for an extended time period, while utilizing a bioresorbable shell such that a patient can receive multiple doses in series without accumulating a large amount of debris in the eye.

Implants according to the embodiments disclosed herein preferably do not require an osmotic or ionic gradient to release the drug(s), are implanted with a device that minimizes trauma to the healthy tissues of the eye which thereby reduces ocular morbidity, and/or may be used to deliver one or more drugs in a targeted and controlled release fashion to treat multiple ocular pathologies or a single pathology and its symptoms. However, in certain embodiments, an osmotic or ionic gradient is used to initiate, control (in whole or in part), or adjust the release of a drug (or drugs) from an implant. In some embodiments, osmotic pressure is balanced between the interior portion(s) of the implant and the ocular fluid, resulting in no appreciable gradient (either osmotic or ionic). In such embodiments, variable amounts of solute are added to the drug within the device in order to balance the pressures.

As used herein, "drug" refers generally to one or more drugs that may be administered alone, in combination and/or compounded with one or more pharmaceutically acceptable excipients (e.g. binders, disintegrants, fillers, diluents, lubricants, drug release control polymers or other agents, etc.), auxiliary agents or compounds as may be housed within the implants as described herein. The term "drug" is a broad term that may be used interchangeably with "therapeutic agent" and "pharmaceutical" or "pharmacological agent" and includes not only so-called small molecule drugs, but also macromolecular drugs, and biologics, including but not limited to proteins, nucleic acids, antibodies and the like, regardless of whether such drug is natural, synthetic, or recombinant. Drug may refer to the drug alone or in combination with the excipients described above. "Drug" may also refer to an active pharmaceutical agent or a prodrug or salt or derivative thereof.

As used herein, "patient" shall be given its ordinary meaning and shall also refer to mammals generally. The term "mammal", in turn, includes, but is not limited to, humans, dogs, cats, rabbits, rodents, swine, ovine, and primates, among others. Additionally, throughout the specification ranges of values are given along with lists of values for a particular parameter. In these instances, it should be noted that such disclosure includes not only the values listed, but also ranges of values that include whole and fractional values between any two of the listed values.

As used herein, "biodegradable" refers generally to the property of materials to be broken down and generally eliminated from the place of implantation following their implantation into the human or animal body by any natural process occurring therein. Biodegradable includes, but is not limited to, bioerodible, bioresorbable, and bioabsorbable.

In several embodiments, a biocompatible drug delivery ocular implant is provided that comprises an outer shell that is shaped to define at least one interior lumen that houses a drug for release into an ocular space. The outer shell is polymeric in some embodiments, and in certain embodiments is substantially uniform in thickness. The outer shell is preferably elongate and tubular or cylindrical in shape. In several embodiments, a cap is placed on one or both ends of the outer shell that serve to regulate drug delivery in whole or in part. The outer shell may contain one or more holes or apertures and/or regions of increased or reduced thickness so as to alter or tailor the rate of drug delivery from the implant.

In some embodiments, a layer or layers of a coating material is used to cover the implant (wholly or partially) and any orifice(s) (wholly or partially), thereby allowing further control of the rate of drug release from the implant. For example, in some embodiments, a hydrogel, as described above can form a layer or layers of a coating material that covers the implant (wholly or partially) and/or any orifice(s) (wholly or partially), to further control the rate of drug release from the implant. In some examples, the hydrogel forms a layer of a coating material along an inner wall of the implant. In some embodiments, the hydrogel forms a membrane through which the drug must pass to elute. In some embodiments, multiple layers of the coating material may be used to further control the rate of drug release from the implant. Each layer of the coating material can allow the drug to diffuse through each layer at varying rates. Additionally, in some embodiments, combinations of one or more orifices, a layer or layers covering the one or more orifices, and areas of reduced thicknesses are used to tailor the rate of drug release from the implant.

In some embodiments, the wall of the outer shell contains at least one aperture, orifice or hole. In some embodiments, the wall of the outer shell contains a plurality of apertures, orifices or holes that may be positioned randomly or in a patterned array. Apertures, orifices or holes in the wall of the outer shell may be patent, or covered by one or more coatings or membranes. In some embodiments, where the device includes a plurality of apertures, orifices or holes through the outer shell, at least a portion of the plurality may occluded by a membrane permeable to a drug.

In several embodiments, elution of a drug (e.g., a protein therapeutic) is regulated by diffusion from the device through orifices (as discussed above) or other apertures, holes, channels, porosities, or preferably micro-porosities that are provided through the tube walls, or through caps or plugs or membranes at the ends of the tube. The diameter of such elution regulating features is configured to be sufficiently large to allow passage of protein drug molecules. In several embodiments, these features are at least about 0.05, about 0.1, about 0.15, about 0.2, about 0.25, about 0.3 micrometers (or larger) in diameter).

In some embodiments, the orifices and/or elution holes can be tapered. Thus, the diameter of the orifice may not be constant. Tapered orifices can regulate and/or adjust elution of the drug (e.g., a protein therapeutic) by the extent of the taper of the orifice. In some embodiments, the taper of the orifice forms a cone-like shape. In some examples, the orifices can be tapered from the inner wall of the outer shell outwardly towards the outer wall of the outer shell. For example, the tapered orifice can have an inner diameter disposed along an inner wall of the outer shell and an outer diameter disposed along an outer wall of the outer shell. The inner diameter of the orifice can have a diameter of about 0.025, about 0.05, about 0.1, about 0.15, about 0.2, about 0.25, about 0.3 micrometers (or larger). The outer diameter of the orifice can have a diameter of about 0.025, about 0.05, about 0.1, about 0.15, about 0.2, about 0.25, about 0.3 micrometers (or larger).

The inner diameter may be smaller than the outer diameter of the orifice. For example, the taper of the orifice can extend radially outward from the inner diameter to the outer diameter. In some embodiments, the following equation can be used to determine a taper angle of the tapered orifice:

$$\tan\theta = \frac{R_{max} - R_{min}}{l}$$

In some embodiments, the value of tan 0 can range from approximately 0 to 1.73. In some embodiments, the taper angle can include an angle of about 0 to 5, about 5 to 10, about 10 to 15, about 15 to 20, about 20 to 25, about 25 to 30, about 30 to 35, about 35 to 40, about 40 to 45, about 45 to 50, about 50 to 55, about 55 to 60, and/or about 60 to 65 degrees relative to an axis extending from a proximal end of the implant to a distal end. This configuration can control the elution rate of the drug once the implant is implanted in the eye. For example, the amount of drug eluted from the implant can be more effectively controlled by adjusting the inner and/or outer diameter of the orifice and/or the taper angle. In some examples, if the taper angle is larger, the drug will elute at a faster rate than if the taper angle was smaller. The size of the inner diameter of the orifice and the outer diameter of the orifice can be selected based on a flux or elution rate of the drug as the drug passes through the tapered orifice. In several embodiments, the elution or diffusion of drug through the tapered orifices generally follows a modified Fick Equation at any point in time, as shown below, such that the ratio of the flux through a tapered orifice is a multiple of the ratio of the flux through an orifice having a constant diameter:

$$J_{tapered} = \frac{D\pi \; R_{max}R_{min}\Delta C}{l}$$

Following implantation at the desired site within the eye, drug is released from the implant in a targeted and controlled fashion, based on the design of the various aspects of the implant, preferably for an extended period of time. The implant and associated methods disclosed herein may be used in the treatment of pathologies requiring drug administration to the posterior chamber of the eye, the anterior chamber of the eye, or to specific tissues within the eye, such as the macula, the ciliary body or other ocular target tissues. In several embodiments, the implants are configured for placement in the punctum of an eye of a subject, in order to deliver one or more therapeutic agents. In several embodiments, the implant is placed in the punctum to deliver a therapeutic agent(s) to the tear film to target the cornea or anterior chamber and/or other ocular and/or orbital regions.

General

In some embodiments functioning as a drug delivery device alone, the implant is configured to deliver one or more drugs to anterior region of the eye in a controlled fashion while in other embodiments the implant is configured to deliver one or more drugs to the posterior region of the eye in a controlled fashion. In still other embodiments, the implant is configured to simultaneously deliver drugs to both the anterior and posterior region of the eye in a controlled fashion. In yet other embodiments, the configuration of the implant is such that drug is released in a targeted fashion to a particular intraocular tissue, for example, the macula or the ciliary body. In certain embodiments, the implant delivers drug to the ciliary processes and/or the posterior chamber. In certain other embodiments, the implant delivers drug to one or more of the ciliary muscles and/or tendons (or the fibrous band). In some embodiments, implants deliver drug to one or more of Schlemm's canal, the trabecular meshwork, the episcleral veins, the lens cortex, the lens epithelium, the lens capsule, the sclera, the scleral spur, the vitreous humor, the choroid, the suprachoroidal space, retinal arteries and veins, the optic disc, the central retinal vein, the optic nerve, the macula, the fovea, and/or the retina. In still other embodiments, the delivery of drug from the implant is directed to an ocular chamber generally. In several embodiments, the implants are configured to be placed in the punctum to deliver one or more therapeutic agents (which can target the anterior chamber and/or other ocular regions); or placed in the punctum to deliver to the tear film to target the cornea or anterior chamber and/or other ocular and/or orbital regions. It will be appreciated that each of the embodiments described herein may target one or more of these regions, and may also optionally be combined with a shunt feature (described below).

In several embodiments, the implant comprises an outer shell. In some embodiments, the outer shell is tubular and/or elongate. In several embodiments, the shell is formed to have at least a first interior lumen. In certain embodiments, the lumen runs the entire length of the outer shell. In some embodiments, the lumen is subdivided. In those embodiments additionally functioning as a shunt, the shell may have one or more additional lumens within the portion of the device where at least one such lumen functions as a shunt.

In preferred embodiments, the outer shell is biodegradable. In further embodiments, one or more or all additional components of the device including, but not limited to, cap, membrane, clip, and sealing members, are also biodegradable.

Biodegradable materials suitable for making the implant and components thereof include, but are not limited to, the following: poly(esters), poly(ester amide) (PEA), poly(ester carbonate) (PEC), polylactide (PLA), poly(L-lactide) (PLLA), poly(D-lactide) (PDLA), poly(DL-lactic acid) (PDLLA), polyglycolide (PGA), poly(glycolideco-lactide) (PGALA), poly(glycolic acid-co-lactic acid); polycaprolactone (PCL), copolymers such as polylactideco-glycolide (PLGA), poly(hydroxyalkanoate)s, poly(3-hydroxybutyrate) (PHB), PHB copolymerized with 3-hydroxyvalerate (PHBV), Poly(propylene fumarate) (PPF), poly-(acid anhydride) (PAA), poly(butylene succinate) (PBS), poly(ethylene succinate) (PES), poly(hydroxyalkanoate) (PHA), poly (acyanoacrylate) (PCA), polyacetals, polyorthoesters (POE), polycarbonates including poly(trimethylene carbonate) (PTMC), polyphosphazenes, polyphosphoesters, and blends, copolymers, and combinations of the foregoing; and natural polymers, including but not limited to, modified poly(saccharide)s, e.g., starch, cellulose, and chitosan.

The degree, rate or timing of biodegradability may be altered or tailored for a specific application by any method or combination of methods. Reducing the time for biodegradation may be achieved by, for example: increasing the surface-to-volume ratio of the shell; decreasing the wall thickness; modifying the surface geometry by pitting, grooving, or roughening; including holes or pores in the shell; manufacturing the shell to be more highly porous; and choosing a more rapidly biodegrading material. Increasing the time for biodegradation may be achieved by, for example: decreasing the surface-to-volume ratio of the shell; increasing the wall thickness; manufacturing the outer shell so that the surface geometry is smooth; manufacturing the shell to be minimally or non-porous; adding an inner and/or outer coat of relatively slow-dissolving material; and choosing a material that biodegrades more slowly. The degree, rate or timing of biodegradability may be also be tailored based on the placement of the implant. For example, implants that are to be placed in the punctum of the eye, a certain rate of biodegradation of the implant may be desired. That rate may or may not differ from a desired rate of biodegradation of an implant configured to be positioned, for example within the eye (e.g., in the suprachoroidal space). Thus, while in several embodiments the biodegradation of a punctal implant upon delivery of all or substantially all of its therapeutic payload is desired, the rate can be specifically tailored to match that implant/patient, etc. Depending on the embodiment, bioerosion of the implant is tailored to begin after the delivery of all or substantially all of the drug payload. In some embodiments, bioerosion of the implant is tailored to begin at least in part overlapping with the elution of the drug.

In several embodiments, the drug (or drugs) is positioned within the interior lumen (or lumens) of the implant shell. In several embodiments, the drug is preferentially positioned within the more distal portion of the lumen. In some embodiments, the distal-most 15 mm of the implant lumen (or lumens) house the drug (or drugs) to be released. In some embodiments, the distal-most 10 mm, including 1, 2, 3, 4, 5, 6, 7, 8, and 9 mm of the interior lumen(s) house the drug to be released. In several embodiments, the drug is preferentially positioned within the more proximal portion of the lumen. In some embodiments, the drug is positioned generally evenly throughout the lumen.

In some embodiments, the drug diffuses through the shell and into the intraocular environment. In several embodiments, the outer shell material is permeable or semi-permeable to the drug (or drugs) positioned within the interior lumen, and therefore, at least some portion of the total elution of the drug occurs through the shell itself, in addition to that occurring through any regions of increased permeability, reduced thickness, orifices etc. In some embodiments, about 1% to about 50% of the elution of the drug occurs through the shell itself. In some embodiments, about 10% to about 40%, or about 20% to about 30% of the elution of the drug occurs through the shell itself. In some embodiments, about 5% to about 15%, about 10% to about 25%, about 15% to about 30%, about 20% to about 35%, about 25% to about 40%, about 30% to about 45%, or about 35% to about 50% of the elution of the drug occurs through the shell itself. In certain embodiments, about 1% to 15%, including, 2, 3, 4, 5, 6, 7, 8, 9, 10, 11, 12, 13, and 14% of the total elution of the drug (or drugs) occurs through the shell. The term "permeable" and related terms (e.g. "impermeable" or "semi permeable") are used herein to refer to a material being permeable to some degree (or not permeable) to one or more drugs or therapeutic agents and/or ocular fluids. The term "impermeable" does not necessarily mean that there is no elution or transmission of a drug through a material, instead such elution or other transmission is negligible or very slight, e.g. less than about 3% of the total elution, including less than about 2% and less than about 1%.

In some embodiments, the implant comprises a polymeric coating on the exterior surface of a shell. In other embodiments, the implant comprises a polymeric coating on the interior surface of a shell. In still other embodiments, polymeric coatings are on both the interior and exterior surfaces. In yet other embodiments, the polymeric coatings are biodegradable. Some embodiments comprise a non-polymeric coating (e.g. heparin) in place of, or in addition to the polymeric coatings. Additionally, in some embodiments, combinations of one or more orifices, a layer or layers covering the one or more orifices, and areas of reduced thicknesses are used to tailor the rate of drug release from the implant.

In some embodiments, the interior lumen containing the drug(s) are separated from the proximal portion of the implant by way of an proximal barrier within the interior lumen that prevents elution of the drug to the anterior portion of the eye. In some embodiments, the interior lumen(s) containing the drug(s) are separated from the proximal portion of the implant by way of a one way valve within the interior lumen that prevents elution of the drug to the anterior portion of the eye, but allows ocular fluid from the anterior portion of the eye to reach the interior lumen(s) containing the drug(s).

In some embodiments, the implant further comprises a proximal portion structured for recharging/refilling the implant with the same, or an additional therapeutic drug, multiple drugs, or adjuvant compound, or compounds.

In some embodiments comprising a shunt, the shunt portion, following implantation at an implantation site, drains fluid from an ocular chamber into a physiologic outflow space to reduce intraocular pressure. In some embodiments, the implant is dimensioned such that when either the proximal or distal end of the implant is at an implantation site near a tissue targeted for drug delivery, the outflow ports of the implant will drain ocular fluid to a remote region and/or a physiological outflow pathway. For example, the punctal implants disclosed herein (and also in U.S. Provisional Patent Application No. 62/054,833, filed Sep. 24, 2014, which is incorporated by reference herein in its entirety) may also include one or more drainage lumens that drain tear fluid to the nasolacrimal duct. Other implants disclosed herein may be configured to drain ocular fluid from the anterior chamber to, for example, the suprachoroidal space. Drainage is not included in some embodiments of punctal implants and is not included in some embodiments of implants for placement within the eye.

For example, in some embodiments, the implant is dimensioned such that, following implantation, the distal end of the implant is located sufficiently close to the macula that the drug delivered by the implant reaches the macula. In some embodiments incorporating a shunt feature, the implant is dimensioned such that when the distal end of the implant is positioned sufficiently near the macula, the proximal end of the implant extends into the anterior chamber of the eye. In those embodiments, outflow ports in the implant, described in more detail below, are positioned such that the aqueous humor will be drained into the uveoscleral outflow pathway or other physiological outflow pathway.

In still other embodiments, combination drug delivery-shunt implants may be positioned in any physiological location that necessitates simultaneous drug delivery and transport of fluid from a first physiologic site to a second site (which may be physiologic or external to a patient). In some embodiments, the shunt feature works in conjunction with the drug delivery function to potentiate the therapeutic effects of the delivered agent. In other embodiments, the therapeutic effects of the delivered agent may be associated with unwanted side effects, such as fluid accumulation or swelling. In some embodiments, the shunt feature functions ameliorate the side effects of the delivered agent. It shall be appreciated that the dimensions and features of the implants disclosed herein may be tailored to attain targeted and/or controlled delivery to various regions of the eye while still allowing communication with a physiological outflow pathway.

For example, in some embodiments, the implant is dimensioned such that following implantation the distal end of the implant is located in the suprachoroidal space and the proximal end of the implant is located in the anterior chamber of the eye. In several embodiments, the drug eluted from the implant elutes from the proximal end of the implant into the anterior chamber. In some embodiments incorporating a shunt feature, one or more outflow ports in the implant are positioned such that aqueous humor will drain into the uveoscleral pathway. In several embodiments, aqueous humor will drain from the anterior chamber to the suprachoroidal space.

The delivery instruments, described in more detail below, may be used to facilitate delivery and/or implantation of the drug delivery implant to the desired location of the eye. The delivery instrument may be used to place the implant into a desired position, such as the suprachoroidal space at any length up to and including near the macula, in a position extending from the anterior chamber to the suprachoroidal space, or any other intraocular region, by application of a continual implantation force, by tapping the implant into place using a distal portion of the delivery instrument, by actuation of a source of stored energy in the delivery instrument or by a combination of these methods. The design of the delivery instruments may take into account, for example, the angle of implantation and the location of the implant relative to an incision. For example, in some embodiments, the delivery instrument may have a fixed geometry, be shape-set, or actuated. In some embodiments, the delivery instrument may have adjunctive or ancillary functions, such as for example, injection of dye and/or viscoelastic fluid, dissection, or use as a guidewire. As used herein, the term "incision" shall be given its ordinary meaning and may also refer to a cut, opening, slit, notch, puncture or the like.

In certain embodiments the drug delivery implant may contain one or more drugs which may or may not be compounded with a biodegradable polymer or a biodegradable polymer and at least one additional agent.

Drug Delivery Implants

The present disclosure relates to ophthalmic drug delivery implants which, following implantation at an implantation site, provide controlled release of one or more drugs to a desired target region within the eye, the controlled release being for an extended period of time. Various embodiments of the implants are shown in the drawings and will be referred to herein, but it is to be understood that the invention is not limited to the illustrated embodiments, and that features of the illustrated embodiments may be interchanged and/or they may be replaced by or further comprise features disclosed herein, as is understood by those skilled in the art.

The outer shell of the implant may be manufactured by extrusion, drawing, injection molding, micromachining, laser machining, or any combination thereof. Other suitable manufacturing and assembly methods known in the art may also be used. In several embodiments, the outer shell is elongate and cylindrical or tubular in shape, and comprises at least one interior lumen. In some embodiments the interior lumen is defined by the outer shell and a partition. In some embodiments, the partition is impermeable, while in other embodiments the partition is permeable or semi-permeable. In some embodiments, the partition allows for the recharging of the implant with a new dose of drug(s). In several embodiments, the thickness of the outer shell is substantially uniform. In other embodiments the thickness varies in certain regions of the shell. Depending on the desired site of implantation within the eye, thicker regions of the outer shell are positioned where needed to maintain the structural integrity of the implant. In some embodiments, the implant is made of a flexible material.

In several embodiments, the outer shell also has one or more specific regions of drug release or enhanced drug release as compared to the rest of the outer shell. In some embodiments the regions of drug release are of reduced thickness compared to the adjacent and surrounding thickness of the outer shell. In some embodiments, the regions of reduced thickness are formed by one or more of ablation, stretching, etching, grinding, molding and other similar techniques that remove material from the outer shell. In other embodiments the regions of drug release are of a different thickness (e.g., some embodiments are thinner and other embodiments are thicker) as compared to the surrounding outer shell, but are manufactured with an increased permeability to one or more of the drug and ocular fluid. In still other embodiments, the outer shell is uniform or substantially uniform in thickness but constructed with materials that vary in permeability to ocular fluid and drugs within the lumen. As such, these embodiments have defined regions of drug release from the implant. The regions of drug release may be of any shape needed to accomplish sufficient delivery of the drug to a particular target tissue of the eye.

In some embodiments, the implant is self-trephinating. In some embodiments, the distal end of the implant is sufficiently pointed to pierce eye tissue such as the cornea, limbus or near the scleral spur of the eye. In other embodiments, the distal end is rounded, blunted or otherwise not sharply pointed yet suitable to perform a blunt dissection of two tissue planes or to penetrate certain internal ocular tissues, preferably atraumatically. In either case, the distal portion can be sufficiently blunt so as not to substantially penetrate scleral tissue of the eye.

In some embodiments, the implant incorporates fixation or retention features, such as flexible outwardly-extending extensions, for example, ridges, ribs, barbs, bumps, threads or projections which extend from the outer surface of the implant to inhibit migration of the implant from its implanted position. In some embodiments, inwardly extending features such as grooves help to retain the implant. Such features may extend the full outer circumference of the implant, or only for some portion of the outer circumference. The extensions may be separate pieces attached to the implant, may be formed integrally with the implant, or may added in a separate manufacturing step. The extensions may be located at the proximal or distal ends or regions of the implant, or both, to prevent extrusion or movement of the implant from its intended location in the eye. In several embodiments, the extensions are longitudinally spaced along the implant. Spacing between the extensions may be regular or irregular. The flexibility of the retention features may facilitate entry through the corneal incision, and also through the ciliary muscle attachment tissue or other tissues. In some embodiments, the surface irregularities function to prevent growth of host tissue into or onto the implant (e.g., fibrotic growth) that could, depending on the embodiment, reduce the efficiency of drug elution.

In some embodiments, the implant has an outer diameter that will permit the implant to fit within a 23-gauge needle during implantation. The implant can also have a diameter that is designed for insertion with larger needles. For example, the implant can also be delivered with 18-, 19-, or 20-gauge needles. In other embodiments, smaller gauge applicators, such as 23-gauge or smaller, are used. In some embodiments, the implant has a substantially constant cross-sectional shape through most of its length. Alternatively, the implant can have portions of reduced or enlarged cross-sectional size (e.g., diameter) along its length. In some embodiments, the distal end of the implant has a tapered portion, or a portion having a continually decreasing radial dimension with respect to the lumen axis along the length of the axis. The tapered portion preferably in some embodiments terminates with a smaller radial dimension at the distal end. During implantation, the tapered portion can operate to form, dilate, and/or increase the size of an incision or puncture created in the tissue. The tapered portion may have a diameter of about 30-gauge to about 23-gauge, and preferably about 25-gauge. As discussed herein, in several embodiments the device can be tubular shaped, such that it can be injected through a needle into the vitreous (though other shapes are used in several embodiments). The diameter of such tubular implants may range from between about 0.1 and about 0.8 mm, about 0.2 and about 0.8 mm, about 0.3 and about 0.8 mm, about 0.4 and about 0.8 mm, and preferably from about 0.3 to about 0.6 mm. In several embodiments, the device may range in length from about 1 to about 15 mm, including about 2 to about 15 mm, about 4 to about 15 mm, about 5 to about 15 mm, about 5 to about 14 mm, about 5 to about 13 mm, about 5 to about 12 mm, about 5 to about 11 mm, about 2 to about 11 mm, about 3 to about 11 mm, and preferably from 5 to 10 mm long. Ranges of diameters and lengths between those listed are also contemplated.

In some embodiments, the drug is formulated or compounded with additional compounds. In some embodiments the drug is in the form of a drug-containing pellet. Some embodiments of therapeutic agent or drug comprise a drug compounded with a polymer formulation. In certain embodiments, the polymer formulation comprises a poly (lactic-co-glycolic acid) or PLGA co-polymer or other biodegradable (e.g. bioerodible, bioresorbable) polymer.

While the drug is generally placed within the lumen of the implants described herein, it has been omitted most of the figures so as to allow clarity in the illustration of other features of the implants. It will be understood, however, that all embodiments herein optionally include one or more drugs.

In several embodiments, the implant further comprises a coating that may be positioned in various locations in or on the implant. In some embodiments, the coating is a polymeric coating. The coating is optionally biodegradable. Some other embodiments may comprise an implant made entirely of a biodegradable material, such that the entire implant is degraded over time. In some embodiments, the coating is placed over the entire implant (e.g., enveloping the implant) while in other embodiments only a portion of the implant is covered. In some embodiments, the coating is on the exterior surface of the implant. In some embodiments, the coating is placed on the luminal wall within the implant as an alternate or in addition to the outside of the implant or shell. Similarly, in some embodiments in which the coating is positioned inside the implant, the coating covers the entire inner surface of the lumen, while in other embodiments, only a portion of the inner surface is covered.

Several embodiments of the implant may also comprise a shunt in addition to functioning as a drug delivery device. The term "shunt" as used herein is a broad term, and is to be given its ordinary and customary meaning to a person of ordinary skill in the art (and it is not to be limited to a special or customized meaning), and refers without limitation to the portion of the implant defining one or more fluid passages for transport of fluid from a first, often undesired location, to one or more other locations. In some embodiments, the shunt can be configured to provide a fluid flow path for draining aqueous humor from the anterior chamber of an eye to an outflow pathway to reduce intraocular pressure.

The shunt portion of the implant can have an inflow portion and an outflow portion. The inflow portion or inlet may be disposed at or near the proximal end of the implant. The inlet may comprise one or more openings. The shunt outflow portion may be disposed at or near the distal end of the implant and may comprise one or more openings. In some implants, especially longer implants configured to extend to the macula or other structures in the posterior of the eye, the outflow portion may be in the middle section of the implant or in both the middle and distal sections. In some embodiments, when the implant is deployed, the inflow portion may be sized and configured to reside in the anterior chamber of the eye and the outflow portion may be sized and configured to reside in the supraciliary or suprachoroidal space. In some embodiments, the outflow portion may be sized and configured to reside in the supraciliary region of the uveoscleral outflow pathway, the suprachoroidal space, other part of the eye, or within other physiological spaces amenable to fluid deposition.

In some embodiments, at least one lumen extends through the shunt portion of the implant. In some embodiments, there is at least one lumen that operates to conduct the fluid through the shunt portion of the implant. In certain embodiments, each lumen extends from an inflow end to an outflow end along a lumen axis. In some embodiments the lumen extends substantially through the longitudinal center of the shunt such that it is coaxial with the drug lumen. In other embodiments, the lumen can be offset from the longitudinal center of the shunt such that it and the drug lumen are in a side-by-side configuration.

In some embodiments of implants, including implants that extend far into the posterior segment of the eye, the shunt portion of the implant and the drug delivery portion of the implant are separate, with the drug delivery portion being towards the distal end and the shunt portion being towards the proximal end. In such embodiments, the most proximal outflow orifice on the implant is positioned at the proximal end of the implant or within 10 mm from the proximal end. Outflow orifices may be positioned in any location distally of the inflow location(s). In some embodiments, the shunt portion and the drug portion overlap to some extent, and may have either a coaxial or side-by-side arrangement as discussed above.

Figure 2B:
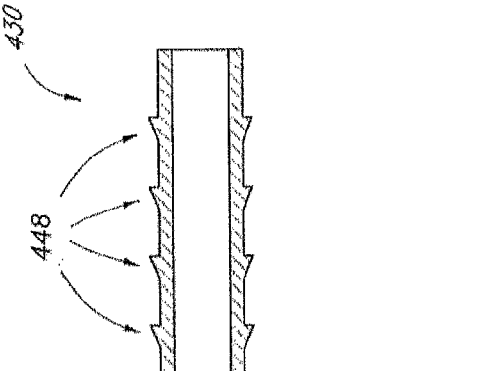
FIG. 2B illustrates a cross-sectional view of an embodiment of retention features disposed on a drug delivery implant in accordance with embodiments disclosed herein.
Figure 2A:
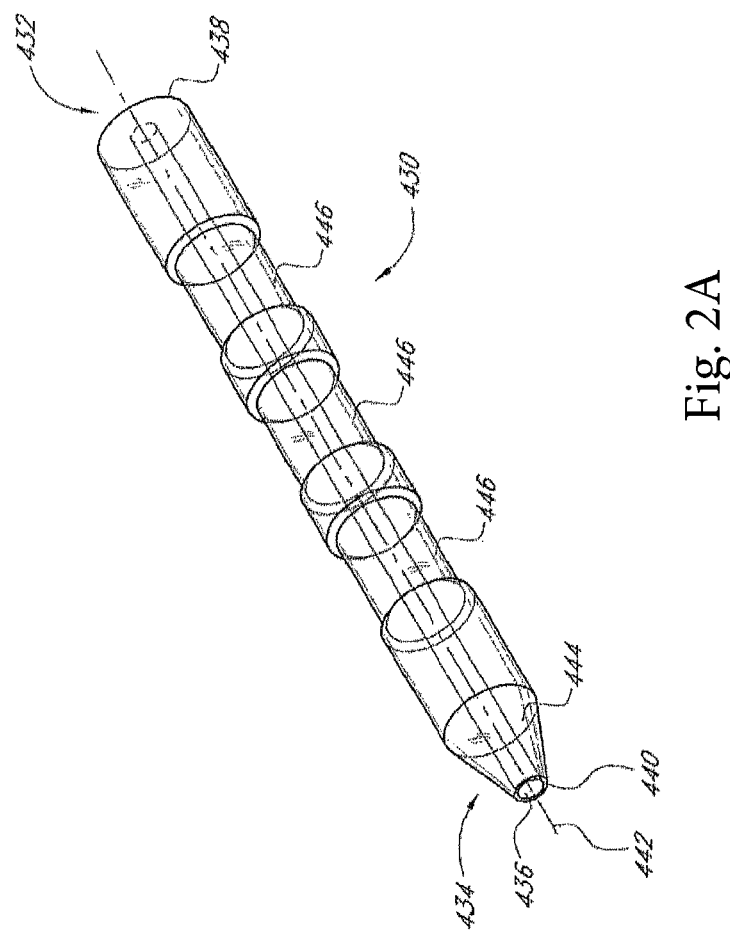
FIG. 2A illustrates a further drug delivery implant incorporating a shunt in accordance with embodiments disclosed herein.

FIG. 2A illustrates an embodiment of a drug eluting implant 430 comprising a coaxial shunt that is operable to drain fluid from the anterior chamber to a naturally-occurring outflow pathway such as the uveoscleral outflow pathway (e.g., the suprachoroidal space). The interior lumen 436 of the implant 430 can communicate with an inflow portion or inlet 432 and an outflow portion or outlet 434. The drug can lie in the space between the interior lumen and the outer shell. There may be a wall separating the drug and the drainage lumen, or they may be in contact with a solid drug or drug formulation forming the wall of the interior lumen. When implanted, the inflow portion 432 is sized and configured to reside in the anterior chamber of the eye and the outflow portion 434 is sized and configured to reside in the suprachoroidal space. The drug can elute from the inflow portion directly or through a cap (not illustrated), and/or through the wall of the implant. As the drug elutes from the implant, fluid can be conducted through the interior lumen 436 of the implant.

The implant 430 may be sized to have an outer diameter that will permit the implant 430 to fit within a 21-gauge or 23-gauge needle or hollow instrument during implantation; however, larger or smaller gauge instruments or other specialized delivery devices may also be used. The implant 430 can also have a diameter that is designed for delivery with larger needles. For example, the implant 430 can also be delivered with 18-, 19- or 20-gauge needles. The implant 430 can have a constant diameter through most of its length. In some embodiments, the implant 430 comprises retention features 446 that operate to mechanically lock or anchor the implant 430 in place when implanted. In some embodiments, the retention features 446 comprise portions of reduced diameter, e.g., annular grooves, between the proximal end 438 and the distal end 440. In some embodiments, the retention features 446 comprise barbs or other projections, which extend from the outer surface of the implant 430, to inhibit migration of the implant 430 from its implanted position, as described above.

As shown in FIG. 2B, for example, some embodiments of an implant 430 have a plurality of annular ribs 448 formed on an exterior surface of the implant 430. The annular ribs 448 can be spaced longitudinally along the implant 430 between the proximal end 438 and the distal end 440. Spacing between the annular ribs 448 can be regular or irregular.

The outflow portion 434 of the implant 430 preferably is disposed at or near the distal end 440 of the implant 430. In the embodiment illustrated in FIG. 2A, the outflow portion 434 is a tapered distal portion 444; however, it may also have other shapes including a non-tapering or more gently tapering shape. The tapered distal portion 444 terminates with a smaller radial dimension at the outflow end or outlet 440. During implantation, the tapered portion 444 can operate to form, dilate, and/or increase the size of, an incision or puncture created in the tissue, either alone or in cooperation with a guidewire, trocar, or portion of another delivery instrument placed in the interior lumen 436 that is flush or extends beyond the end of the implant. For example, the distal end 440 can operate as a trocar to puncture or create an incision in the tissue. Following advancement of the distal end 440 of the implant 430, the tapered portion 444 can be advanced through the puncture or incision. The tapered portion 444 will operate to stretch or expand the tissue around the puncture or incision to accommodate the increasing size of the tapered portion 444 as it is advanced through the tissue. Some embodiments of implants (for placement within the eye or within the punctum) do not include drainage.

The tapered portion 444 can also facilitate proper location of the implant 430 into the supraciliary or suprachoroidal spaces. For example, the implant 430 is preferably advanced through the tissue within the anterior chamber angle during implantation. This tissue typically is fibrous or porous, which is relatively easy to pierce or cut with a surgical device, such as the tip of the implant 430. The implant 430 can be advanced through this tissue and abut against the sclera once the implant 430 extends into the uveoscleral outflow pathway. As the implant 430 abuts against the sclera, the tapered portion 444 preferably provides a generally rounded edge or surface that facilitates sliding of the implant 430 within the suprachoroidal space along the interior wall of the sclera. For example, as the implant 430 is advanced into the uveoscleral outflow pathway and against the sclera, the implant 430 will likely be oriented at an angle with respect to the interior wall of the sclera. As the tip of the implant 430 engages the sclera, the tip preferably has a radius that will permit the implant 430 to slide along the sclera instead of piercing or substantially penetrating the sclera. As the implant 430 slides along the sclera, the tapered portion 444 will provide an edge against which the implant 430 can abut against the sclera and reduce the likelihood that the implant 430 will pierce the sclera.

For the sake of clarity, only a small number of the possible embodiments of the various retention projections have been shown. It should be understood that any implant embodiment may be readily combined with any of the retention projections disclosed herein.

FIGS. 3A-3D illustrate examples of an implant. The implant can include identical or similar features as other implants described herein. As discussed above, the implant can include an outer shell 54. The outer shell 54 can include one or more orifices. For example, in several embodiments one or more orifices 56a traversing the thickness of the outer shell 54 provide communication passages between the environment outside the implant and the interior lumen 58 of the implant (FIGS. 3A-3D). The one or more orifices are created through the implant shell by way of drilling through the various shells of a particular implant or any other technique known in the art. The orifices may be of any shape, such as spherical, cubical, ellipsoid, and/or the like. The number, location, size, and shape of the orifices created in a given implant determine the ratio of orifice to implant surface area. This ratio may be varied depending on the desired release profile of the drug to be delivered by a particular embodiment of the implant, as described below. In some embodiments, the orifice to implant surface area ratio is greater than about 1:100. In some embodiments, the orifice to implant surface area ratio ranges from about 1:10 to about 1:50, from about 1:30 to about 1:90, from about 1:20 to about 1:70, from about 1:30 to about 1:60, from about 1:40 to about 1:50. In some embodiments, the orifice to implant surface area ratio ranges from about 1:60 to about 1:100, including about 1:70, 1:80 and 1:90.

In some embodiments, the outer shell may contain one or more orifice(s) 56b in the distal tip of the implant or near a distal end of the implant, as shown in FIGS. 3A-3D, for example. The shape and size of the orifice(s) can be selected based on the desired elution profile. Still other embodiments comprise a combination of a distal orifice and multiple orifices placed more proximally on the outer shell. Additional embodiments comprise combinations of distal orifices, proximal orifices on the outer shell and/or regions of drug release as described above (and optionally one or more coatings). Additional embodiments have a closed distal end. In such embodiment the regions of drug release (based on thickness/permeability of the shell, orifices, coatings, placement of the drug, etc.) can be arranged along the long axis of the implant. Such configures are advantageous to reduce the amount of tissue damage caused by the advancing distal end that occurs during the several embodiments of the implantation procedures disclosed herein.

In some embodiments, the distal orifices comprise a biodegradable or bioerodible plug 61 with a plurality of orifice(s) 56b that maintain drug elution from the implant, should one or more orifices become plugged with tissue during the insertion/implantation. In other embodiments, the orifice(s) can comprise permeable or semi-permeable membranes, porous films or sheets, or the like. In some such embodiments, the permeable or semi-permeable membranes, films, or sheets may lie outside the shell and cover the orifices, inside the shell to cover the orifices or both. The permeability of the material will partially define the release rate of the drug from the implant, which is described in further detail below. Such membranes, sheets, or films are useful in those embodiments having elongated orifices in the outer shell.

In several embodiments, an additional structure or structures within the interior of the lumen can at least partially control elution of the drug from the implant. In addition to or instead of the layer or layers of permeable or semi-permeable material that may be used to envelope the drug discussed above, FIGS. 3A-3D depict the implant. The implant can have an outer shell, an internal plug 210, and a drug reservoir at least partially filled with a drug 62. In some embodiments, the internal plug 210 is positioned between the drug 62 and the various orifices 56a and 56b of the outer shell 54. For example, the internal plug 210 need not completely surround the drug. However, as discussed below, in some embodiments, the internal plug 210 at least partially or entirely surrounds the drug 62. In some embodiments, the material of the internal plug 210 differs from that of the shell 54, while in some embodiments the material of the internal plug 210 is the same material as that of the shell 54. Suitable materials for the internal plug include, but are not limited to, agarose or hydrogels, among others. As discussed above, hydrogels can comprises polyacrylamide, polymethyl methacrylate, HEMA (hydroxyethyl methacrylate), polyethylene glycol, polyethylene oxide, polyethylene oxide-co-propylene oxide, co-polyethylene oxide block or random copolymers, polyvinyl alcohol, poly (vinyl pyrrolidinone), hydroxypropylmethylcelulose, hydroxypropylcellulose, hydroxyethylcellulose, ethylhydroxyethylcellulose, polyvinyl acetate, gelatin, and/or polyvinylpyrrolidone, among others. Additional materials disclosed herein for use in the shell or other portion of the implant may be suitable for the internal plug, in certain embodiments.

In some embodiments, the size, density, porosity, or permeability of the hydrogel plug 210 may differ from that of the shell 54. In some embodiments, the hydrogel plug is formed in place (i.e. within the interior lumen of the implant), for example by polymerization, molding, or solidification in situ of a dispensed liquid, powder, crystal, or gel. In some embodiments, the hydrogel plug is preformed external to the shell and placed within the shell prior to implantation. In such embodiments, tailored implants can be constructed in that the selection of a pre-formed internal plug may be optimized based on a particular drug, patient, implant, and/or disease to be treated.

In some embodiments, the hydrogel plug can be dehydrated or in a partially shrunken/dehydrated state before being placed within the outer shell 54 prior to implantation. For example, in a dehydrated state, the hydrogel plug can shrink to as little as approximately 10% of its fully hydrated volume, while in other embodiments it is at 95%, 90%, 85%, 80%, or 75% of its fully hydrated volume in the implant. In some embodiments, the hydrogel can be hydrated and swell within the outer shell 54 prior to implantation and/or before being placed within the outer shell 54. In some embodiments, the hydrogel plug can include a "fugitive" material or solvent, such as a plasticizer or glycerin, among others that are biocompatible. The fugitive material flows out of the implant and is replaced by ocular fluids following implantation. The material can thus create a trigger for outflow and/or elution of the drug from the implant. For example, outflow of the material can allow the plug to become more permeable to the drug allow the drug to pass through the hydrogel plug. In some embodiments, the material can prevent and/or minimize shrinkage or collapsing of the drug before and/or during elution or while the implant is being stored and shipped prior to use.

As discussed above, in several embodiments, the hydrogel plug can be biodegradable or bioerodible. In some other embodiments, the hydrogel plug is durable (e.g., not biodegradable or bioerodible). In some embodiments, the hydrogel plug is beneficially non-toxic, water-soluble, bioerodible, hydrophilic, highly absorbent and/or flexible.

As shown in FIGS. 3A-3D, the hydrogel plug 210 can be positioned within the outer shell 54. In some embodiments, the hydrogel plug can be positioned adjacent the drug 62. The hydrogel plug 210 can be positioned adjacent a distalmost end of the outer shell 54. For example, the drug can be positioned adjacent the plug 210 and/or proximal to the plug 210. As discussed herein, the drug 62 can be partially or entirely surrounded by the hydrogel plug. In some embodiments, the plug 210 can include a mixture of hydrogel and drug.

Various amounts of hydrogel and drug can be implemented in certain embodiments of the implant. For example, the ratio of volume of drug to hydrogel positioned within the implant for elution is greater than about 1:1. In some embodiments, the ratio of volume of drug to hydrogel positioned within the implant for elution ranges from about 1:1 to about 2:1, about 2:1 to about 5:2, about 5:2 to about 3:1, about 3:1 to about 7:2, about 7:2 to about 4:1, about 4:1 to about 9:2, and/or other ranges. In some embodiments, the ratio of volume of drug to hydrogel positioned within the implant for elution ranges from about 1:1 to about 1:2, about 1:2 to about 1:3, about 1:3 to about 1:4, among other ranges. As discussed above, the drug can be dispersed within the hydrogel. In such configurations, the all or a portion of the drug can be dispersed within the hydrogel. For example, at least 50% of the volume of the mixture can include the drug, as discussed above.

In several embodiments, the internal plug may be closely fit or bonded to the inner wall of shell. For example, the hydrogel plug is preferably permeable to the drug, thereby allowing passage of the drug through the plug, through the orifices and to the target tissue. In some embodiments, the hydrogel plug is also permeable to body fluids, such that fluids from outside the implant may reach the drug. The overall release rate of drug from the device may be controlled by the physical characteristics of several aspects of the implant components, including, but not limited to, the area and volume of the orifices, the surface area of any regions of drug release, the composition and/or size or position of the hydrogel plug with respect to both the drug and the orifices and/or regions of drug release, and the permeability of the hydrogel plug to the drug and bodily fluids. In addition, in several embodiments, the hydrogel plug increases path length between the drug and the orifices and/or regions of drug release, thereby providing an additional point of control for the release rate of drug. For example, the drug can be configured to pass through all and/or a portion of the hydrogel plug 210 to the target tissue. Elution of the drug through the hydrogel can occur over a period of two weeks to one year. In some embodiments, elution of the drug through the hydrogel can occur over a period of two weeks to three years, one day to one week, one week to two weeks, two to four weeks, one month to two months, two months to four months, four months to eight months, four to six months, six months to one year, one year to two years, two years to three years, and/or longer periods of time.

In several other embodiments, the hydrogel plug 210 may be more loosely fit into the interior lumen of the shell which may allow flow or transport of the drug around the plug. (See FIG. 3B) In still other embodiments, the hydrogel plug may comprise two or more pieces or fragments. In some embodiments, the drug may elute from the implant by passing through the gap between the hydrogel plug and the interior wall of shell. The drug may also elute from the implant by passing through the gaps between pieces or fragments of the hydrogel plug. The drug may also elute from the implant by passing through the permeable inner plug. Similarly, bodily fluids may pass from the external portion of the implant into the implant and reach the drug by any of these, or other, pathways. Elution of the drug can occur as a result of a combination of any of these routes of passage or permeability.

Figure 3A:
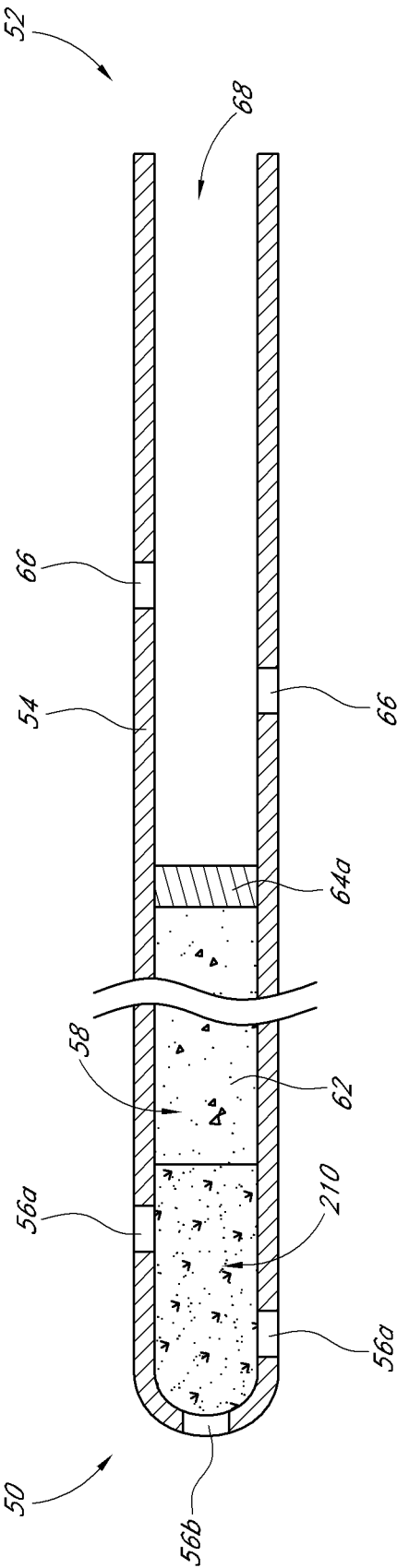
FIGS. 3A-3D illustrate various drug delivery implants in accordance with embodiments disclosed herein.
Figure 3B:
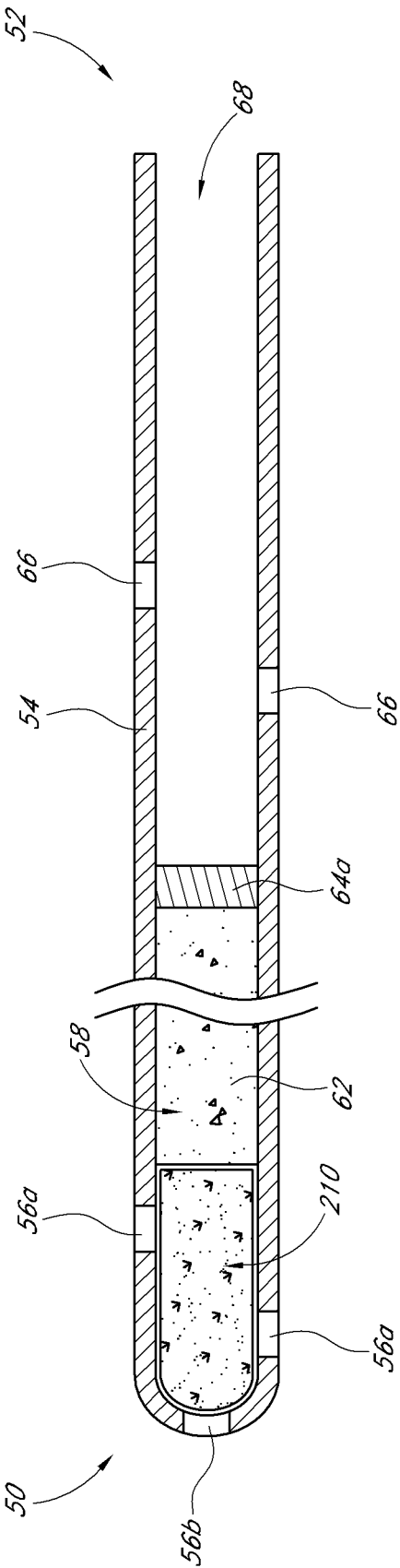
Figure 3C:
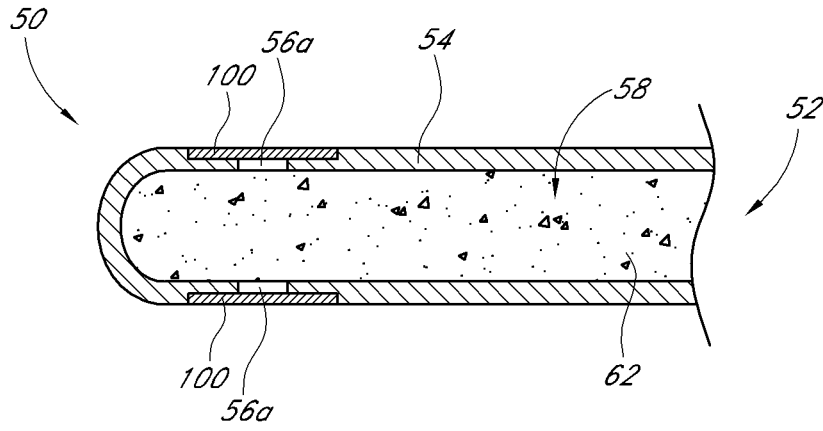
Figure 3D:
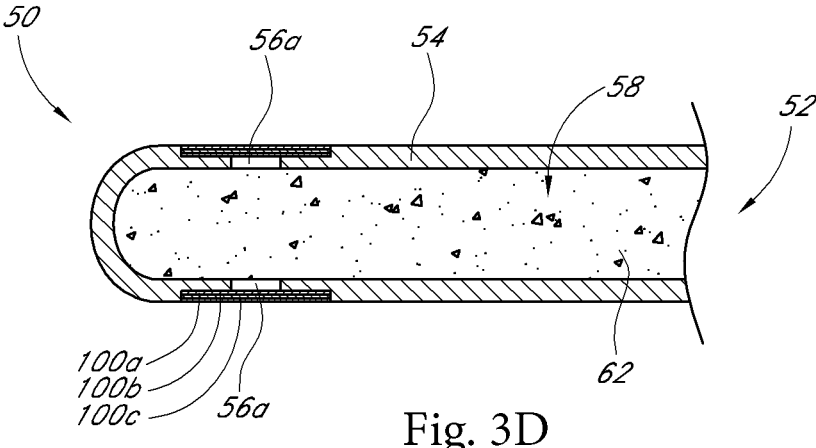

As shown in FIG. 3A, the implant can include a proximal barrier 64a. In some embodiments, a proximal barrier 64a is positioned proximally relative to the drug 62 (see FIGS. 3A-3D). The proximal barrier 64a can be positioned adjacent the drug, hydrogel plug, and/or hydrogel-drug mixture. In some embodiments, the proximal barrier 64a can form a proximal end of the implant. In some embodiments, the proximal barrier 64a is positioned within the implant. In some embodiments, the proximal barrier 64a can include an optional shunt feature. The optional shunt feature can comprise outflow apertures 66 in communication with a proximal inflow lumen 68 located in the proximal region 52 of the implant. In some embodiments, the optional shunt feature can include outflow apertures in communication with a portion of the eye. For example, in some embodiments, the apertures 66 can allow the implant to drain fluid when the implant is implanted within the eye. In some embodiments, elution of the drug from the implant can cause a spike and/or increase in intraocular pressure. Drainage of the fluid from the proximal end of the implant through the apertures 66, for example, can help to reduce swelling and/or the intraocular pressure. In some embodiments, the drainage of fluid through the apertures 66 can help to accelerate elution of the drug 62.

In several embodiments, the orifices 56a are covered (wholly or partially) with one or more elution membranes 100 that provide a barrier to the release of drug 62 from the interior lumen 58 of the implant shell 54. In several embodiments, the elution membrane is permeable to the therapeutic agent, to bodily fluids or to both. In some embodiments the membrane is elastomeric and comprises silicone. In other embodiments, the membrane is fully or partially coated with a biodegradable or bioerodible material, allowing for control of the inception of entry of bodily fluid, or egress of therapeutic agent from the implant. In certain embodiments, the membrane is impregnated with additional agents that are advantageous, for example an anti-fibrotic agent, a vasodilator, an anti-thrombotic agent, or a permeability control agent. In addition, in certain embodiments, the membrane comprises one or more layers 100*a*, 100*b*, and 100*c*, for example, allowing a specific permeability to be developed.

In some embodiments, the outer shell 54 can be coated with a coating. In some embodiments, the coating is a polymeric coating. The coating can be optionally biodegradable. Some other embodiments may comprise an implant made entirely of a biodegradable material, such that the entire implant is degraded over time. In some embodiments, the coating is placed over the entire implant (e.g., enveloping the implant) while in other embodiments only a portion of the implant is covered. In some embodiments, the coating is on the exterior surface of the implant. In some embodiments, the coating is placed on the luminal wall within the implant as an alternate or in addition to the outside of the implant or shell, as discussed below. The coating can assist in controlling elution of the drug through the outer shell. In some embodiments, the coating can help to lengthen the lifespan of the implant (for example, the outer shell). For example, in some embodiments, the coating can bioerode over time. The coating can bioerode and/or dissolve at the same or similar rate as the drug elutes through the outer shell. In some embodiments, the coating bioerodes at a rate that is faster than the drug elutes through the outer shell. In some embodiments, the coating can inhibit and/or prevent the outer shell from bioeroding. For example, in some embodiments, the coating can help to prevent or inhibit some or all biodegradation of the outer shell until all or a portion of the drug has eluted through the outer shell (e.g., after all or some of the therapy has been provided to the patient). For example, in some embodiments, the coating may allow the outer shell 54 to bioerode or dissolve at a slower rate while the drug is being administered to the patient and/or a faster rate once the therapy is completed or is substantially complete.

Similar to the hydrogel plug and regions of drug release described herein, the characteristics of the elution membrane at least partially define the release rate of the therapeutic agent from the implant. Thus, the overall release rate of drug from the implant may be controlled by the physical characteristics of the implant, including, but not limited to, the area and volume of the orifices, the surface area of any regions of drug release, the size and position of any hydrogel plug with respect to both the drug and the orifices and/or regions of drug release, and the permeability of any layers overlaying any orifices or regions of drug release to the drug and bodily fluids.

In some embodiments, the implants described herein can be sized and shaped to be implanted into or through various regions of the eye. For example, the implant can be positioned within the supraciliary space, suprachoroidal space, Schlemm's canal, anterior chamber, vitreous humor, or capsular bag. In some embodiments, the implant can be positioned entirely within the anterior chamber and/or posterior chamber. In some embodiments, the implant is positioned partially in the anterior chamber and/or the posterior chamber. In some embodiments, the implant is positioned within the vitreous humor or cavity to avoid positioning the implant within an optical or visual axis.

Some embodiments disclosed herein are dimensioned to be wholly contained within the eye of the subject, the dimensions of which can be obtained on a subject to subject basis by standard ophthalmologic techniques. Upon completion of the implantation procedure, in several embodiments, the proximal end of the device may be positioned in or near the anterior chamber of the eye and the distal end of the implant may be positioned anywhere within the suprachoroidal space. In some embodiments, the distal end of the implant is near the limbus. In other embodiments, the distal end of the implant is positioned near the macula in the posterior region of the eye. In other embodiments, the proximal end of the device may be positioned in or near other regions of the eye, such as the vitreous chamber or cavity. In some such embodiments, the distal end of the device may also be positioned in or near other regions of the eye. As used herein, the term "near" is used at times to as synonymous with "at," while other uses contextually indicate a distance sufficiently adjacent to allow a drug to diffuse from the implant to the target tissue. In still other embodiments, implants are dimensioned to span a distance between a first non-ocular physiologic space and a second non-ocular physiologic space.

In one embodiment, the drug delivery implant is positioned in the suprachoroidal space by advancement through the ciliary attachment tissue, which lies to the posterior of the scleral spur. The ciliary attachment tissue is typically fibrous or porous, and relatively easy to pierce, cut, or separate from the scleral spur with the delivery instruments disclosed herein, or other surgical devices. In such embodiments, the implant is advanced through this tissue and lies adjacent to or abuts the sclera once the implant extends into the uveoscleral outflow pathway. The implant is advanced within the uveoscleral outflow pathway along the interior wall of the sclera until the desired implantation site within the posterior portion of the uveoscleral outflow pathway is reached.

In some embodiments the total length of the implant is between 1 and 30 mm in length. In some embodiments, the implant length is between 2 and 25 mm, between 6 and 25 mm, between 8 and 25 mm, between 10 and 30 mm, between 15 and 25 mm or between 15 and 18 mm. In some embodiments the length of the implant is about 8, 9, 10, 11, 12, 13, 14, 15, 16, 17, 18, 19, 20, 21, 22, 23, 24, or 25 mm so that that the delivery device containing an implant can be inserted and advanced through the cornea to the iris and produce only a self-sealing puncture in the cornea, in some embodiments, the outer diameter of the implants are between about 100 and 600 microns. In some embodiments, the implant diameter is between about 150-500 microns, between about 125-550 microns, or about 175-475 microns. In some embodiments the diameter of the implant is about 100, 125, 150, 160, 170, 180, 190, 200, 225, 250, 275, 300, 325, 350, 375, 400, 425, 450, 460, 470, 475, 480, 490, or 500 microns. In some embodiments, the inner diameter of the implant is from about between 50-500 microns. In some embodiments, the inner diameter is between about 100-450 microns, 150-500 microns, or 75-475 microns. In some embodiments, the inner diameter is about 80, 90, 100, 110, 125, 150, 175, 200, 225, 250, 275, 300, 325, 350, 375, 400, 410, 420, 425, 430, 440, or 450 microns.

The implant may be sized to have an outer diameter that will permit the implant to fit within a 23-gauge to 25-gauge needle or hollow instrument during implantation; however, larger or smaller gauge instruments or other specialized delivery devices may also be used. For example, the implant can be sized to have an outer diameter that will permit the implant to fit within a 18-, 19-, 20-, 21-, 22-, 23-, 24-, 25-, 26-, 27-, 28-, 29-, and/or 30-gauge needles. The implant can have a constant diameter through all or a portion of its length. In some embodiments, the implant can be sized and shaped to fit within a thin-walled needle, such as an ultra-thin walled needle. Embodiments of the implant may have a maximum outer diameter of about 0.1-0.5 mm, including 0.15-0.45 mm, 0.2-0.4 mm, and 0.25-0.35 mm.

In further embodiments, the interior lumen of an implant may be coated with a layer of hydrophilic material, thereby increasing the rate of contact of ocular fluid with the therapeutic agent or agents positioned within the lumen. In one embodiment, the hydrophilic material is permeable to ocular fluid and/or the drug. Conversely, the interior lumen may be coated with a layer of hydrophobic material, to coordinately reduce the contact of ocular fluid with the therapeutic agent or agents positioned within the lumen. In one embodiment, the hydrophobic material is permeable to ocular fluid and/or the drug.

Figures 4A, 4B, 4C:
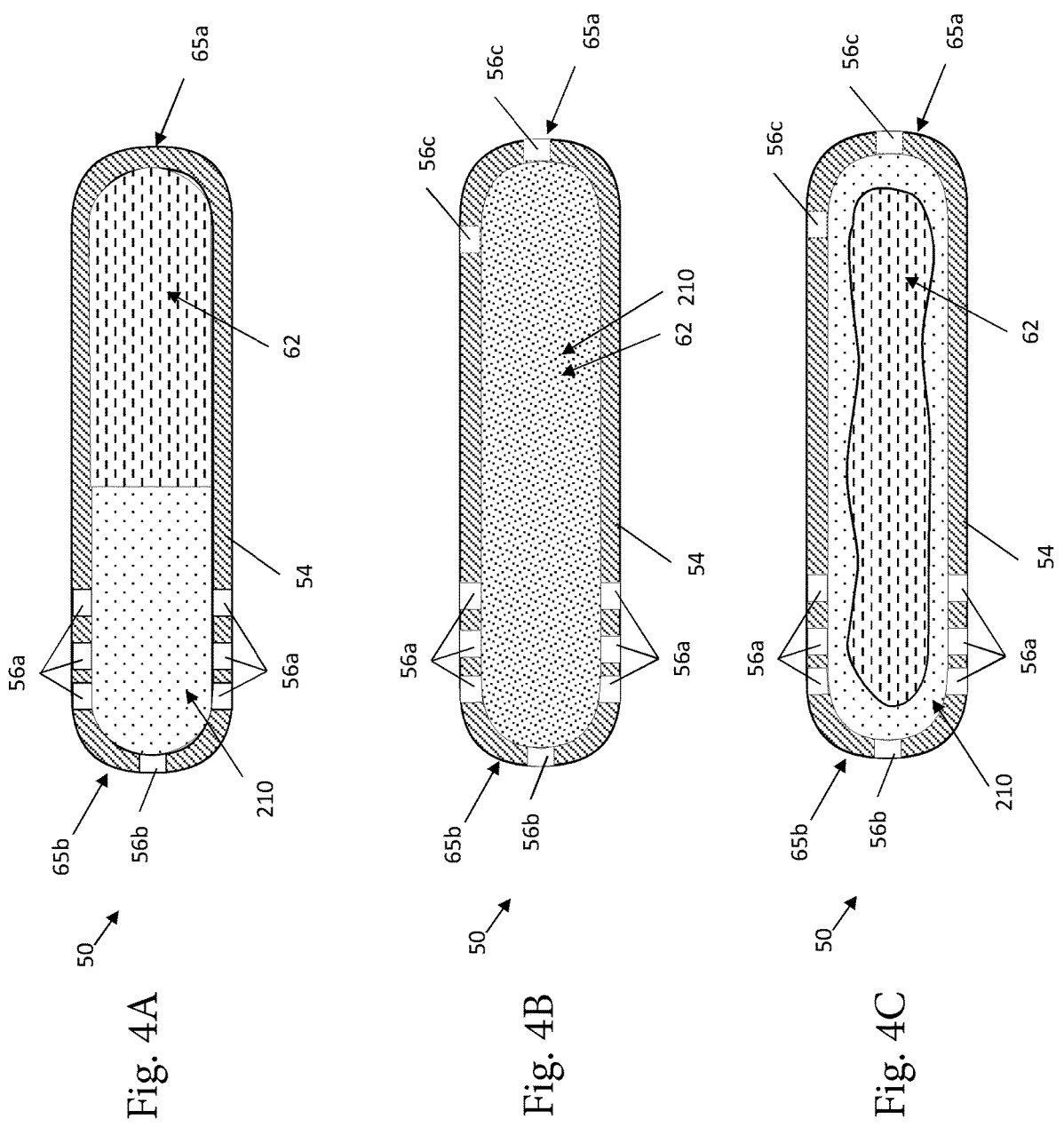
FIG. 4A illustrates a cross-sectional view of an embodiment of a drug delivery implant in accordance with embodiments disclosed herein.
FIG. 4B illustrates a cross-sectional view of an embodiment of a drug delivery implant in accordance with embodiments disclosed herein.
FIG. 4C illustrates a cross-sectional view of an embodiment of a drug delivery implant in accordance with embodiments disclosed herein.

FIGS. 4A-C illustrate additional embodiments of implant 50, which may be especially suitable for direct placement into the vitreous cavity. These embodiments are similar to or identical to those discussed above in many respects including, but not limited to, materials, elution rates, drugs, orifices, configuration, delivery, size, coatings, and the like, such that the descriptions above, including but not limited to the preceding 21 paragraphs relating to FIGS. 3A-D, are also applicable to FIGS. 4A-C. FIG. 4A illustrates a cross-sectional view of another embodiment of the implant 50. The implant shown in FIG. 4A can include any one, or any combination, of features of the implants described herein. As discussed above, the implant can be bierodible or bioresorb-able. As shown, the implant can be capsule-shaped. For example, the implant can include a distal end 65b and a proximal end 65a. The distal end 65b and the proximal end 65a can be rounded. Such configurations can help to prevent or inhibit injury to the patient when the implant is introduced to the patient's eye. Rounded ends of the implant can help to more easily insert the implant into various regions of the patient's eye, such as the supraciliary space, suprachoroidal space, Schlemm's canal, anterior chamber, vitreous humor, posterior chamber, and/or capsular bag.

As shown in FIG. 4A, the implant can include an outer shell 54. The outer shell 54 can include one or more orifices 56a, 56b. The orifices 56a, 56b can be positioned at or near the distal end 65b of the implant. As discussed above, the implant can include an internal or hydrogel plug 210 and a drug 62. In some embodiments, the hydrogel plug 210 is positioned near the distal end 65b of the implant and/or the orifices 56a, 56b. The drug 62 can be positioned adjacent the hydrogel plug 210. For example, the drug 62 can be positioned at or near a proximal end 65a of the implant. In some embodiments, the drug 62 is contained within a drug reservoir.

In some embodiments, the proximal end 65a of the implant forms a closed-end. In some embodiments, the proximal end 65a of the implant includes a cap. For example, the proximal end 65a of the implant can limit or prevent elution of the drug 62 through the proximal end 65a of the implant. For example, the hydrogel plug 210 and the drug 62 can be positioned within the outer shell 54 such that the drug 62 passes through at least a portion of the distal region of the implant. In several embodiments, the drug 62 passes through at least a portion of the hydrogel plug 210 before passing through the outer shell 54. Thus, the hydrogel plug 210 can help to control elution of the drug 62.

In some embodiments, as discussed above, the orifices 56a, 56b can help to control elution of the drug 62 through the hydrogel plug 210 and the outer shell 54. As previously mentioned, the drug 62 can be positioned within the outer shell 54 such that the drug 62 passes through the hydrogel plug 210 before elution. In some embodiments, the orifices 56a, 56b can allow the drug to pass through the outer shell 54 once the drug 62 has passed through at least a portion of the hydrogel plug 210. In some embodiments, the orifices can be sized and shaped, as discussed herein, to adjust the elution rate of the drug through the hydrogel plug 210 and/or the outer shell 54 of the implant.

As mentioned above, the implant can include various volumes of hydrogel plug and drug in certain embodiments of the implant. For example, the ratio of a volume of the drug 62 to hydrogel positioned within the implant for elution can be greater than about 1:1. For example, in some embodiments, at least 50% of the internal volume of the outer shell 54 is filled with drug 62 before the drug is eluted from the implant. In some embodiments, the ratio of volume of drug to hydrogel plug positioned within the implant for elution ranges from about 1:1 to about 2:1, about 2:1 to about 5:2, about 5:2 to about 3:1, about 3:1 to about 7:2, about 7:2 to about 4:1, about 4:1 to about 9:2, and/or other ranges. In some embodiments, the ratio of volume of drug to hydrogel positioned within the implant for elution ranges from about 1:1 to about 1:2, about 1:2 to about 1:3, about 1:3 to about 1:4, among other ranges.

FIG. 4B illustrates a cross-sectional view of another embodiment of the implant 50. The implant shown in FIG. 4B is similar to or identical to the implants discussed herein in many respects. The implant shown in FIG. 4B can include any one, or any combination, of features of the implants described herein.

As shown in FIG. 4B, the implant can include an outer shell 54. The outer shell 54 can include one or more orifices 56a, 56b. The orifices 56a, 56b can be positioned at or near the distal end 65b of the implant. In some embodiments, the outer shell 54 can optionally include one or more or orifices 56c positioned at or near the proximal end 65a of the implant. As discussed above, the implant can include an internal or hydrogel plug 210 and a drug 62. As shown, all or a portion of the drug 62 can be dispersed within and/or mixed with the hydrogel plug 210 to form a hydrogel-drug mixture. The hydrogel-drug mixture can be pre-formed. For example, the hydrogel and the drug can be mixed before being inserted into the interior space of the outer shell 54. In some embodiments, at least 50% of the volume of the hydrogel-drug mixture can include drug, as discussed above. As mentioned previously, the orifices 56a, 56b, and/or the hydrogel can help to control the rate of elution of the drug through the outer shell 54.

FIG. 4C illustrates a cross-sectional view of another embodiment of the implant 50. The implant shown in FIG. 4C is similar to or identical to the implants discussed herein in many respects. The implant shown in FIG. 4C can include any one, or any combination, of features of the implants described herein.

As shown in FIG. 4C, the implant can include an outer shell 54. The outer shell 54 can include one or more orifices 56a, 56b. The orifices 56a, 56b can be positioned at or near the distal end 65b of the implant. In some embodiments, the outer shell 54 can optionally include one or more or orifices 56c positioned at or near the proximal end 65a of the implant. As discussed above, the implant can include an internal or hydrogel plug 210 and a drug 62. As shown, the hydrogel plug 210 can surround at least a portion of the drug 62. As mentioned previously, the orifices 56a, 56b, and/or the hydrogel can help to control the rate of elution of the drug through the outer shell 54. The drug 62 can pass through all or a portion of the hydrogel plug 210 before elution through the outer shell 54.

Figures 6A, 6B:
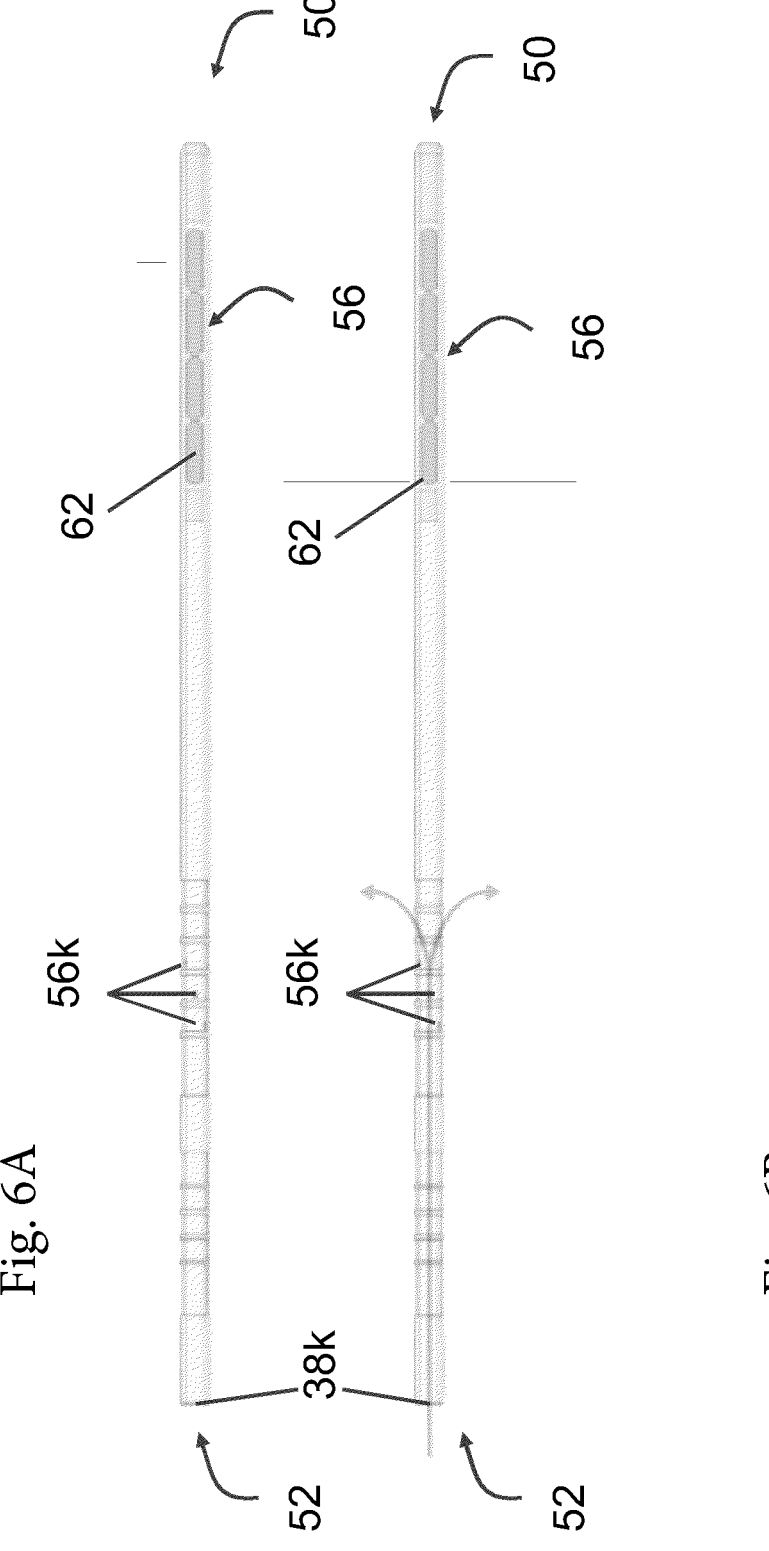
FIGS. 6A and 6B depict various features of elongate delivery devices in accordance with several embodiments disclosed herein.

As schematically shown in FIGS. 6A and 6B, elongate implants can comprise a plurality of the features disclosed herein. For example, FIG. 6A depicts an elongate implant with a proximal 52 and distal end 50, containing a plurality of pellets of therapeutic agent 62. As discussed in more detail herein, the therapeutic agent, depending on the embodiment, may be in a variety of forms, such as pellets, micropellets, vesicles, micelles, or other membrane-like bound structures, oils, emulsions, gels, slurries, etc. The implant comprises a region of drug release 56. Moreover, the embodiments depicted in FIGS. 6A and 6B comprise fluid inflow 38$k$ and outflow 56$k$ pathways, thus allowing the combination of delivery of a therapeutic agent as well as directing fluid to an ocular fluid outflow pathway (e.g., suprachoroidal space).

Figure 6C:
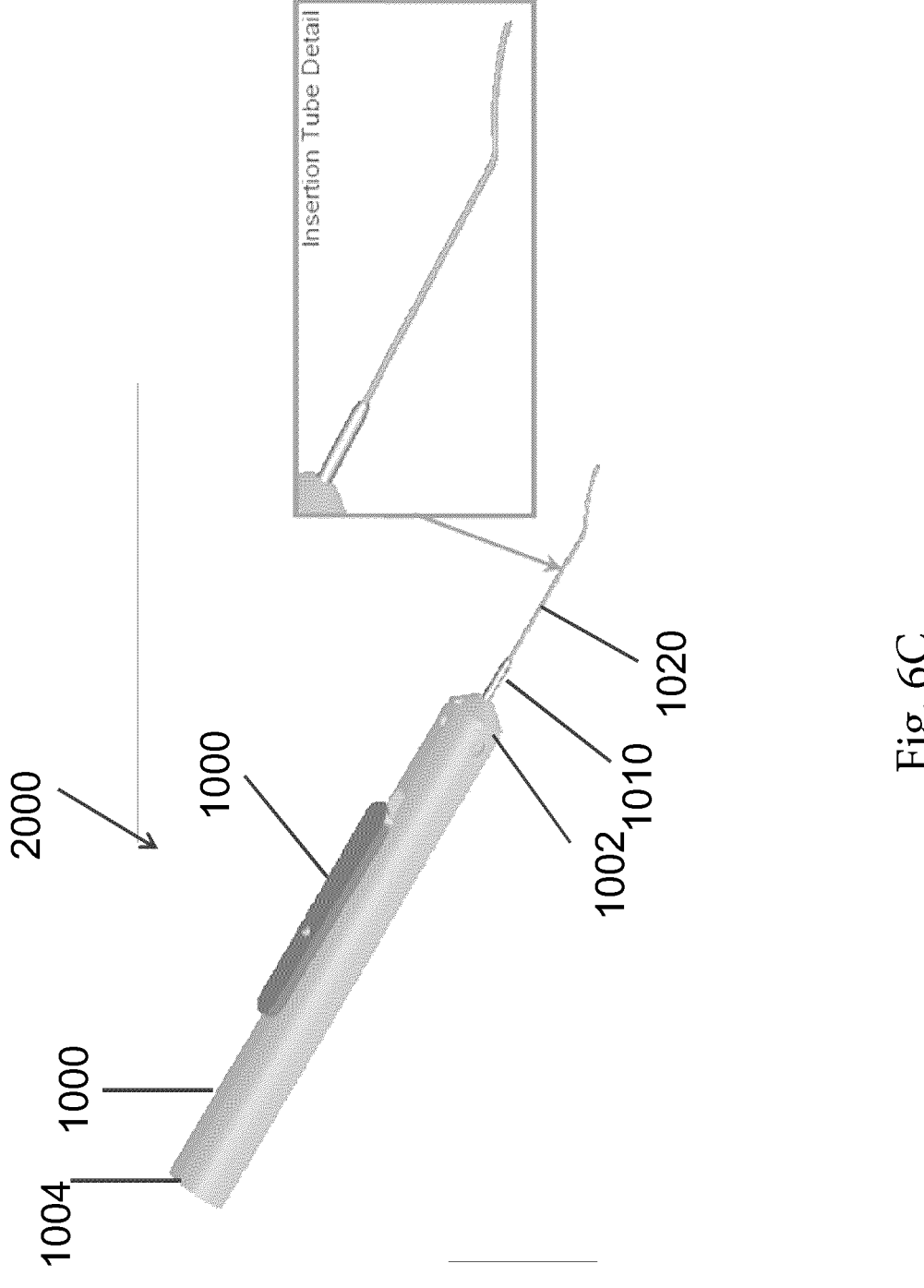
FIG. 6C illustrates one embodiment of a delivery device in accordance with embodiments disclosed herein.
Figure 6D:
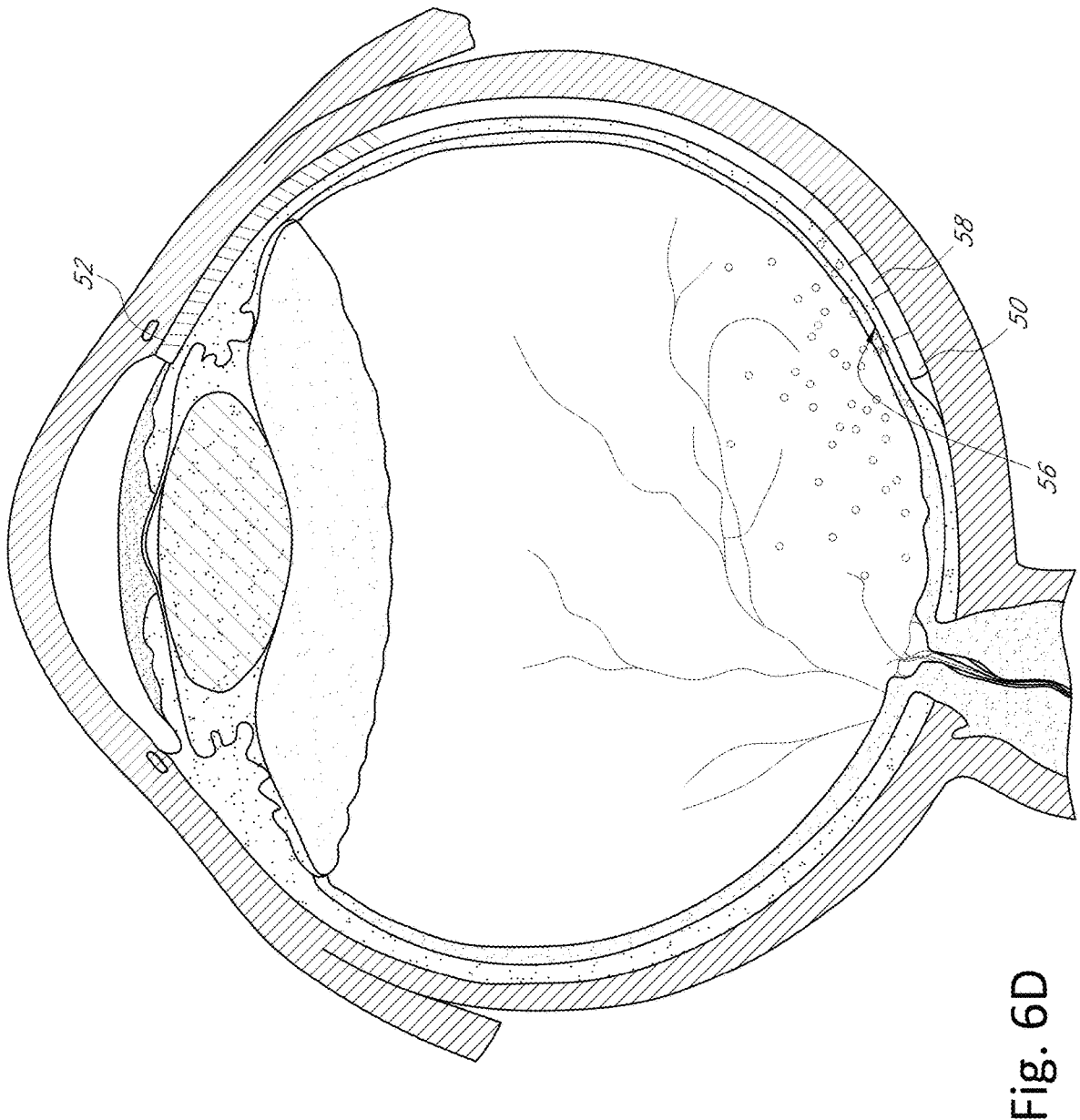
FIG. 6D illustrates an implantation configuration of drug delivery devices in accordance with embodiments disclosed herein.

FIG. 6D schematically depicts an eye with one embodiment of an elongate implant positioned in accordance with several embodiments disclosed herein. As shown the proximal end of the implant 52 resides near the anterior portion of the eye, while the distal end of the implant 50 resides in a more posterior position. The implant can be implanted in the suprachoroidal space, in one embodiment, and positioned such that the region of drug release 56 allows the therapeutic agent 58 to elute from the implant in a posterior region of the eye. While not expressly depicted here, it shall be appreciated that the implant may, optionally, include the fluid inflow and outflow pathway described herein.

Figure 18:
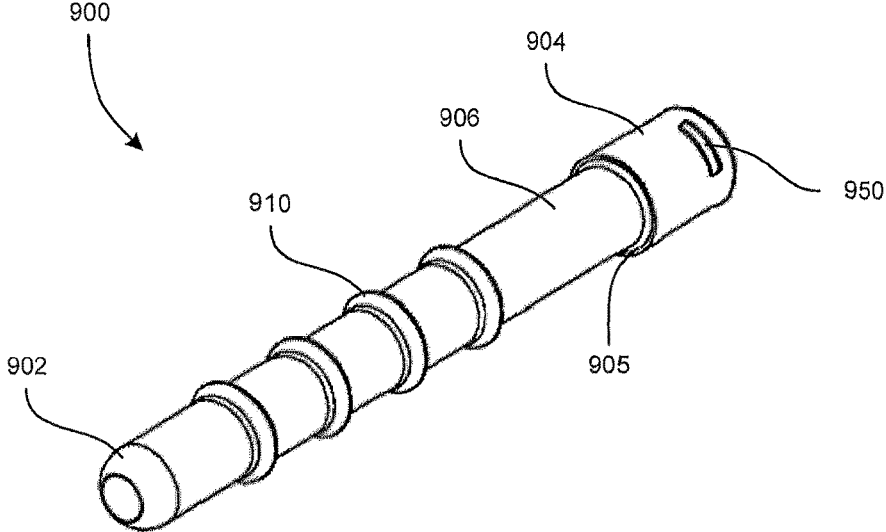
FIG. 18 shows a perspective view of an example embodiment of an ocular implant.
Figure 19:
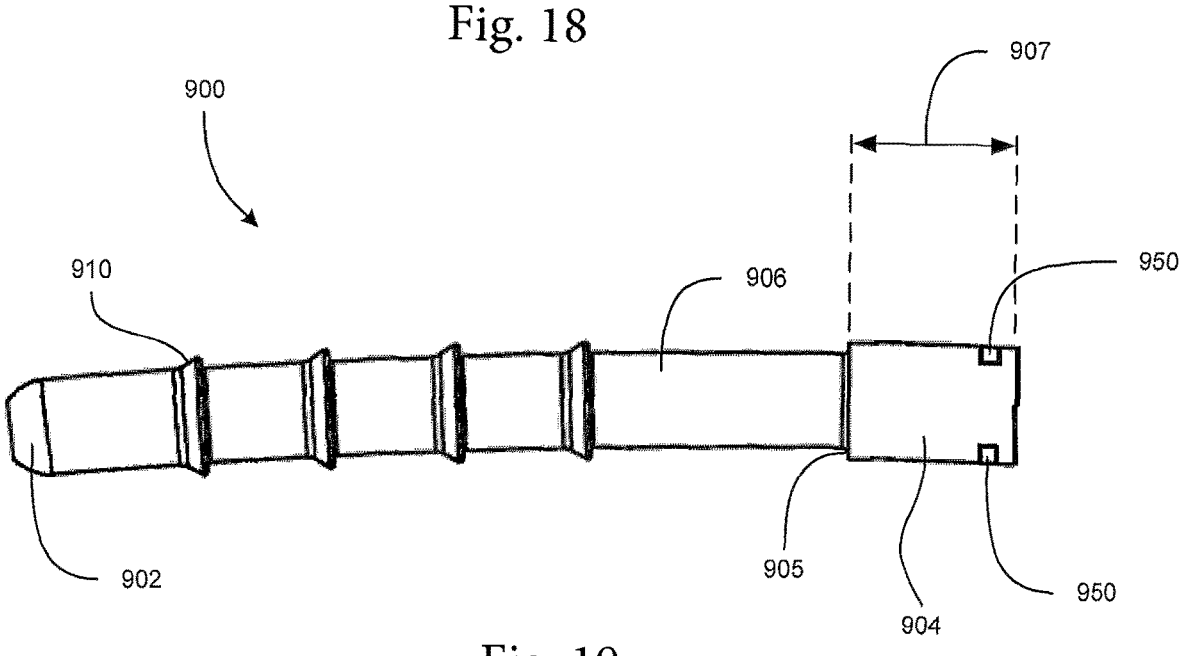
FIG. 19 shows a side view of the example embodiment of an ocular implant of FIG. 18.
Figure 20:
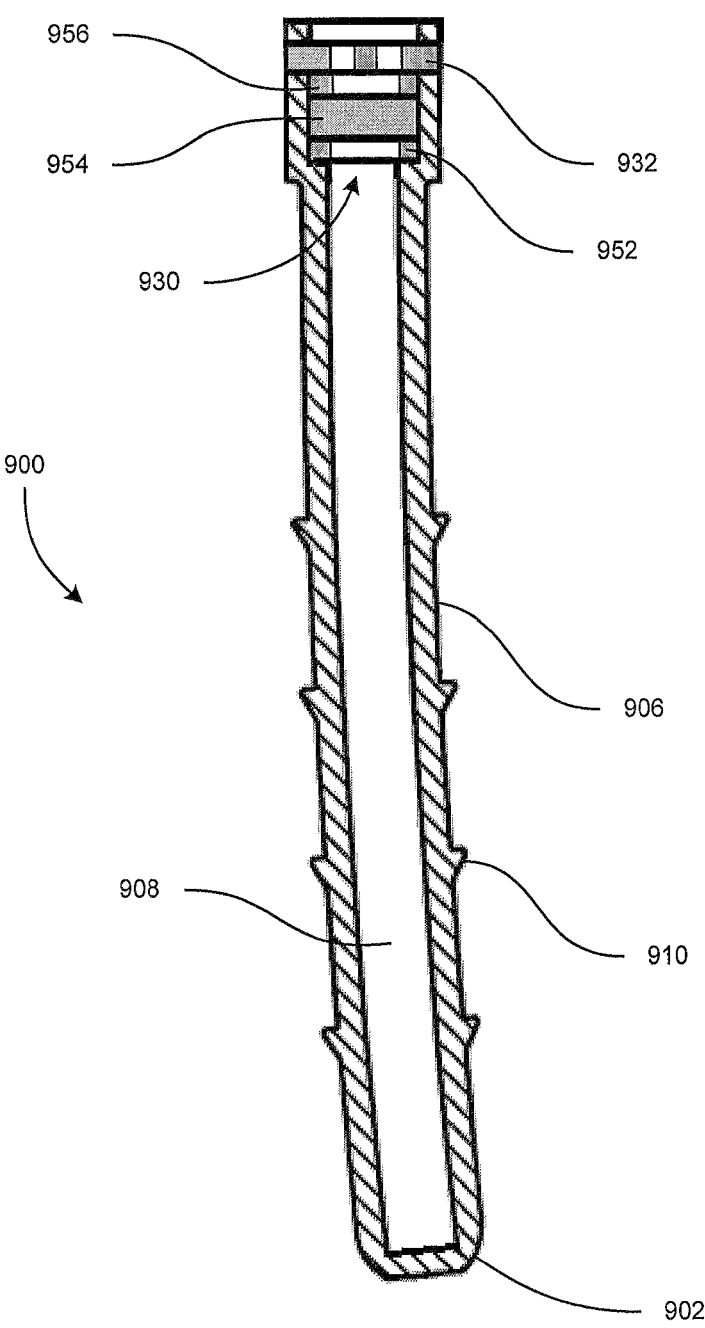
FIG. 20 shows a cross-sectional view of the example embodiment of an ocular implant of FIG. 18.

Other embodiments of ocular implants can be configured to be positioned at least partially in the supraciliary space and/or suprachoroidal space and can include one or more caps or drug release elements as discussed in the section below. FIG. 18 shows a perspective view of an example embodiment of an ocular implant 900 having a drug release element. FIG. 19 shows a side view of the example embodiment of an ocular implant 900. FIG. 20 shows a cross-sectional view of the example embodiment of an ocular implant 900. Various features of the ocular implant 900 are similar to or the same as features illustrated by, or described in connection with, FIGS. 2A-2B and as discussed above herein.

The ocular implant 900 can include an outer shell 906. The outer shell and possibly other components of the implant are preferably made from a biodegradable material. The outer shell 906 can define an interior chamber 908, which can be a drug reservoir for holding one or more drugs as discussed herein. The outer shell 906 can be configured to be implanted into the supraciliary space and/or suprachoroidal space of a patient's eye. The outer shell 906 can have a generally straight configuration, or the implant can be pre-curved to a curvature that is configured to conform generally to the supraciliary space and/or suprachoroidal space. The outer shell 906 can be flexible, in some embodiments, such as to enable the ocular implant to have a generally straight configuration when positioned in a delivery apparatus and to have a curved configuration when implanted into the eye (e.g., in the supraciliary space and/or the suprachoroidal space). The outer shell 906 can include a distal end 902, which can be tapered to facilitate insertion into the supraciliary space and/or the suprachoroidal space.

The outer shell 906 can include a proximal end portion 904, which can include a drug release element 930. In some embodiments, the proximal end portion 904 can have an increased outer diameter such that a step or ridge 905 is formed between the proximal end portion 904 and the central portion of the outer shell 906. In some embodiments, the ocular implant 900 can be inserted into the eye (e.g., into the supraciliary space and/or the suprachoroidal space) until the step or ridge 905 abuts against eye tissue adjacent to the insertion site (e.g., ciliary tissue). The step or ridge 905 can help impede over-insertion of the ocular implant 900. The ocular implant 900 can be configured to release (e.g., elute) a drug, as discussed herein, such as from the proximal end of the ocular implant 900, for example, into the anterior chamber 20. The drug release location (e.g., the proximal end) can be spaced apart from the step or ridge 905 by a distance 907 to prevent the eye tissue that is adjacent the insertion site from covering or otherwise blocking the drug release location of the ocular implant 900. By way of example, the distance can be about 25 microns, about 50 microns, about 75 microns, about 100 microns, about 150 microns, about 200 microns, about 300 microns, about 400 microns, about 500 microns, about 750 microns, about 1000 microns, about 1250 microns, about 1500 microns, or any values therebetween including ranges that are bound by any of these distances. In some embodiments, the step or ridge 905 can extend laterally outward further than shown in FIGS. 18-20. The step or ridge 905 can extend laterally outward by a distance that can be about 25 microns, about 50 microns, about 75 microns, about 100 microns, about 150 microns, about 200 microns, about 300 microns, about 400 microns, about 500 microns, about 750 microns, about 1000 microns, or any values therebetween including ranges that are bound by any of these distances.

The ocular implant 900 can include one or more retention features 910 configured to anchor the implant in place when implanted in the eye. The one or more retention features 910 can include one or more annular ribs on an outer surface of the outer shell 906. The ribs can have angled distal sides and/or can be barbed to facilitate insertion of the ocular implant 900 into the eye while impeding the ocular implant 900 from unintentionally releasing from the eye tissue. In some embodiments, the ribs can have an outer diameter that is substantially the same as the outer diameter of the proximal end portion 904, to facilitate placement in a delivery apparatus. In some embodiments, the one or more retention features 910 can be configured to engage the eye tissue that is adjacent to the insertion site. For example, the one or more retention features 910 can be on or near the proximal end portion 904 or at or near the step or ridge 905. In some embodiments, the retention features 910 can be omitted, and the outer shell 906 can be held in place by friction against the surrounding eye tissue.

The ocular implant 900 can include a drug release element 930. The drug release element is discussed further in the section below.

In several embodiments, the implant comprises a punctual plug. In some such embodiments, the physical arrangement of the drugs within the implant provides advantageous timing of delivery of the drugs. Such an approach is useful, in several embodiments, such as when steroid and cyclosporine are combined to treat dry eye. Many current therapies for dry eye employ an initial treatment with steroid eye drops for a first time period (e.g., two weeks). After the initial period cyclosporine eye drops are added to the treatment regimen. Thereafter the steroid is then tapered off, ending at day 60 and cyclosporine therapy is continued alone, as long as needed. However, according to one embodiment disclosed herein, a punctal implant can deliver steroid and cyclosporine with appropriate timing to achieve a near constant, zero order administration of drug. Such a dosing profile is generally considered more efficient than bolus delivery, such as occurs with eye drops. In several embodiments, the punctal plug is configured, as disclosed herein, to bioerode as the drug payload is released, and in some embodiments will completely erode when all or substantially all of the drug payload is released.

In several embodiments employing multiple drugs, the second (or third, etc.) agent results in synergistic effects when combined with the first agent. In other embodiments, the second agent reduces one or more side effects associated with the first agent.

As such, several embodiments provide for implants for insertion into a punctum of the eye of a subject, comprising an outer shell having a proximal end, a distal end, the outer shell being shaped to define an interior lumen, the outer shell dimensioned for insertion into the punctum of the eye of a subject, at least a first active drug positioned within the interior lumen, at least one region of drug release the proximal portion of outer shell, and a distal occlusive member within the inner lumen, the distal occlusive member preventing elution of the first active drug from the distal end of the implant.

In several such embodiments, the first active drug elutes from the lumen to the tear film of the eye of the subject by passing through the at least one region of drug release. In some embodiments, the implant is dimensioned to be implanted with the distal end of the outer shell positioned in the lacrimal duct. In some embodiments, the implant is dimensioned to be implanted with the distal end of the outer shell positioned in the lacrimal sac. In several embodiments, the implant is dimensioned to be implanted with the distal end of the outer shell positioned in the nasolacrimal duct.

In several embodiments, there is also provided a punctal implant for insertion into a punctum of the eye of a subject and configured to deliver two or more active drugs to the eye of the subject, the implant comprising an outer shell comprising (i) a proximal end comprising at least one region of drug release and a flange, (ii) a closed distal end, and (iii) an interior lumen comprising at least two active drugs positioned within the lumen.

In several embodiments, there is also provided a punctal implant for insertion into a punctum of the eye of a subject and configured to deliver two or more active drugs to the eye of the subject, the implant comprising an outer shell comprising (i) a proximal end comprising at least one region of drug release and a flange, (ii) a closed distal end, and (iii) an interior lumen comprising at least two active drugs positioned within the lumen, wherein the region of drug release comprises aperture through an annular ring positioned at the proximal-most portion of the interior lumen, wherein said aperture allows elution of the two or more active drugs to occur only through the occlusive member, wherein the dimensions of the aperture at least partially defines the elution rate of the two or more active drugs, wherein the flange is configured to rest on the surface of the eyelid when the implant is inserted into the punctum, and wherein the first and second active drug elute from the lumen to the tear film of the eye of the subject by passing through the at least one region of drug release.

In several embodiments, the at least one region of drug release comprises at least one aperture. Additionally, in some embodiments, the implant further comprises at least one membrane that occludes the at least one aperture, wherein the membrane is permeable to the at least a first active drug, wherein the membrane allows elution of the at least a first active drug to occur only through the at least one membrane.

In several embodiments, the at least one region of drug release comprises a plurality of apertures through the outer shell and positioned randomly or in a patterned array throughout the proximal portion of the implant. As above, at least a portion of the plurality of apertures is occluded by a membrane permeable to the first active drug.

Some embodiments provided for herein result in elution of drug (or drugs) from the implant with zero-order or pseudo zero-order kinetics.

In some embodiments, the intraocular target is the posterior chamber of the eye, the anterior chamber of the eye, both the anterior chamber and posterior of the eye, or the macula, the retina, the optic nerve, the ciliary body, and the intraocular vasculature.

In several embodiments, the drug acts on the intraocular target tissue to generate a therapeutic effect for an extended period. In one embodiment, the drug comprises a steroid. In such embodiments, the implant contains a total load of steroid ranging from about 10 to about 1000 micrograms, steroid is released from the implant at a rate ranging from about 0.05 to about 10 micrograms per day and/or the steroid acts on the diseased or damaged target tissue at a concentration ranging from about 1 to about 100 nanomolar. In some embodiments, the steroid additionally generates side effects associated with accumulation of physiologic fluid, and an optional shunt transports the accumulated fluid from the first location to the remote second location (such as, for example, from the anterior chamber to an existing physiological outflow pathway, such as Schlemm's canal or the naso-lacrimal duct).

In several embodiments, the at least one region of drug release comprises an occlusive member that is permeable to said two or more active drugs, and the occlusive member allows elution of the two or more active drugs to occur only through the occlusive member. In several embodiments, the thickness of the occlusive member at least partially defines the elution rate of the active drug (or drugs). In several embodiments, having a flange, the flange is configured to rest on the surface of the eyelid when the implant is inserted into the punctum. In several embodiments, the active drug (or drugs) elute from the lumen to the tear film of the eye of the subject by passing through the at least one region of drug release.

In several embodiments, the occlusive membrane is dimensioned based on the permeability of said occlusive member to said first active drug (and second or more) and the desired relative timing and duration of elution of said first and second active drugs. In several embodiments, the occlusive member has a thickness of between about 0.0001 and 0.0005 inches. In certain embodiments, the occlusive member is integrally formed with the outer shell of the implant. In some embodiments, the occlusive member further comprises randomly or patterned holes through the occlusive membrane.

In some embodiments, a first active drug is placed in a more proximal position within the interior lumen relative to the position of a second active drug. In some embodiments, a third active drug is included, and in certain such embodiments, the first active drug and second active drug are positioned adjacent to one another and both the first and second active drugs are placed in a more proximal position within the interior lumen relative to the position of the third active drug.

In several embodiments, the active drug (or drugs) is formulated as tablets, as a nanodispersion, or a combination thereof. In some embodiments, a first active drug is formed as a discontinuous first phase and a second active drug is formulated as dispersion of solid of liquid particles into which the first active drug is dispersed.

In several embodiments, the device may be filled with protein drug in the form of an amorphous solid, or a powder, or a crystalline solid; or in the form of a suspension of these; or in the form of a solution. If the device is filled with a suspension or solution, the initial concentration of protein drug can optionally be in the range of about 100 to about 500 milligrams per milliliter, including about 100 to about 150 mg/mL, about 150 to about 200 mg/mL, about 200 to about 250 mg/mL, about 250 to about 300 mg/mL, about 300 to about 350 mg/mL, about 350 to about 400 mg/mL, about 400 to about 450 mg/mL, about 450 to about 500 mg/mL, concentrations in between those listed. In some preferred embodiments, the concentration ranges from about 200 to about 300 mg/mL.

In several embodiments, the drug may include excipients such as trehalose to stabilize the protein drug during prior processing (such as lyophilization), or during its use in the eye. Depending upon the concentration of trehalose, there may be an osmotic gradient created from inside the device to outside the device, such that water from the vitreous will tend to ingress the device, expelling some of the drug. This event may be intentional, if it is desirable to create an initial burst of elution. Otherwise, the concentration of trehalose may be reduced to an isosmotic level, or a polymer bearing multiple hydroxyl residues may be utilized to reduce osmolarity and slow loss by elution.

Other excipients may comprise buffers to maintain neutral pH as the bioresorbable material hydrolyzes. Such buffers may also be polymeric to slow their loss by elution.

In several embodiments, the outer shell of the implant comprises a bulge in the distal region in order to anchor the implant in the punctum.

In several embodiments, a first active drug elutes from an implant for a period of between 1 and 75 days, and a second active drug elutes for a period of time ranging from about 1 to about 24 months after the first active drug is eluted.

In several embodiments, the implants disclosed herein have a length of between about 0.5 and about 2.5 mm. Some embodiments of the implants have a length of about 1.4 to about 1.6 mm. Some embodiments of the implant have a diameter of about 0.2 to about 1.5 mm. Some embodiments of the implant have a diameter of about 0.2 to about 0.6 mm.

Depending on the embodiment, the first active drug may be a steroid. In some such embodiments, the steroid is selected from the group consisting of loteprednol etabonate, dexamethasone, and triamcinolone acetonide. In some embodiments, a second active drug is cyclosporine and is optionally formulated as a nanodispersion. In several embodiments, the first active drug is cyclosporine A. In several embodiments, the first active drug facilitates tear production.

Several embodiments optionally comprise a retention protrusion configured to anchor the implant in an implantation site (e.g., the punctum). Such retention protrusions optionally comprise one or more of bulges, ridges, claws, threads, flexible ribs, rivet-like shapes, flexible barbs, barbed tips, expanding material (such as a hydrogel), and biocompatible adhesives. In some embodiments, the expanding material is placed on an exterior surface of the outer shell of the implant and expands after contact with a solvent, such as, for example, intraocular fluid or tear film.

In several embodiments the outer shell of the punctal plug implant comprises a bioerodible material. As discussed in more detail elsewhere in this disclosure, in several embodiments the bioerodible material is configured to erode at a rate that allows the entire implant (including those for punctal insertion, as well as other implant locations) to completely or substantially bioerode. This can be optionally configured to mimic the timing of drug release such that upon elution of all or substantially all of a drug payload from an implant (including punctal implants) the implant itself is completely or substantially eroded. In some embodiments, however, the bioerosion of the implant is tailored to begin only after all or substantially all of the drug payload has been delivered.

Figure 5A:
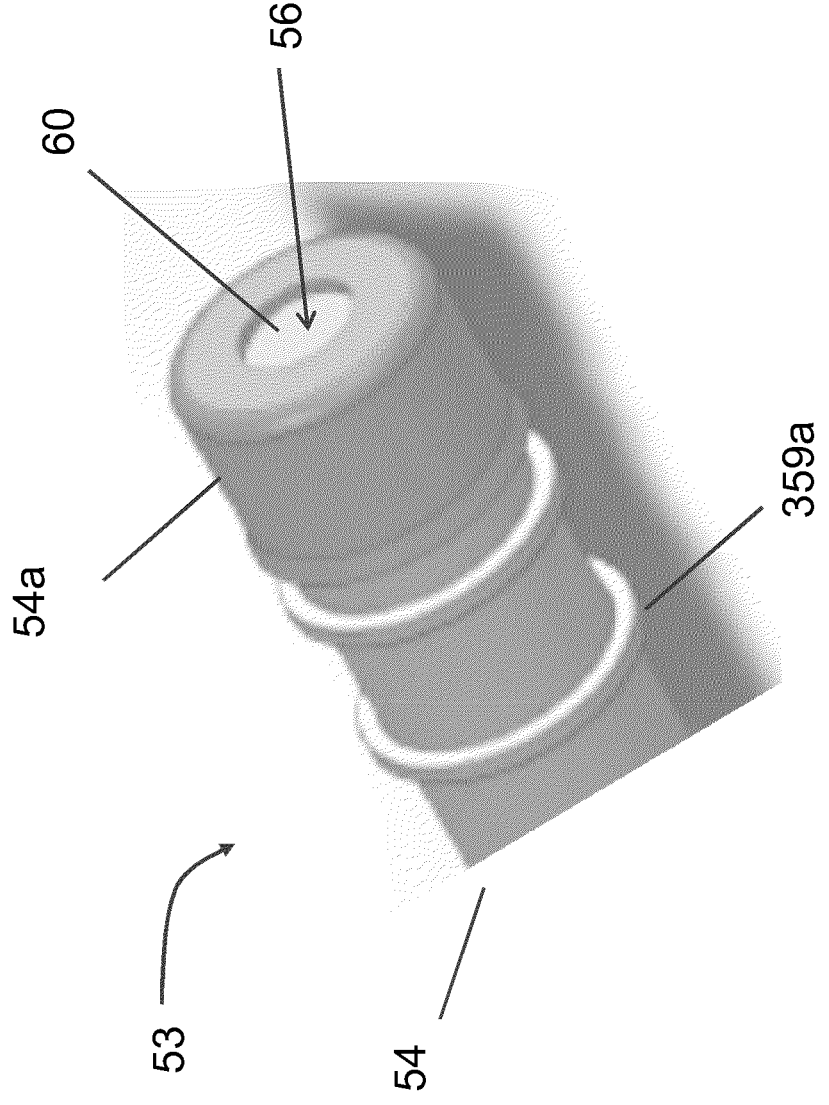
FIGS. 5A-5B illustrate various drug delivery devices in accordance with embodiments disclosed herein.
Figure 5B:
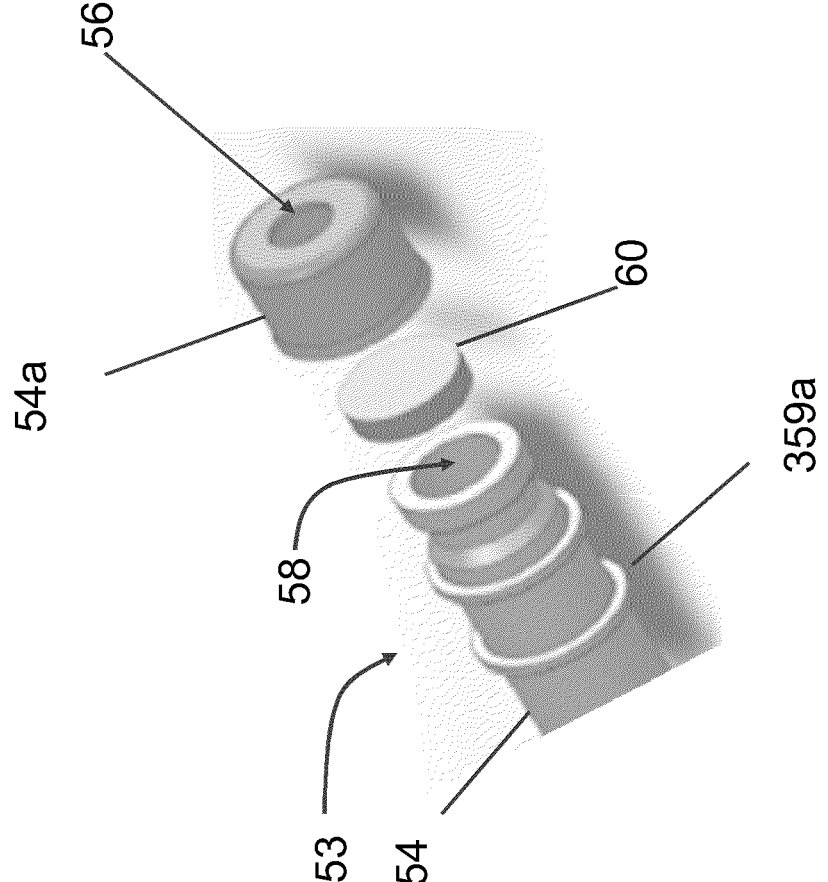

It is to be understood that any device described herein, including that of FIG. 2A and FIG. 2B or FIG. 5A and FIG. 5B, can be fitted with any cap including a drug release element or a cap as discussed below and shown in FIG. 5A-5B and FIGS. 12-17, and that the drug delivery implant shown in FIG. 18 to FIG. 20 can be fitted with a cap as shown in FIG. 5A and FIG. 5B or not include any cap. Additionally, any of the embodiments disclosed and illustrated herein can include a cap, including a drug release element, at the distal end as an alternate to the proximal end or they may include them at both ends. If the implant has a cap at both ends, the type of cap at each end may be the same or it may differ, and each may be delivering the same drug from the same lumen, the same drug from the same lumen where the lumen is separated into two compartments by a barrier within the lumen, the same drug from different lumens, different drugs from a lumen containing a barrier separating the two drugs, or different drugs from different lumens. Where there are two caps, the timing and/or rate of the delivery of the drugs may be the same or different and, if different timing, they may overlap or be distinct. Similarly, the implants similar to FIG. 5A and FIG. 5B or FIG. 18 to FIG. 20 can include a drainage lumen like that of FIG. 2A and FIG. 2B or as otherwise described herein.

It is further understood that the possible features and materials of the implants of FIGS. 2A and 2B, FIG. 5A and FIG. 5B and FIG. 18 to FIG. 20 including, but not limited to, biodegradable materials, sizes, lengths, diameters, retention features, shunts, pores, coatings, distal end shapes, and the like are as discussed throughout this specification, including in this section and the previous section. Physical separation in the specification is not intended, and should not be interpreted, as meaning that the ideas are separate and cannot be applied to the various device embodiments as described herein as would be understood by those skilled in the art.

Caps, Including Drug Release Elements

In several embodiments, the implant may include one or more caps. In such embodiments, one or more portions of the implant are manufactured separately, then combined for a final implant that is ready for insertion to a target site (e.g., an assembled cap and implant shell). As shown, for example, in FIG. 5A, the implant 53, in several embodiments, comprises an implant shell 54, a separate cap 54a (which is shown for clarity in a different shade, but is optionally constructed of the same or different material as compared to the implant shell). Any of the various cap configurations can be used with any of the implant shells, adjusting, of course, for dimensions that allow interaction between the components.

As shown in FIG. 5A, the cap 54a comprises a central aperture, thereby creating a region of drug release 56. In several embodiments, the assembly of certain such embodiments exploit the elastic or semi-elastic characteristics of the membrane 60 through which the drug (or drugs) housed within the implant will elute. Advantageously, in several embodiments, the elastic properties of the membrane 60 allow the cap of an implant to be press fit onto the implant shell, and then retained by the pressure provided against the cap by the elastic rebound of the membrane (e.g., a "self-lock" feature). Thus, the membrane 60, in several embodiments, not only serves to define the release rate of the drug (or drugs), it also functions as a gasket to seal the interior portions of the implant from the outer environment, thus limiting the fluid communication between interior and exterior portions to that occurring through the membrane 60. The membrane 60 may be constructed of any material or materials suitable for eluting the drug. For example, the membrane 60, in one embodiment, comprises ethylene vinyl acetate, while in another embodiment, the membrane comprises silicone or other partially or semi-permeable materials material, homopolymers, polymer blends and copolymers, such as random copolymers and block copolymers, polyethylene, polyurethane, polyethersulfone, polyamide, poly(carbonate urethane), poly(ether urethane), silicone poly(carbonate urethane), silicone poly(ether urethane), PurSil™, Elasthane™, CarboSil™ and/or Bionate™. Biodegradable materials discussed above with regard to the outer shell may also be used for the membrane, cap and other components. The selection of the membrane material and its dimensions (e.g., its thickness) are derived, at least in part, by the drug of choice, the form in which it is placed in the implant (free acid, prodrug, oil, solid, micelle, etc.), whether ocular fluids are to be excluded from the device, etc.

FIG. 5B depicts an exploded view of one embodiment of the implants disclosed herein. The implant 53 comprises at least one internal lumen 58 to house a therapeutic agent (or agents). As discussed above, the implant further comprises a cap 54a and a membrane 60, which when assembled together create a region of drug release 56 that is tailored (based on the membrane) to a particular therapeutic drug (or drugs) of interest.

In various embodiments, the thickness of the membrane 60 (taken in conjunction with the particular therapeutic agent or agents of choice) ranges from about 30 to about 200 μm in thickness, including about 30 to about 200 μm, about 50 to about 200 μm, about 70 to about 200 μm, about 90 to about 200 μm, about 30 to about 100 μm, about 30 to about 115 μm, about 50 to about 125 μm, about 63 to about 125 μm, about 84 to about 110 μm, about 57 to about 119 μm, and overlapping ranges thereof. In several embodiments, the thickness of the membrane 60 also defines, at least in part, the elution rate of the drug (or drugs) of interest. The size of the aperture of the cap also contributes to the elution rate.

Many alternatives and variations are possible. For example, in some cases, assembly of the embodiment shown in FIGS. 5A and 5B can include providing an outer shell 54, filling the drug reservoir. A cap 54a with a membrane 60 can be applied over the proximal end of the shell 54. In some embodiments, the cap 54a can be advanced distally until a desired amount of membrane compression (e.g., 30 microns or any other suitable amount as discussed herein) is achieved, and the cap 54a can then be crimped or otherwise fastened, reversibly or irreversibly, onto the shell 54. In some embodiments, a micrometer can be used to determine the amount of membrane compression.

Figures 13A, 13B:
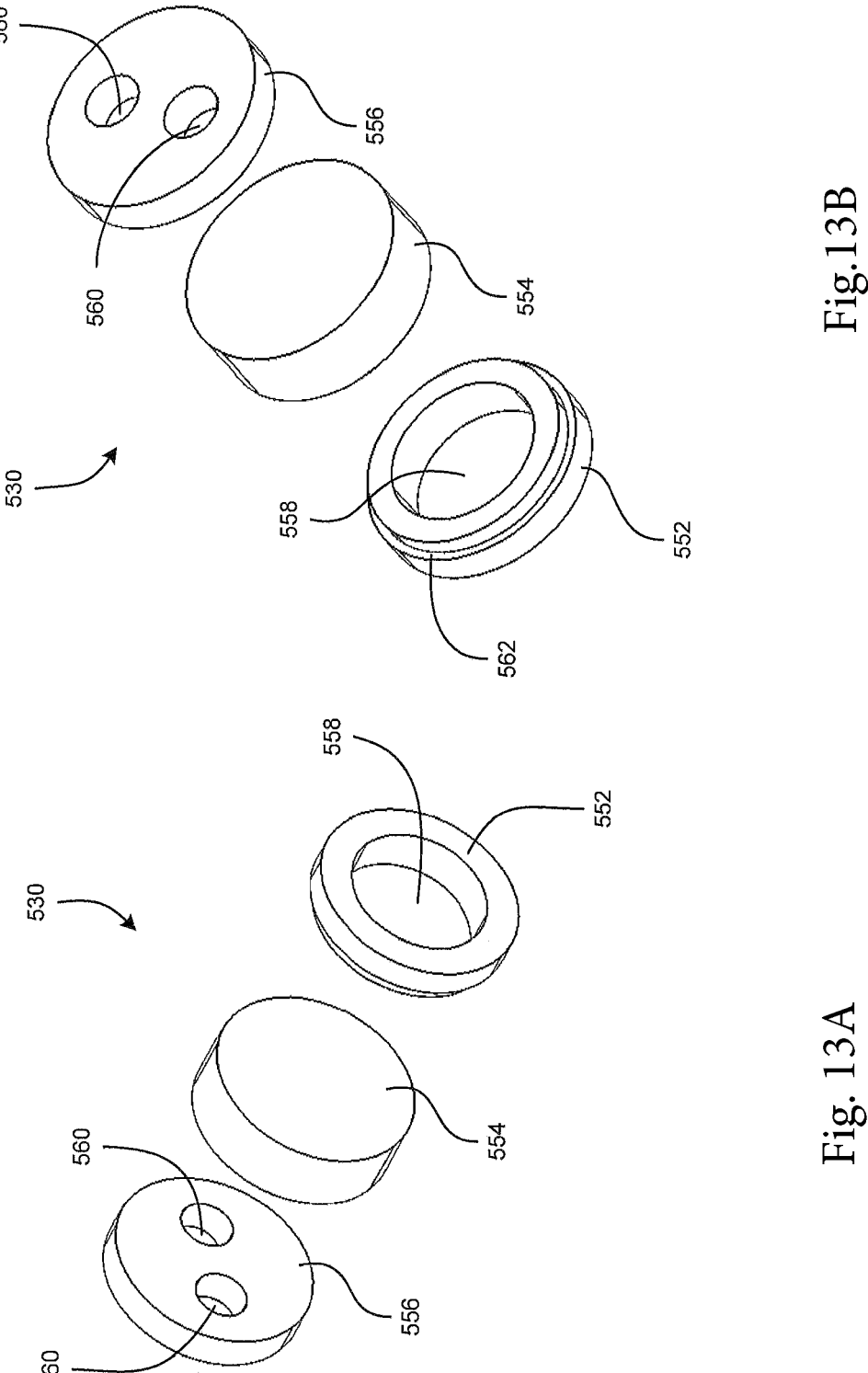
FIG. 13A is a distal exploded perspective view of a drug release element.
FIG. 13B is a proximal exploded perspective view of the drug release element of FIG. 13A.

One particular kind of cap is referred to herein as a drug release element. FIG. 13A shows a distal exploded perspective view of the drug release element 530. FIG. 13B shows a proximal exploded perspective view of the drug release element 530. The drug release element 530 can be configured to slowly elute the drug, as described herein. The drug release element 530 can be positioned at or near the proximal end 504 of the implant 500. In other embodiments, it can be positioned at or near the distal end of the implant or at both ends. The shell 506 can include a shelf 548. The proximal portion of the shell 506 interior that is proximal of the shelf 548 can have a larger diameter than the portion that is distal of the shelf 548. In some embodiments, the shelf 548 can include a consistent annulus size around its circumference. In some embodiments, the shelf 548 does not have a consistent annulus around its circumference, and in some cases the shelf 548 can be one or more protrusions that create a stop for the distal seal member, as discussed herein. The shell 506 can include one or more slots 550, which can be configured to receive the retainer 532, as described herein. In some embodiments, the shell 506 can include two slots 550 positioned generally opposite each other.

Figure 14:
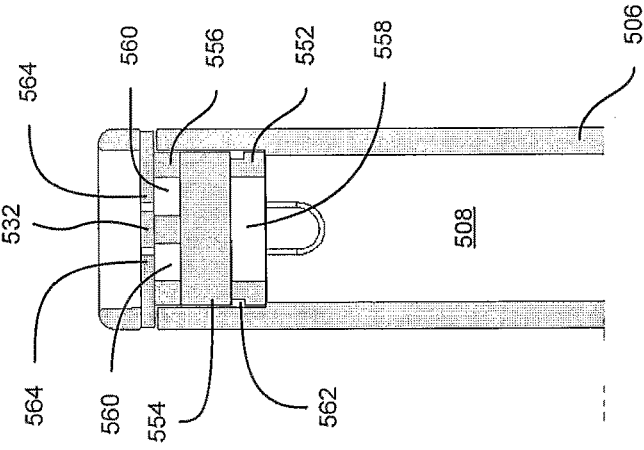
FIG. 14 is a cross-sectional view of an implant with a drug release element.

The drug release element 530 can include a distal seal member 552, a membrane 554, and a proximal seal member 556. The distal seal member 552 can be seated against the shelf 548 on the shell 506. The distal seal member 552 can have an outer diameter that is greater than the distal portion of the shell interior (distal of the shelf 548) and that is less than the proximal portion of the shell interior (proximal of the shelf 548). The distal seal member 552 can have a generally annular shape and/or can have an opening 558 extending therethrough. The proximal seal member 556 can have an outer diameter that is greater than the distal portion of the shell interior (distal of the shelf 548) and that is less than the proximal portion of the shell interior (proximal of the shelf 548). The proximal seal member 556 can be inserted into the proximal end 504 of the shell 506. The proximal seal member 556 can be generally disc shaped. The proximal seal member 556 can include at least one opening 560 extending therethrough. In the illustrated embodiment, the proximal seal member 556 includes two openings 560. The membrane 554 can be positioned between the distal seal member 552 and the proximal seal member 556, and in some embodiments, the membrane 554 can be compressed between the distal seal member 552 and the proximal seal member 556. The retainer 532 can retain the drug release element 530 in the compressed state (e.g., with the membrane 554 compressed), as discussed herein. The distal seal member 552 can include a step 562. FIG. 14 shows the membrane 554 in an undeformed state. When compressed, the membrane 554 can deform to fill the space of the step 562.

The distal seal member 552 and/or the proximal seal member 556 can be made of various biocompatible materials, as discussed herein, such as ceramic or metal (e.g., titanium). In some embodiments, forming the members 552 and/or 556 out of a ceramic material can be advantageous for creating small details on the parts. In some embodiments, one or both of the seal members 552 and 556 can be made from a resilient biocompatible material that is impermeable, or substantially impermeable, to the drug (e.g., silicone). The membrane 554 can be made from various suitable materials that allow the drug to elute from the implant 500. In some embodiments, the membrane can be made from ethylene vinyl acetate (EVA). The rate of elution of the drug can depend, at least in part, on the percentage concentration of vinyl acetate in the EVA material. The vinyl acetate concentration can be less than or equal to about 40%, less than or equal to about 30%, less than or equal to about 25%, at least about 10%, at least about 20%, at least about 25%, and/or at least about 30%, although values outside these ranges may be used in some embodiments. The vinyl acetate concentration can be between about 10% and about 30%, between about 20% and about 30%, or between about 25% and about 30% of the EVA material. In some embodiments, the vinyl acetate concentration can be about 25% or about 28% of the EVA material.

Figure 15:
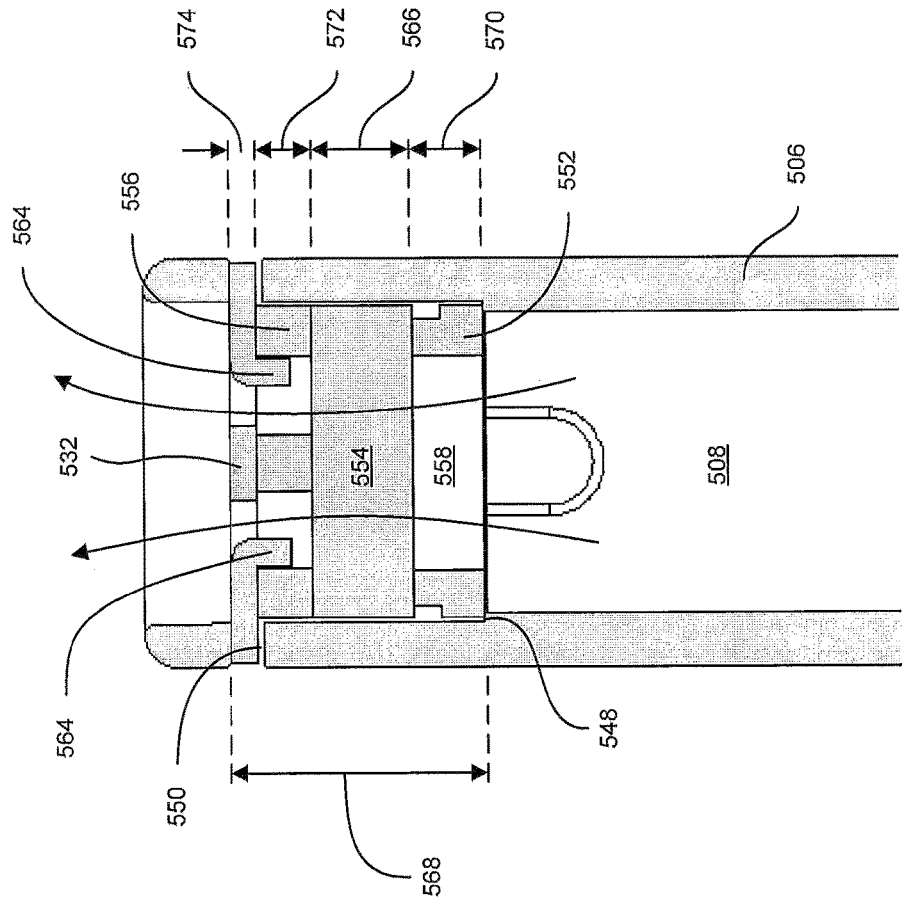
FIG. 15 is a partial cross-sectional view of the implant with a drug release element.

As discussed herein, the membrane 554 can be compressed between the distal seal member 552 and the proximal seal member 556. The proximal seal member 556 can be pressed distally to compress the membrane 554, and the retainer 532 can be inserted through the slot 550 such that the retainer is positioned proximally of the proximal seal member 556. The retainer 532 can have a length that is greater than the inner diameter of the proximal portion of the shell interior and a length that is less than or equal to the outer diameter of the shell 506 at the slots 550. When inserted, the retainer 532 can extend into two opposing slots 550. The force from the compressed membrane 554 can press the retainer 532 in the proximal direction, and the slots 550 can hold the retainer in place to maintain the membrane 554 in the compressed configuration. The retainer 532 can have a generally hourglass shape, although other shapes can also be used, in some embodiments. The retainer can include one or more tabs 564, which can be folded down to secure the retainer 532. FIG. 14 is a cross-sectional view that shows the retainer 532 inserted with the tabs 564 up. FIG. 15 is a partial cross-sectional view that shows the retainer 532 inserted with the tabs 564 folded down to engage the proximal seal member 556. When folded down, the tabs 564 can enter the one or more openings 560 and can engage the proximal seal member 556, which can prevent or impede the retainer 532 from moving (e.g., from sliding out of the slot 550). In some embodiments, when the membrane 554 is compressed, a portion of the membrane 554 can be pushed proximally into the one or more openings 560, and the folded tabs 564 can engage the membrane 554, which can facilitate the securement of the membrane 554.

The drug can elute from the proximal end of the implant 500. The drug can pass from the internal chamber 508, through the at least one opening 558 in the distal seal member 552, to the membrane 554. The membrane 554 can be configured to permit the drug to pass through the membrane 554 at a desired elution rate. The drug can pass through the at least one hole 560 in the proximal seal member 556, past the retainer 532, and out of the proximal end 504 of the implant 500. In FIG. 15, the elution of the drug is shown by two arrows. In some embodiments, the thickness and/or compression of the membrane 554 can affect, at least in part, the elution rate of the drug. In some embodiments, the membrane 554 can have a compressed thickness of at least about 50 microns, at least about 75 microns, at least about 80 microns, at least about 90 microns, at least about 95 microns, at least about 100 microns, less than or equal to about 200 microns, less than or equal to about 150 microns, less than or equal to about 125 microns, less than or equal to about 110 microns, less than or equal to about 105 microns, less than or equal to about 100 microns, less than or equal to about 95 microns, and/or less than or equal to about 90 microns, although values outside these ranges may be used in some embodiments. The compressed thickness 566 of the membrane 554 can be between about 75 microns and about 125 microns, between about 85 microns and about 105 microns, or between about 90 microns and about 100 microns. In some embodiments the compressed thickness 566 of the membrane 554 can be about 95 microns. The membrane can be compressed by at least about 10 microns, at least about 20 microns, at least about 30 microns, at least about 40 microns, less than about 50 microns, less than about 40 microns, less than about 30 microns, and/or less than about 20 microns, although values outside these ranges may be used, in some embodiments. The membrane 554 can be compressed by an amount between about 20 microns and about 40 microns, or about 25 microns and about 35 microns. The membrane 554 can be compressed by about 30 microns, in some embodiments. Compression of the membrane 554 can improve the long term operation of the membrane 554 over the course of several years.

The amount of compression applied to the membrane 554 can be applied reliably without dependence on human determinations because the amount of compression applied to the membrane 554 is established by the dimensions of the implant 500 parts, not by a determination made by a human during assembly. By way of example, the longitudinal distance 568 between the shelf 548 and the proximal end of the slot 550 can be about 235 microns. The distal seal member 558 can have a longitudinal thickness 570 of about 65 microns. The proximal seal member 556 can have a longitudinal thickness 572 of about 50 microns. The retainer 532 can have a longitudinal thickness of about 25 microns. A membrane 554 with a longitudinal thickness of about 125 microns can be compressed to a longitudinal thickness 566 of about 95 microns (or less), and a retainer 532 having a longitudinal thickness 574 of about 25 microns can be inserted to maintain the membrane 554 in the compressed form. Accordingly, the dimensions of the respective parts dictate that the membrane 554 will be compressed by 30 microns, from a thickness of 125 microns to a thickness of 95 microns.

Figure 17:
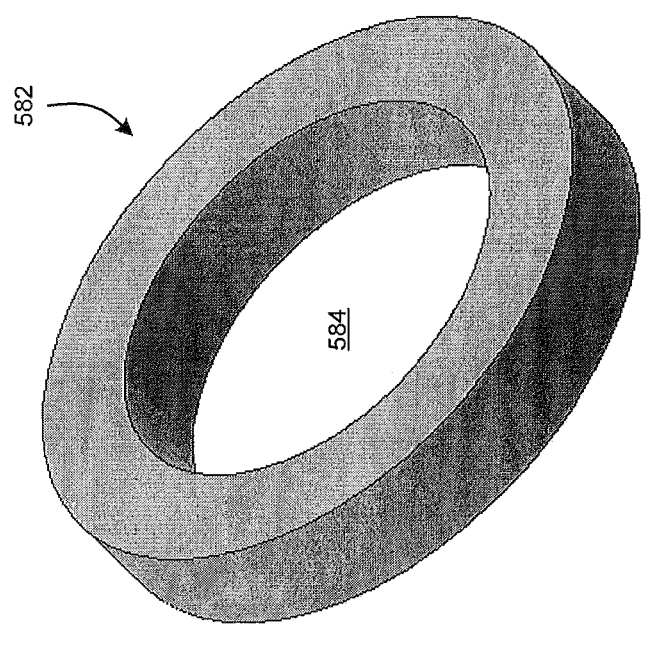
FIG. 17 is a perspective view of an example embodiment of a proximal seal member for use with a drug delivery ocular implant.
Figure 16:
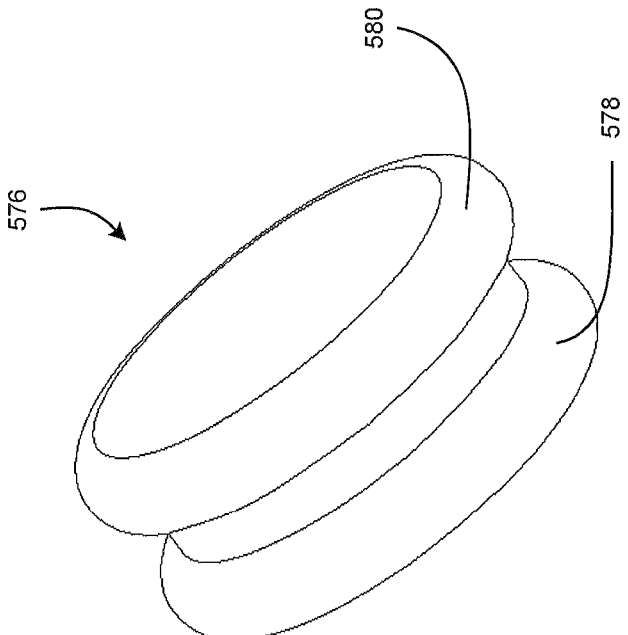
FIG. 16 is a perspective view of an example embodiment of a seal for use with a drug delivery ocular implant.

Many variations are possible. For example, FIG. 16 shows a perspective view of an example embodiment of an alternative seal 576, which can be used in place of the seal 528, in some embodiments. The seal 576 can be a single integral piece, and can be formed of a resilient material (e.g., silicone) that is impermeable or substantially impermeable to the drug. The seal 576 can include a distal bulge 578 and a proximal bulge 580, both of which can be configured to seal against the inside wall of the internal chamber 508. FIG. 17 is a perspective view of an example embodiment of an alternative upper seal member 582, which can be used in place of the upper seal member 556 discussed herein. The upper seal member 582 is generally annular or ring-shaped. The upper seal member 582 includes a single, relatively large hole 584 instead of the two relatively smaller holes 560 of the upper seal member 556 discussed herein. The larger hole 584 can produce a faster elution rate than the two smaller holes 560. Similarly, the size and number of holes in the distal seal member 552 can affect, at least in part, the elution rate of the drug. The implant 500 can be configured to have an elution rate of less than or equal to about 100 nanograms per day, less than or equal to about 75 nanograms per day, less than or equal to about 50 nanograms per day, less than or equal to about 40 nanograms per day, less than or equal to about 30 nanograms per day, less than or equal to about 25 nanograms per day, less than or equal to about 20 nanograms per day, at least about 10 nanograms per day, at least about 15 nanograms per day, at least about 20 nanograms per day, at least about 25 nanograms per day, at least about 30 nanograms per day, and/or at least about 40 nanograms per day, although values outside these ranges may be used, in some embodiments. The elution rate can be between about 15 nanograms per day and about 35 nanograms per day, or between about 20 nanograms per day and about 30 nanograms per day. The elusion rate, in some cases, can be about 25 nanograms per day. The elution rate and volume of the drug can provide drug delivery for a time period of at least about 1 year, at least about 2 year, at least about 3 year, at least about 4 years, at least about 5 years, at least about 6 year, at least about 7 years, at least about 8 years, at least about 9 years, at least about 10 years, less than or equal to about 15 years, less than or equal to about 12 years, less than or equal to about 10 years, less than or equal to about 8 years, less than or equal to about 6 years, and/or less than or equal to about 4 years, although values outside there ranges can be used in some embodiments.

Drug delivery ocular implants can be made to hold a variety of different drug volumes. The implants can hold at least about 30 nanoliters, at least about 40 nanoliters, at least about 50 nanoliters, at least about 60 nanoliters, at least about 70 nanoliters, at least about 80 nanoliters, at least about 90 nanoliters, at least about 100 nanoliters, at least about 110 nanoliters, at least about 120 nanoliters, at least about 130 nanoliters, at least about 140 nanoliters, at least about 150 nanoliters, less than or equal to about 200 nanoliters, less than or equal to about 175 nanoliters, less than or equal to about 150 nanoliters, less than or equal to about 130 nanoliters, less than or equal to about 120 nanoliters, less than or equal to about 110 nanoliters, less than or equal to about 100 nanoliters, less than or equal to about 90 nanoliters, less than or equal to about 80 nanoliters, less than or equal to about 70 nanoliters, less than or equal to about 60 nanoliters, and/or less than about 50 nanoliters, although values outside these ranges may be used, in some embodiments. The implants can hold a volume of drug between about 40 nanoliters and about 150 nanoliters, or between about 50 nanoliters and about 120 nanoliters.

Various other embodiments disclosed herein can include a drug release element, which can be similar to or the same as the drug release elements 530 and/or 730 or the other drug release elements illustrated and discussed herein. For example, in some embodiments an ocular implant can be configured to be positioned at least partially in the supraciliary space and/or suprachoroidal space and can include a drug release element that has features similar to or the same as the drug release elements disclosed herein (e.g., the drug release elements 530 and/or 730). FIG. 18 shows a perspective view of an example embodiment of an ocular implant 900. FIG. 19 shows a side view of the example embodiment of an ocular implant 900. FIG. 20 shows a cross-sectional view of the example embodiment of an ocular implant 900. Various features of the ocular implant 900 are similar to or the same as features illustrated by, or described in connection with, FIGS. 2A-2B and as discussed above herein.

The ocular implant 900 can include an outer shell 906. The outer shell and possibly other components of the implant are preferably made from a biodegradable material. The outer shell 906 can define an interior chamber 908, which can be a drug reservoir for holding one or more drugs as discussed herein. The outer shell 906 can be configured to be implanted into the supraciliary space and/or suprachoroidal space of a patient's eye. The outer shell 906 can have a generally straight configuration, or the implant can be pre-curved to a curvature that is configured to conform generally to the supraciliary space and/or suprachoroidal space. The outer shell 906 can be flexible, in some embodiments, such as to enable the ocular implant to have a generally straight configuration when positioned in a delivery apparatus and to have a curved configuration when implanted into the eye (e.g., in the supraciliary space and/or the suprachoroidal space). The outer shell 906 can include a distal end 902, which can be tapered to facilitate insertion into the supraciliary space and/or the suprachoroidal space.

The outer shell 906 can include a proximal end portion 904, which can include a drug release element 930. In some embodiments, the proximal end portion 904 can have an increased outer diameter such that a step or ridge 905 is formed between the proximal end portion 904 and the central portion of the outer shell 906. In some embodiments, the ocular implant 900 can be inserted into the eye (e.g., into the supraciliary space and/or the suprachoroidal space) until the step or ridge 905 abuts against eye tissue adjacent to the insertion site (e.g., ciliary tissue). The step or ridge 905 can help impede over-insertion of the ocular implant 900. The ocular implant 900 can be configured to release (e.g., elute) a drug, as discussed herein, such as from the proximal end of the ocular implant 900, for example, into the anterior chamber 20. The drug release location (e.g., the proximal end) can be spaced apart from the step or ridge 905 by a distance 907 to prevent the eye tissue that is adjacent the insertion site from covering or otherwise blocking the drug release location of the ocular implant 900. By way of example, the distance can be about 25 microns, about 50 microns, about 75 microns, about 100 microns, about 150 microns, about 200 microns, about 300 microns, about 400 microns, about 500 microns, about 750 microns, about 1000 microns, about 1250 microns, about 1500 microns, or any values therebetween including ranges that are bound by any of these distances. In some embodiments, the step or ridge 905 can extend laterally outward further than shown in FIGS. 18-20. The step or ridge 905 can extend laterally outward by a distance that can be about 25 microns, about 50 microns, about 75 microns, about 100 microns, about 150 microns, about 200 microns, about 300 microns, about 400 microns, about 500 microns, about 750 microns, about 1000 microns, or any values therebetween including ranges that are bound by any of these distances.

The ocular implant 900 can include one or more retention features 910 configured to anchor the implant in place when implanted in the eye. The one or more retention features 910 can include one or more annular ribs on an outer surface of the outer shell 906. The ribs can have angled distal sides and/or can be barbed to facilitate insertion of the ocular implant 900 into the eye while impeding the ocular implant 900 from unintentionally releasing from the eye tissue. In some embodiments, the ribs can have an outer diameter that is substantially the same as the outer diameter of the proximal end portion 904, to facilitate placement in a delivery apparatus. In some embodiments, the one or more retention features 910 can be configured to engage the eye tissue that is adjacent to the insertion site. For example, the one or more retention features 910 can be on or near the proximal end portion 904 or at or near the step or ridge 905. In some embodiments, the retention features 910 can be omitted, and the outer shell 906 can be held in place by friction against the surrounding eye tissue.

The ocular implant 900 can include a drug release element 930. The drug release element can include a distal seal member 952, a membrane 954, and a proximal seal member 956, which can be the same as, or similar to, the other distal seal members, membranes, and proximal seal members discussed and illustrated herein. The disclosure provided herein for other embodiments that include a drug release element can be applied to the ocular implant 900, and is not repeated here. The membrane 954 can be compressed between the distal seal member 952 and the proximal seal member 956, as discussed herein. A retainer 932 can hold the drug release element 930 in place, as discussed herein. The outer shell 906 can include one or more slots 950, and the retainer 932 can engage the one or more slots 950 proximally of the proximal seal member 956. Two slots 950 can be positioned on opposite sides of the outer shell 906 and the retainer 930 can be inserted through one of the slots 950, across the interior chamber 908, and into the other of the slots 950. The distal seal member 952 can be seated against a shelf in the interior chamber 908. The compressed membrane 954 can apply a force that presses the distal seal member 952 against the shelf and that presses the proximal seal member 956 against the retainer 932.

It will be appreciated that the elements discussed above are not to be read as limiting the implants to the specific combinations or embodiments described. Rather, the features discussed are freely interchangeable to allow flexibility in the construction of a drug delivery implant in accordance with this disclosure.

Delivery Instruments

Another aspect of the systems and methods described herein relates to delivery instruments for implanting an implant for delivering a drug to the eye and optionally for draining fluid from the anterior chamber into a physiologic outflow space. In some embodiments, the implant is inserted into the eye from a site transocularly situated from the implantation site. The delivery instrument is sufficiently long to advance the implant transocularly from the insertion site across the anterior chamber to the implantation site. At least a portion of the instrument may be flexible. The instrument may comprise a plurality of members longitudinally moveable relative to each other. In some embodiments, the plurality of members comprises one or more slideable guide tubes. In some embodiments, at least a portion of the delivery instrument is curved. In some embodiments, a portion of the delivery instrument is rigid and another portion of the instrument is flexible.

In some embodiments, the delivery instrument has a distal curvature. The distal curvature of the delivery instrument may be characterized in some embodiments as a radius of approximately 10 to 30 mm. In some embodiments the distal curvature has a radius of about 20 mm.

Figure 7:
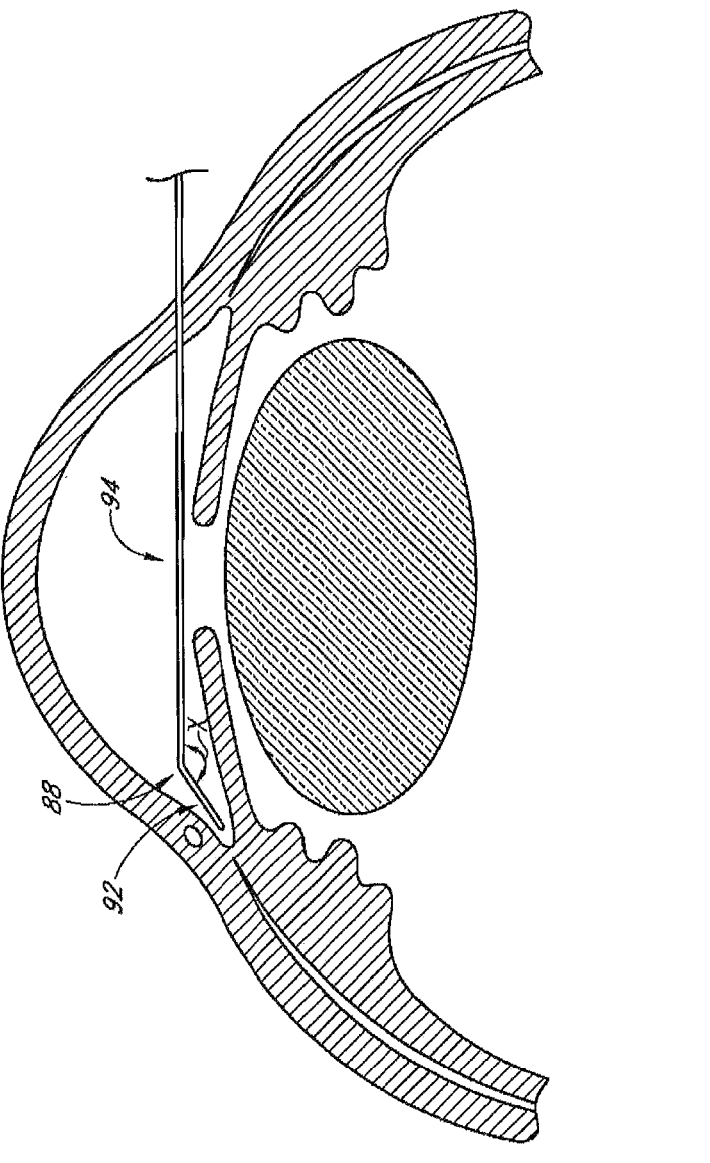
FIG. 7 illustrates an apparatus for implanting a drug delivery device in accordance with embodiments disclosed herein

In some embodiments, the delivery instrument has a distal angle 88 (with a measure denoted by $\chi$ in FIG. 7). The angle measure $\chi$ may be characterized as approximately 90 to 180 degrees relative to the proximal segment 94 of the delivery instrument. In some embodiments, the angle measure $\chi$ may be characterized as between about 145 and about 170 degrees. In some embodiments the angle measure is between about 150 and about 170 degrees, or between about 155 and about 165 degrees. The angle can incorporate a small radius of curvature at the "elbow" so as to make a smooth transition from the proximal segment of the delivery instrument to the distal segment. The length of the distal segment may be approximately 0.5 to 7 mm in some embodiments, while in some other embodiments, the length of the distal segment is about 2 to 3 mm.

In other embodiments, a curved distal end is usually preferred. In such embodiments, the height of the delivery instrument/shunt assembly (dimension 90 in FIG. 8) is less than about 3 mm in some embodiments, and less than 2 mm in other embodiments.

In some embodiments, the instruments have a sharpened feature at the forward end and are self-trephinating, i.e., self-penetrating, so as to pass through tissue without pre-forming an incision, hole or aperture. In some embodiments, instruments that are self-trephinating are configured to penetrate the tissues of the cornea and/or limbus only. In other embodiments, instruments that are self-trephinating are configured to penetrate internal eye tissues, such as those in the anterior chamber angle, in order to deliver an implant. Alternatively, a separate trocar, scalpel, spatula, or similar instrument can be used to pre-form an incision in the eye tissue (either the cornea/sclera or more internal tissues) before passing the implant into such tissue. In some embodiments, the implant is blunt at the distal end, to aid in blunt dissection (and hence reduce risk of tissue trauma) of the ocular tissue. In other embodiments, however, the implant is also sharpened, tapered or otherwise configured to penetrate ocular tissues to aid in implantation.

For delivery of some embodiments of the drug eluting ocular implant, the instrument has a sufficiently small cross section such that the insertion site self seals without suturing upon withdrawal of the instrument from the eye. An outer dimension of the delivery instrument is preferably no greater than about 18 gauge and is not smaller than about 27 or 30 gauge.

For delivery of some embodiments of the drug eluting ocular implant, an incision in the corneal tissue is made with a hollow needle through which the implant is passed. The needle has a small diameter size (e.g., 18 or 19 or 20 or 21 or 22 or 23 or 24 or 25 or 26 or 27 gauge) so that the incision may be self sealing and the implantation occurs in a closed chamber with or without viscoelastic. A self-sealing incision may also be formed using a conventional "tunneling" procedure in which a spatula-shaped scalpel is used to create a generally inverted V-shaped incision through the cornea. In a preferred mode, the instrument used to form the incision through the cornea remains in place (that is, extends through the corneal incision) during the procedure and is not removed until after implantation. Such incision-forming instrument either may be used to place the ocular implant or may cooperate with a delivery instrument to allow implantation through the same incision without withdrawing the incision-forming instrument. Of course, in other modes, various surgical instruments may be passed through one or more corneal incisions multiple times.

Some embodiments include a spring-loaded pusher system. In some embodiments, the spring-loaded pusher includes a button operably connected to a hinged rod device. The rod of the hinged rod device engages a depression in the surface of the pusher, keeping the spring of the pusher in a compressed conformation. When the user pushes the button, the rod is disengaged from the depression, thereby allowing the spring to decompress, thereby advancing the pusher forward.

In some embodiments, an over-the wire system is used to deliver the implant. The implant may be delivered over a wire. In some embodiments, the wire is self-trephinating. The wire may also function as a trocar. The wire may be superelastic, flexible, or relatively inflexible with respect to the implant. The wire may be pre-formed to have a certain shape. The wire may be curved. The wire may have shape memory, or be elastic. In some embodiments, the wire is a pull wire. The wire may also be a steerable catheter.

In some embodiments, the wire is positioned within a lumen in the implant. The wire may be axially movable within the lumen. The lumen may or may not include valves or other flow regulatory devices.

In some embodiments, the delivery instrument is a trocar. The trocar may be angled or curved. In some embodiments, the trocar is flexible. In other embodiments the trocar is relatively rigid. In other embodiments, the trocar is stiff. In embodiments where the trocar is stiff, the implant is relatively flexible. The diameter of the trocar is about 0.001 inches to about 0.01 inches. In some embodiments, the diameter of the trocar is 0.001, 0.002, 0.003, 0.004, 0.005, 0.006, 0.007, 0.008, 0.009, or 0.01 inches.

In some embodiments, delivery of the implant is achieved by applying a driving force at or near the proximal end of the implant. The driving force may be a pulling or a pushing applied to the end of the implant.

The instrument may include a seal or coating to prevent aqueous humor from passing through the delivery instrument and/or between the members of the instrument when the instrument is in the eye. The seal aids in preventing backflow. In some embodiments, the instrument is coated with the coating and a hydrophilic or hydrophobic agent. In some embodiments, one region of the instrument is coated with the coating plus the hydrophilic agent, and another region of the instrument is coated with the coating plus the hydrophobic agent. The delivery instrument may additionally comprise a seal between various members comprising the instrument. The seal may comprise a hydrophobic or hydrophilic coating between slip-fit surfaces of the members of the instrument. The seal may be disposed proximate of the implant when carried by the delivery instrument. In some embodiments, the seal is present on at least a section of each of two devices that are machined to closely fit with one another.

The delivery instrument may be configured to deliver multiple implants. In some such embodiments, the implants may be arranged in tandem (or serially for implant numbers greater than two) within the device.

In some embodiments, the delivery device has a substantially straight needle or cannula having a sharpened tip and measuring from about 21-30 gauge, including 23-25 gauge, and/or having an inner diameter of about 0.15-0.45 mm including 0.25-0.35 mm. The needle or cannula is operatively connected to a handpiece having a trigger, plunger, or actuator that, when operated, causes the expulsion of the implant from the distal end of the delivery device. The implant is preferably preloaded into the delivery device by the manufacturer.

Procedures

For delivery of some embodiments of the ocular implant, the implantation occurs in a closed chamber with or without viscoelastic.

The implants may be placed using an applicator, such as a pusher, or they may be placed using a delivery instrument having energy stored in the instrument, such as disclosed in U.S. Pat. No. 7,331,984, issued Feb. 19, 2008, the entirety of which is incorporated herein by reference and made a part of this specification and disclosure. In some embodiments, fluid may be infused through an applicator to create an elevated fluid pressure at the forward end of the implant to ease implantation.

In one embodiment of the invention, a delivery apparatus (or "applicator") similar to that used for placing a trabecular stent through a trabecular meshwork of an eye is used. Certain embodiments of such a delivery apparatus are disclosed in U.S. Pat. No. 7,331,984, issued Feb. 19, 2008; U.S. Publication No. 2002/0133168, entitled APPLICATOR AND METHODS FOR PLACING A TRABECULAR SHUNT FOR GLAUCOMA TREATMENT; and U.S. Provisional Application No. 60/276,609, filed Mar. 16, 2001, entitled APPLICATOR AND METHODS FOR PLACING A TRABECULAR SHUNT FOR GLAUCOMA TREATMENT, each of which is incorporated by reference in its entirety and made a part of this specification and disclosure.

In one embodiment, the delivery apparatus 2000 includes a handpiece, an elongate tip, a holder and an actuator, which are schematically depicted in FIG. 6C. The handpiece 1000 has a distal end 1002 and a proximal end 1004. The elongate tip 1010 is connected to the distal end of the handpiece. The elongate tip has a distal portion and is configured to be placed through a corneal incision and into an anterior chamber of the eye. The holder 1020 (e.g., an insertion tube) is attached to the distal portion of the elongate tip. The holder is configured to hold and release the drug delivery implant. The actuator 1040 is on the handpiece and actuates the holder to release the drug delivery implant from the holder. In one embodiment, a deployment mechanism within the delivery apparatus includes a push-pull type plunger.

In some embodiments, the holder comprises a clamp. In some embodiments, the apparatus further comprises a spring within the handpiece that is configured to be loaded when the drug delivery implant is being held by the holder, the spring being at least partially unloaded upon actuating the actuator, allowing for release of the drug delivery implant from the holder. In various embodiments, the clamp comprises a plurality of claws configured to exert a clamping force onto at least the proximal portion of the drug delivery implant. The holder may also comprise a plurality of flanges.

In some embodiments, the distal portion of the elongate tip is made of a flexible material. This can be a flexible wire. The distal portion can have a deflection range, preferably of about 45 degrees from the long axis of the handpiece. The delivery apparatus can further comprise an irrigation port in the elongate tip.

In some embodiments, the method includes using a delivery apparatus that comprises a handpiece having a distal end and a proximal end and an elongate tip connected to the distal end of the handpiece. The elongate tip has a distal portion and being configured to be placed through a corneal incision and into an anterior chamber of the eye. The apparatus further has a holder attached to the distal portion of the elongate tip, the holder being configured to hold and release the drug delivery implant, and an actuator on the handpiece that actuates the holder to release the drug delivery implant from the holder.

The delivery instrument may be advanced through an insertion site in the cornea and advanced either transocularly or posteriorly into the anterior chamber angle and positioned at base of the anterior chamber angle. Using the anterior chamber angle as a reference point, the delivery instrument can be advanced further in a generally posterior direction to drive the implant into the iris, inward of the anterior chamber angle.

Optionally, based on the implant structure, the implant may be laid within the anterior chamber angle, taking on a curved shape to match the annular shape of the anterior chamber angle.

In some embodiments, the implant may be brought into position adjacent the tissue in the anterior chamber angle or the iris tissue, and the pusher tube advanced axially toward the distal end of the delivery instrument. As the pusher tube is advanced, the implant is also advanced. When the implant is advanced through the tissue and such that it is no longer in the lumen of the delivery instrument, the delivery instrument is retracted, leaving the implant in the eye tissue.

The placement and implantation of the implant may be performed using a gonioscope or other conventional imaging equipment. In some embodiments, the delivery instrument is used to force the implant into a desired position by application of a continual implantation force, by tapping the implant into place using a distal portion of the delivery instrument, or by a combination of these methods. Once the implant is in the desired position, it may be further seated by tapping using a distal portion of the delivery instrument.

Figure 9:
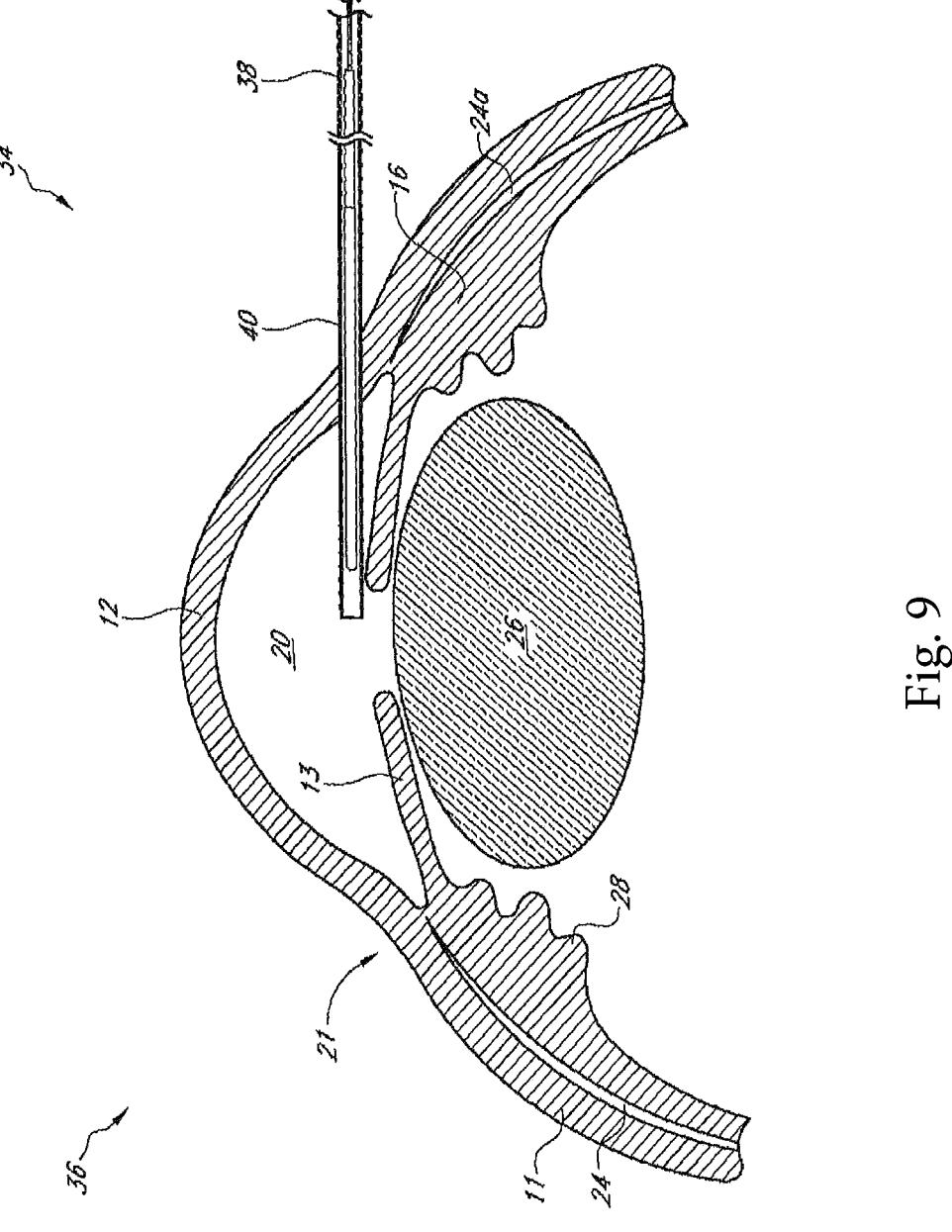
FIG. 9 illustrates a schematic cross-sectional view of an eye with a delivery device containing an implant being advanced across the anterior chamber. The size of the implant is exaggerated for illustration purposes.

FIG. 9 illustrates one embodiment of a surgical method for implanting the drug delivery implant into an eye, as described in the embodiments herein. A first incision or slit is made through the conjunctiva and the sclera 11 at a location rearward of the limbus 21, that is, posterior to the region of the sclera 11 at which the opaque white sclera 11 starts to become clear cornea 12. In some embodiments, the first incision is posterior to the limbus 21, including about 3 mm posterior to the limbus. In some embodiments, the incision is made such that a surgical tool may be inserted into the anterior chamber at a shallow angle (relative to the anteroposterior axis), as shown in FIG. 9. In other embodiments, the first incision may be made to allow a larger angle of instrument insertion (see, e.g. FIGS. 10-12). Also, the first incision is made slightly larger than the width of the drug delivery implant. In one embodiment, a conventional cyclodialysis spatula may be inserted through the first incision into the supraciliary space to confirm correct anatomic position.

A portion of the upper and lower surfaces of the drug delivery implant can be grasped securely by the surgical tool, for example, a forceps, so that the forward end of the implant is oriented properly. The implant may also be secured by viscoelastic or mechanical interlock with the pusher tube or wall of the implant delivery device. In one embodiment, the implant is oriented with a longitudinal axis of the implant being substantially co-axial to a longitudinal axis of the grasping end of the surgical tool. The drug delivery implant is disposed through the first incision.

The delivery instrument may be advanced from the insertion site transocularly into the anterior chamber angle and positioned at a location near the scleral spur. Using the scleral spur as a reference point, the delivery instrument can be advanced further in a generally posterior direction to drive the implant into eye tissue at a location just inward of the scleral spur toward the iris.

Optionally, based on the implant structure, the shearing edge of the insertion head of the implant can pass between the scleral spur and the ciliary body 16 posterior to the trabecular meshwork.

The drug delivery implant may be continually advanced posteriorly until a portion of its insertion head and the first end of the conduit is disposed within the anterior chamber 20 of the eye. Thus, the first end of the conduit is placed into fluid communication with the anterior chamber 20 of the eye. The distal end of the elongate body of the drug delivery implant can be disposed into the suprachoroidal space of the eye so that the second end of the conduit is placed into fluid communication with the suprachoroidal space. Alternatively, the implant may be brought into position adjacent the tissue in the anterior chamber angle, and the pusher tube advanced axially toward the distal end of the delivery instrument. As the pusher tube is advanced, the implant is also advanced. When the implant is advanced through the tissue and such that it is no longer in the lumen of the delivery instrument, the delivery instrument is retracted, leaving the implant in the eye tissue.

The placement and implantation of the implant may be performed using a gonioscope or other conventional imaging equipment. In some embodiments, the delivery instrument is used to force the implant into a desired position by application of a continual implantation force, by tapping the implant into place using a distal portion of the delivery instrument, or by a combination of these methods. Once the implant is in the desired position, it may be further seated by tapping using a distal portion of the delivery instrument.

In one embodiment, the drug delivery implant is sutured to a portion of the sclera 11 to aid in fixating the implant. In one embodiment, the first incision is subsequently sutured closed. As one will appreciate, the suture used to fixate the drug delivery implant may also be used to close the first incision. In another embodiment, the drug delivery implant is held substantially in place via the interaction of the implant body's outer surface and the tissue of the sclera 11 and ciliary body 16 and/or choroid 12 without suturing the implant to the sclera 11. Additionally, in one embodiment, the first incision is sufficiently small so that the incision self-seals upon withdrawal of the surgical tool following implantation of the drug delivery implant without suturing the incision.

As discussed herein, in some embodiments the drug delivery implant additionally includes a shunt comprising a lumen configured provide a drainage device between the anterior chamber 20 and the suprachoroidal space. Upon implantation, the drainage device may form a cyclodialysis with the implant providing a permanent, patent communication of aqueous humor through the shunt along its length. Aqueous humor is thus delivered to the suprachoroidal space where it can be absorbed, and additional reduction in pressure within the eye can be achieved.

Figure 10:
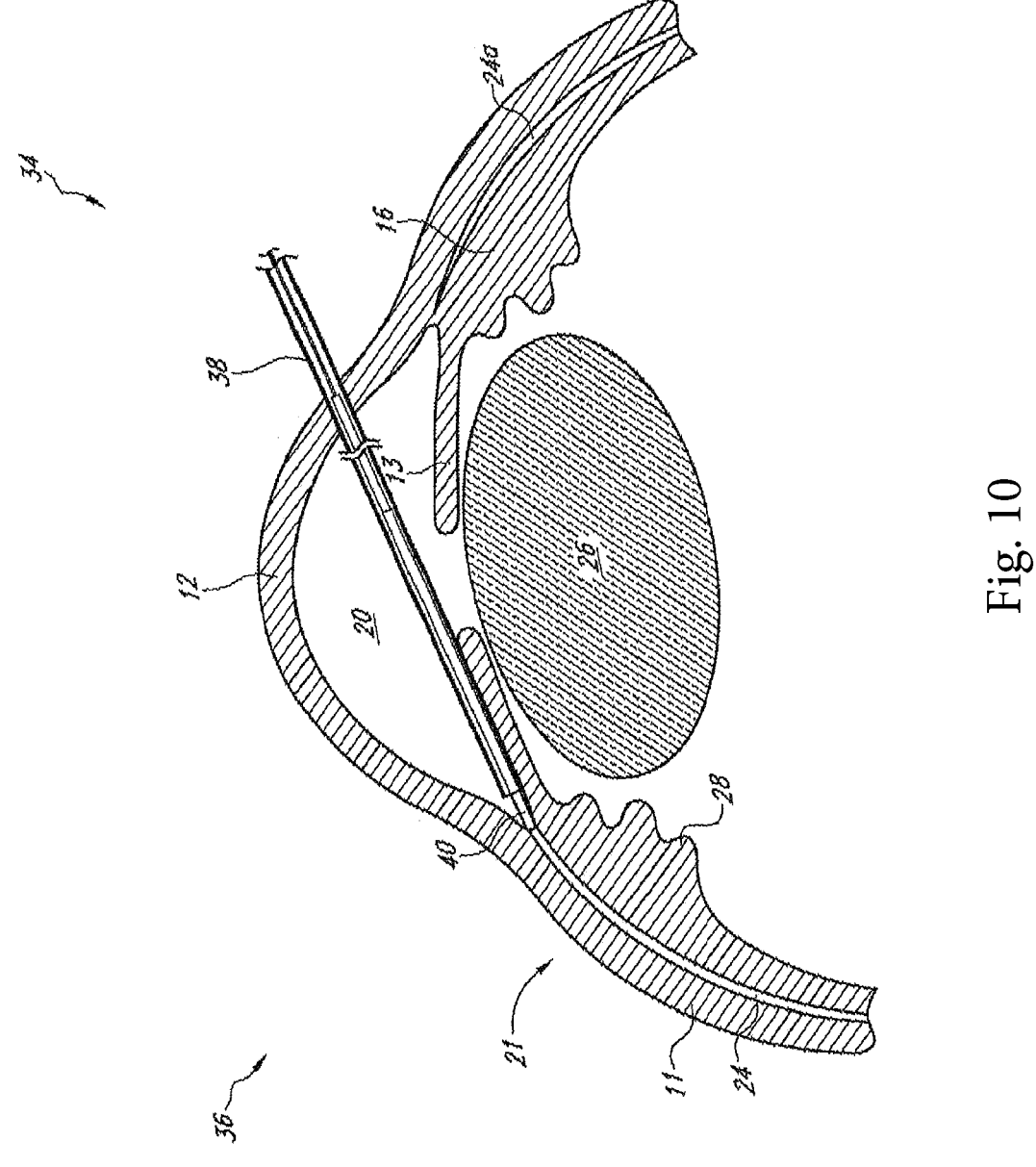
FIG. 10 illustrates an additional implantation procedure according to several embodiments disclosed herein. The size of the implant is exaggerated for illustration purposes.
Figure 11:
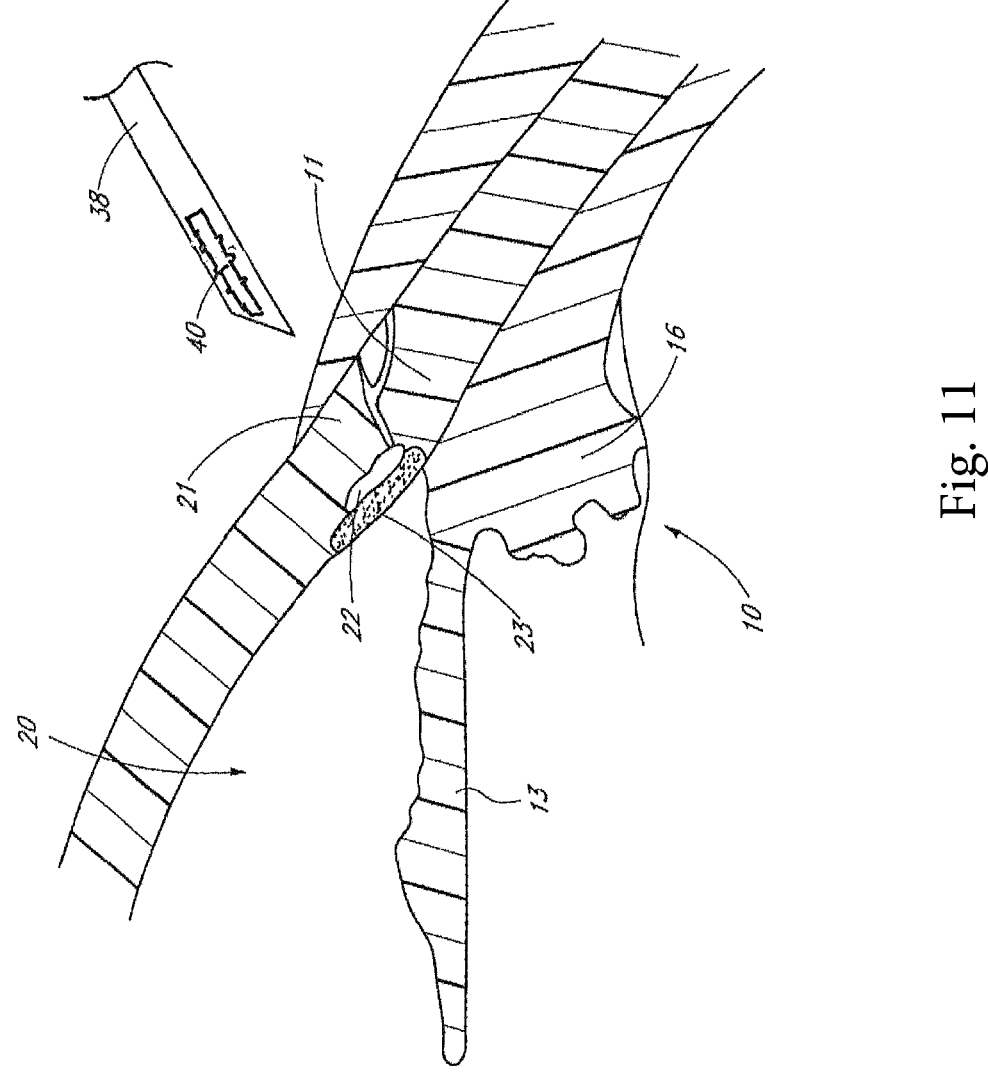
FIG. 11 illustrates a schematic cross-sectional view of an eye with a delivery device being advanced adjacent the anterior chamber angle. The size of the implant is exaggerated for illustration purposes.

In some embodiments it is desirable to deliver the drug delivery implant ab interno across the eye, through a small incision at or near the limbus (FIG. 10). The overall geometry of the system makes it advantageous that the delivery instrument incorporates a distal curvature (as in FIG. 8), or a distal angle (as in FIG. 7). In the former case, the drug delivery implant may be flexible to facilitate delivery along the curvature or may be more loosely held to move easily along an accurate path. In the latter case, the implant may be relatively rigid. The delivery instrument may incorporate an implant advancement element (e.g. pusher) that is flexible enough to pass through the distal angle.

Figure 12:
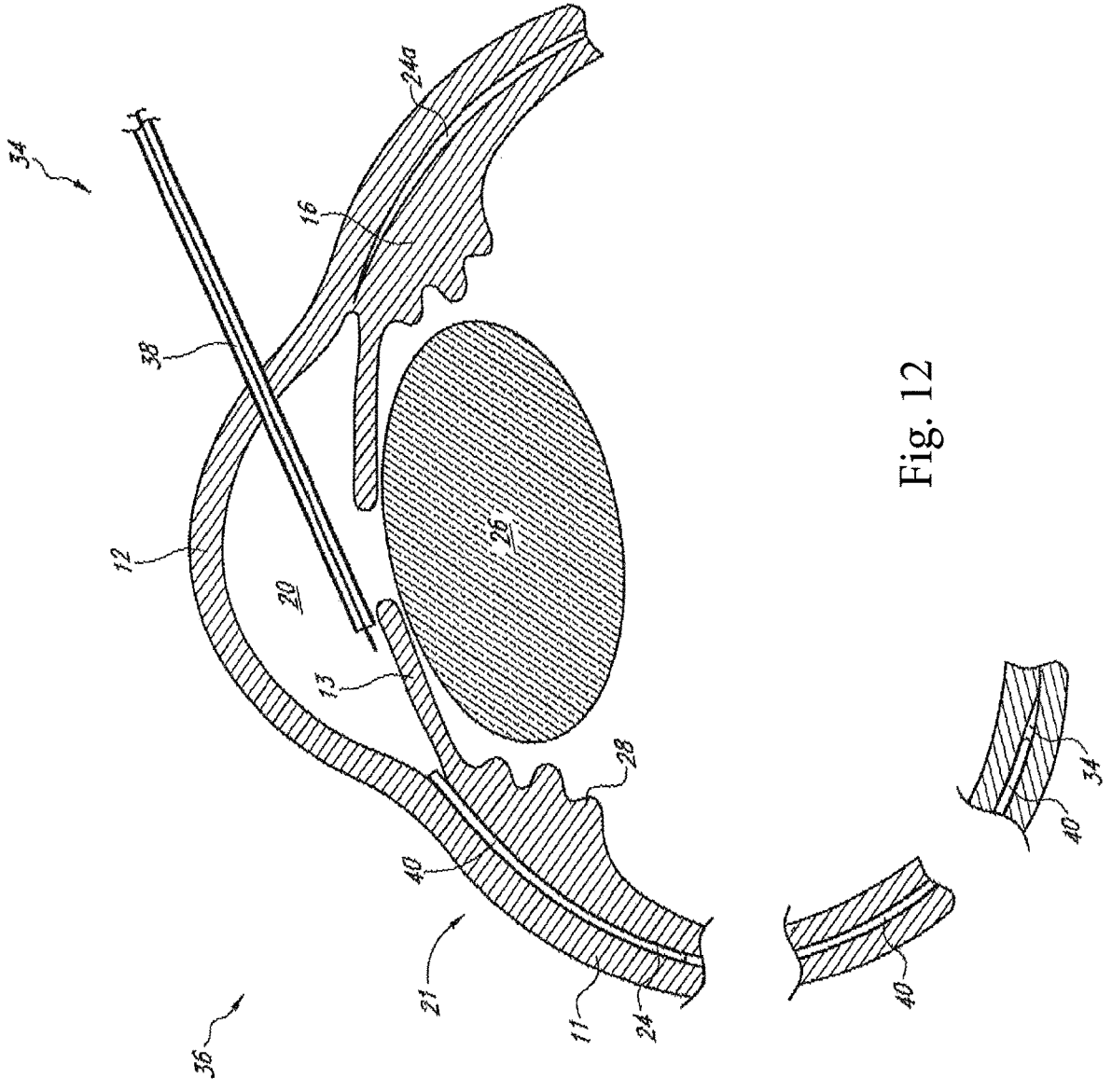
FIG. 12 illustrates a schematic cross-section view of an eye with a delivery device implanting an implant that extends from the anterior chamber through the suprachoroidal space and terminates in close proximity to the macula.

In some embodiments, the implant and delivery instrument are advanced together through the anterior chamber 20 from an incision at or near the limbus 21, across the iris 13, and through the ciliary muscle attachment until the drug delivery implant outlet portion is located in the uveoscleral outflow pathway (e.g. exposed to the suprachoroidal space defined between the sclera 11 and the choroid 12). FIG. 10 illustrates a transocular implantation approach that may be used with the delivery instrument inserted well above the limbus 21. In other embodiments (see, e.g., FIG. 11), the incision may be made more posterior and closer to the limbus 21. In one embodiment, the incision will be placed on the nasal side of the eye with the implanted location of the drug delivery implant 40 on the temporal side of the eye. In another embodiment, the incision may be made temporally such that the implanted location of the drug delivery implant is on the nasal side of the eye. In some embodiments, the operator simultaneously pushes on a pusher device while pulling back on the delivery instrument, such that the drug delivery implant outlet portion maintains its location in the posterior region of the suprachoroidal space near the macula 34, as illustrated in FIG. 12. The implant is released from the delivery instrument, and the delivery instrument retracted proximally. The delivery instrument is withdrawn from the anterior chamber through the incision.

In some embodiments, it is desirable to implant a drug delivery implant with continuous aqueous outflow through the fibrous attachment zone, thus connecting the anterior chamber 20 to the uveoscleral outflow pathway, in order to reduce the intraocular pressure in glaucomatous patients. In some embodiments, it is desirable to deliver the drug delivery implant with a device that traverses the eye internally (ab interno), through a small incision in the limbus 21.

In several embodiments, microinvasive methods of implanting a drug delivery implant are provided. In several such embodiments, an ab externo technique is utilized. In some embodiments, the technique is non-penetrating, thereby limiting the invasiveness of the implantation method. As discussed herein, in some embodiments, the drug delivery device that is implanted comprises a shunt. In some embodiments, such implants facilitate removal of fluid from a first location, while simultaneously providing drug delivery. In some embodiments, the implants communicate fluid from the anterior chamber to the suprachoroidal space, which assists in removing fluid (e.g., aqueous humor) from and reducing pressure increases in the anterior chamber.

Figure 8:
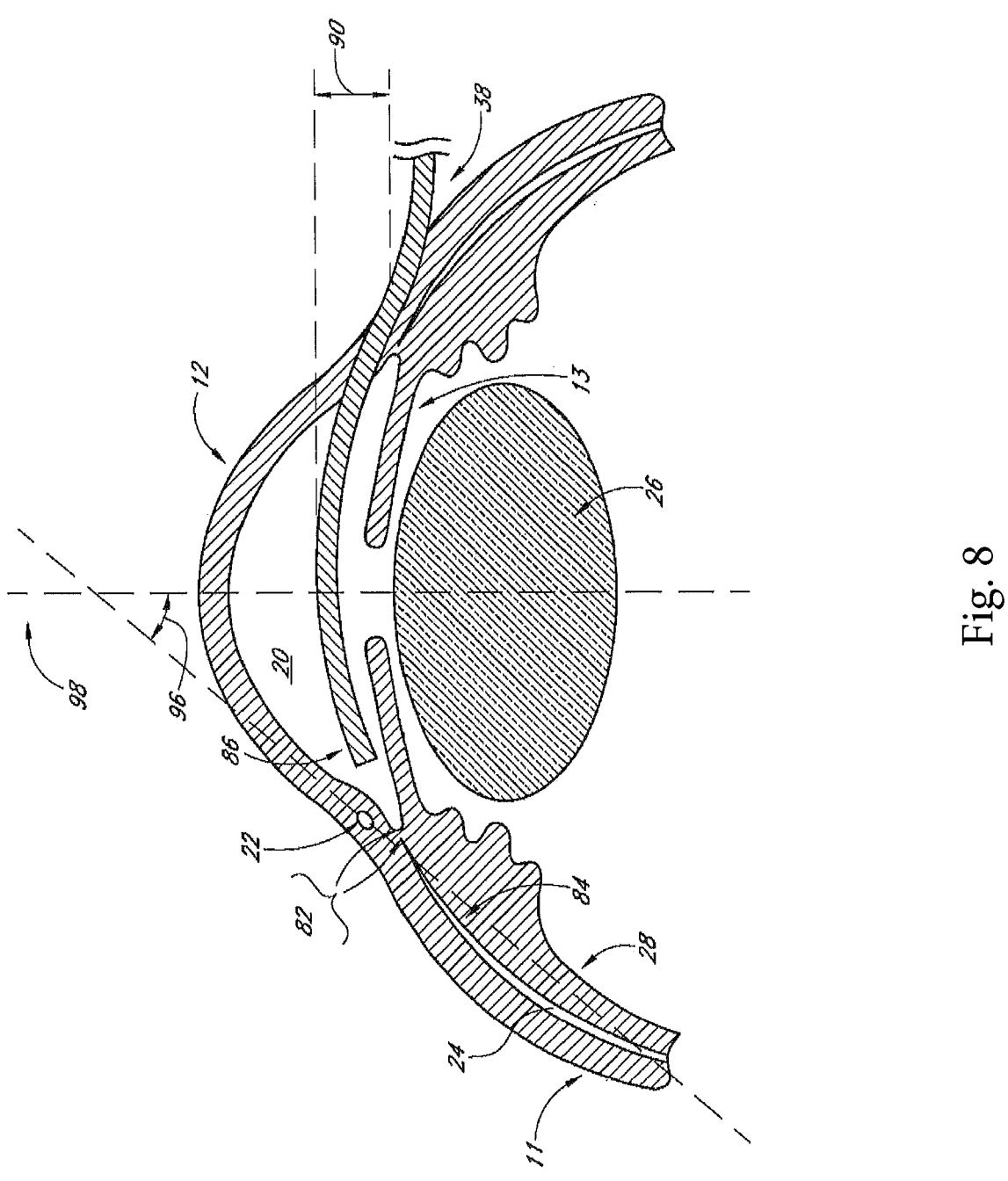
FIG. 8 illustrates an apparatus for implanting a drug delivery device in accordance with embodiments disclosed herein.

FIG. 8 shows a meridional section of the anterior segment of the human eye and schematically illustrates another embodiment of a delivery instrument 38 that may be used with embodiments of drug delivery implants described herein. In FIG. 8, arrows 82 show the fibrous attachment zone of the ciliary muscle 84 to the sclera 11. The ciliary muscle 84 is coextensive with the choroid 28. The suprachoroidal space is the interface between the choroid 28 and the sclera 11. Other structures in the eye include the lens 26, the cornea 12, the anterior chamber 20, the iris 13, and Schlemm's canal 22.

The delivery instrument/implant assembly can be passed between the iris 13 and the cornea 12 to reach the iridocorneal angle. Therefore, the height of the delivery instrument/shunt assembly (dimension 90 in FIG. 8) is less than about 3 mm in some embodiments, and less than 2 mm in other embodiments.

The suprachoroidal space between the choroid 28 and the sclera 11 generally forms an angle 96 of about 55° with the optical axis 98 of the eye. This angle, in addition to the height requirement described in the preceding paragraph, are features to consider in the geometrical design of the delivery instrument/implant assembly.

The overall geometry of the drug delivery implant system makes it advantageous that the delivery instrument 38 incorporates a distal curvature 86, as shown in FIG. 8, a distal angle, or a combination thereof. The distal curvature (FIG. 9) is expected to pass more smoothly through the corneal or scleral incision at the limbus. In this embodiment, the drug delivery implant may be curved or flexible. Alternatively, the drug delivery implant may be mounted on a straight segment of the delivery instrument, distal of an "elbow" or angle. In this case, the drug delivery implant may be straight and relatively inflexible, and the delivery instrument may incorporate a delivery mechanism that is flexible enough to advance through the angle. In some embodiments, the drug delivery implant may be a rigid tube, provided that the implant is no longer than the length of the distal segment.

The distal curvature 86 of delivery instrument 38 may be characterized as a radius of between about 10 to 30 mm in some embodiments, and about 20 mm in certain embodiments. The distal angle of a delivery instrument in an embodiment having a straight section and a single angle near the distal end may be characterized as between about 90 to 170 degrees relative to an axis of the proximal segment 94 of the delivery instrument. In other embodiments, the angle may be between about 145 and about 170 degrees. The angle incorporates a small radius of curvature at the "elbow" so as to make a smooth transition from the proximal segment 94 of the delivery instrument to the distal segment 92. The length of the distal segment 92 may be approximately 0.5 to 7 mm in some embodiments, and about 2 to 3 mm in certain embodiments.

In some embodiments, a viscoelastic, or other fluid is injected into the suprachoroidal space to create a chamber or pocket between the choroid and sclera which can be accessed by a drug delivery implant. Such a pocket exposes more of the choroidal and scleral tissue area, provides lubrication and protection for tissues during implantation, and increases uveoscleral outflow in embodiments where the drug delivery implant includes a shunt, causing a lower intraocular pressure (TOP). In some embodiments, the viscoelastic material is injected with a 25 or 27G cannula, for example, through an incision in the ciliary muscle attachment or through the sclera (e.g. from outside the eye). The viscoelastic material may also be injected through the implant itself either before, during or after implantation is completed.

In some embodiments, a hyperosmotic agent is injected into the suprachoroidal space. Such an injection can delay TOP reduction. Thus, hypotony may be avoided in the acute postoperative period by temporarily reducing choroidal absorption. The hyperosmotic agent may be, for example glucose, albumin, HYPAQUE™ medium, glycerol, or poly (ethylene glycol). The hyperosmotic agent can breakdown or wash out as the patient heals, resulting in a stable, acceptably low TOP, and avoiding transient hypotony.

In some embodiments, the distal portion of the delivery device is sharpened like a needle such that it can make an opening in the sclera of the eye and allow for the direct placement of an implant, for example those in FIGS. 4A-C, into the vitreous cavity of an eye, following the pushing or pressing of a plunger or actuator on the handpiece that causes the implant to be expelled from the distal end of the device. In such embodiments, a straight needle or cannula may be preferred to deliver the implant.

Controlled Drug Release

The drug delivery implants as described herein, function to house a drug and provide drug elution from the implant in a controlled fashion, based on the design of the various components of the implant, for an extended period of time. Various elements of the implant composition, implant physical characteristics, implant location in the eye, and the composition of the drug work in combination to produce the desired drug release profile.

As described above, in several embodiments the drug delivery implant is made from one or more biodegradable materials that degrade, such as by bioerosion, bioresorption, or bioabsorption, following implantation in the eye and the delivery of all or substantially all of the drug. Such materials may be permeable, semi-permeable or impermeable to the drug being delivered from the device. The material may be formulated or manufactured to be porous or substantially non-porous. Suitable biodegradable materials may optionally possess one or more other physical characteristics such as flexibility, hydrophilicity, hydrophobicity, elasticity, and the like.

In some embodiments, the implant is engineered to control the rate of drug release from the device. In some such embodiments, the outer shell of the device substantially wholly controls the rate of drug delivery. In other such embodiments, the outer shell controls part of the rate of drug delivery, with the remainder being controlled by drug-permeable membranes which may be part of one or more membrane-cap systems, such as a drug release element as described above. In other embodiments, one or more membrane-cap systems substantially or wholly control the rate of drug delivery.

Biodegradable materials suitable for making the implant and components thereof include, but are not limited to, the following: poly(esters), poly(ester amide) (PEA), poly(ester carbonate) (PEC), polylactide (PLA), poly(L-lactide) (PLLA), poly(D-lactide) (PDLA), poly(DL-lactic acid) (PDLLA), polyglycolide (PGA), polycaprolactone (PCL), copolymers such as polylactideco-glycolide (PLGA), poly (hydroxyalkanoate)s, poly(3-hydroxybutyrate) (PHB), PHB copolymerized with 3-hydroxyvalerate (PHBV), Poly(propylene fumarate) (PPF), poly-(acid anhydride) (PAA), poly(butylene succinate) (PBS), poly(ethylene succinate) (PES), poly(hydroxyalkanoate) (PHA), poly(cyanoacrylate) (PCA), polyacetals, polyorthoesters (POE), polycarbonates including poly(trimethylene carbonate) (PTMC), polyphosphazenes, polyphosphoesters, and blends, copolymers, and combinations of the foregoing; and natural polymers, including but not limited to, modified poly(saccharide)s, e.g., starch, cellulose, and chitosan.

Materials may be coated, on the inner and/or outer sides, in all or in part of either or both sides. A coating may serve any of a variety of purposes including, but not limited to, altering the elution rate of the drug through a material (either accelerating or retarding the elution rate), altering the degradation rate of the material (either accelerating or retarding the degradation rate), altering water resistance or permeability (either increasing or decreasing resistance or permeability), or other properties. Coatings are preferably biodegradable.

The coating may be any suitable material including, but not limited to, poly(lactic acid), polyethylene-vinyl acetate, poly(lactic-co-glycolic acid), poly(D,L-lactide), poly(D,L-lactide-co-trimethylene carbonate), collagen, heparinized collagen, poly(caprolactone), poly(glycolic acid), and/or other polymer or copolymer. Suitable atomic or inorganic materials may also be used. As discussed above, the various materials, coasting and mechanisms to tailor the elution profile of drug from the device can be applied to any type of implant disclosed herein, including those for placement within the eye and those for placement within the punctum. Likewise, the use of bioerodible materials for the body of the implant can be used for implants for placement within the eye and for those for placement within the punctum. Whether placed in the eye or in the punctum, the ability of the implant to substantially or completely erode is advantageous, in several embodiments. In some embodiments, erosion of the implant occurs after all or substantially all the drug(s) has been released from the implant. In some embodiments, erosion of the implant overlaps with at least a portion of the drug release. In some embodiments, erosion of the implant occurs concurrently with drug release such that when all or substantially all the drug(s) has been released from the implant, the implant is substantially eroded.

In some ocular disorders, therapy may require a defined kinetic profile of administration of drug to the eye, such as zero-order release or pseudo zero-order release. It will be appreciated from the above discussion of various embodiments that the ability to tailor the release rate of a drug from the implant can similarly be used to accomplish achieve a desired kinetic profile. For example the composition of the outer shell and any polymer coatings can be manipulated to provide a particular kinetic profile of release of the drug. Additionally, the design of the implant itself, including the thickness of the shell material, and the existence and composition of any caps, including drug release elements, are among the ways to provide a means to create a particular drug release profile. Likewise, the use of PLGA copolymers and/or other controlled release materials and excipients, may provide particular kinetic profiles of release of the compounded drug. In certain embodiments, zero-order release of a drug may be achieved by manipulating any of the features and/or variables discussed above alone or in combination.

In conjunction with the controlled release of a drug to a target tissue, certain doses of a drug (or drugs) are desirable over time, in certain embodiments. As such, in some embodiments, the total drug load delivered to a target tissue over the lifetime of an implant ranges from about 10 to about 1000 µg. In certain embodiments the total drug load ranges from about 100 to about 900 µg, from about 200 to about 800 µg, from about 300 to about 700 µg, or from about 400 to about 600 µg. In some embodiments, the total drug load ranges from about 10 to about 300 µg, from about 10 to about 500 µg, or about 10 to about 700 µg. In other embodiments, total drug load ranges from about 200 to about 500 µg, from 400 to about 700 µg or from about 600 to about 1000 µg. In still other embodiments, total drug load ranges from about 200 to about 1000 µg, from about 400 to about 1000 µg, or from about 700 to about 1000 µg. In some embodiments total drug load ranges from about 500 to about 700 µg, about 550 to about 700 µg, or about 550 to about 650 µg, including 575, 590, 600, 610, and 625 µg. It shall be appreciated that additional ranges of drugs bordering, overlapping or inclusive of the ranges listed above are also used in certain embodiments.

Similarly, in other embodiments, controlled drug delivery is calculated based on the elution rate of the drug from the implant. In certain such embodiments, an elution rate of a drug is about 0.05 µg/day to about 10 µg/day is achieved. In other embodiments an elution rate of about 0.05 µg/day to about 5 µg/day, about 0.05 µg/day to about 3 µg/day, or about 0.05 µg/day to about 2 µg/day is achieved. In other embodiment, an elution rate of about 2 µg/day to about 5 µg/day, about 4 µg/day to about 7 µg/day, or about 6 µg/day to about 10 µg/day is achieved. In other embodiments, an elution rate of about 1 µg/day to about 4 µg/day, about 3 µg/day to about 6 µg/day, or about 7 µg/day to about 10 µg/day is achieved. In still other embodiments, an elution rate of about 0.05 µg/day to about 1 µg/day, including 0.06, 0.07, 0.08, 0.09, 0.1, 0.2, 0.3, 0.4, 0.5, 0.6, 0.7, 0.8, or µg/day is achieved. It shall be appreciated that additional ranges of drugs bordering, overlapping or inclusive of the ranges listed above are also used in certain embodiments.

Alternatively, or in addition to one or more of the parameters above, the release of drug from an implant may be controlled based on the desired concentration of the drug at target tissues. In some embodiments, the desired concentration of a drug at the target tissue, ranges from about 1 nM to about 100 nM. In other embodiments the desired concentration of a drug at the site of action ranges from about 10 nM to about 90 nM, from about 20 nM to about 80 nM, from about 30 nM to about 70 nM, or from about 40 nM to about 60 nM. In still other embodiments the desired concentration of a drug at the site of action ranges from about 1 nM to about 40 nM, from about 20 nM to about 60 nM, from about 50 nM to about 70 nM, or from about 60 nM to about 90 nM. In yet other embodiments the desired concentration of a drug at the site of action ranges from about 1 nM to about 30 nM, from about 10 nM to about 50 nM, from about 30 nM to about 70 nM, or from about 60 nM to about 100 nM. In some embodiments, the desired concentration of a drug at the site of action ranges from about 45 nM to about 55 nM, including 46, 47, 48, 49, 50, 51, 52, 53, and 54 nM. It shall be appreciated that additional ranges of drugs bordering, overlapping or inclusive of the ranges listed above are also used in certain embodiments.

Drugs

The therapeutic agents utilized with the drug delivery implant, may include one or more drugs provided below, either alone or in combination. The drugs utilized may also be prodrugs of, equivalents of, derivatives of, or analogs of one or more of the drugs provided below. The drugs may include but are not limited to pharmaceutical agents including anti-glaucoma medications, ocular agents, antimicrobial agents (e.g., antibiotic, antiviral, antiparasitic, antifungal agents), anti-inflammatory agents (including steroids or non-steroidal anti-inflammatory), biological agents including hormones, enzymes or enzyme-related components, antibodies or antibody-related components, oligonucleotides (including DNA, RNA, short-interfering RNA, antisense oligonucleotides, and the like), DNA/RNA vectors, viruses (either wild type or genetically modified) or viral vectors, peptides, proteins, enzymes, extracellular matrix components, and live cells configured to produce one or more biological components. The use of any particular drug is not limited to its primary effect or regulatory body-approved treatment indication or manner of use. Drugs also include compounds or other materials that reduce or treat one or more side effects of another drug or therapeutic agent. As many drugs have more than a single mode of action, the listing of any particular drug within any one therapeutic class below is only representative of one possible use of the drug and is not intended to limit the scope of its use with the ophthalmic implant system.

As discussed above, the therapeutic agents may be combined with any number of excipients as is known in the art. In addition to the biodegradable polymeric excipients discussed above, other excipients may be used, including, but not limited to, benzyl alcohol, ethylcellulose, methylcellulose, hydroxymethylcellulose, cetyl alcohol, croscarmellose sodium, dextrans, dextrose, fructose, gelatin, glycerin, monoglycerides, diglycerides, kaolin, calcium chloride, lactose, lactose monohydrate, maltodextrins, polysorbates, pregelatinized starch, calcium stearate, magnesium stearate, silcon dioxide, cornstarch, talc, and the like. The one or more excipients may be included in total amounts as low as about 1%, 5%, or 10% and in other embodiments may be included in total amounts as high as 50%, 70% or 90%.

Examples of drugs may include various anti-secretory agents; antimitotics and other anti-proliferative agents, including among others, anti-angiogenesis agents such as angiostatin, anecortave acetate, thrombospondin, VEGF receptor tyrosine kinase inhibitors and anti-vascular endothelial growth factor (anti-VEGF) drugs such as ranibizumab (e.g., LUCENTIS®) and bevacizumab (e.g., AVASTIN®), pegaptanib (e.g., MACUGEN®), aflibercept (e.g., EYLEA®), anti-PDGF (e.g., FOVISTA®), latanosprotene bunod (e.g., VESNEO®), netasurdil AR-11324 (e.g., RHOPRESSA®)), olopatidine, sunitinib and sorafenib and any of a variety of known small-molecule and transcription inhibitors having anti-angiogenesis effect; classes of known ophthalmic drugs, including: glaucoma agents, such as adrenergic antagonists, including for example, beta-blocker agents such as atenolol propranolol, metipranolol, betaxolol, carteolol, levobetaxolol, levobunolol and timolol; adrenergic agonists or sympathomimetic agents such as epinephrine, dipivefrin, clonidine, aparclonidine, and brimonidine; parasympathomimetics or cholingeric agonists such as pilocarpine, carbachol, phospholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and unoprostone.

Other examples of drugs may also include anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluroometholone, loteprednol, medrysone, fluocinolone acetonide, triamcinolone acetonide, triamcinolone, triamcinolone acetonide, beclomethasone, budesonide, flunisolide, fluorometholone, fluticasone, hydrocortisone, hydrocortisone acetate, loteprednol, rimexolone and non-steroidal anti-inflammatory agents including, for example, diclofenac, flurbiprofen, ibuprofen, bromfenac, nepafenac, and ketorolac, salicylate, indomethacin, ibuprofen, naxopren, piroxicam and nabumetone; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin and tobramycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B and miconazole; antivirals such as idoxuridine trifluorothymidine, acyclovir, gancyclovir, interferon; antimicotics; immune-modulating agents such as antiallergenics, including, for example, sodium chromoglycate, antazoline, methapyriline, chlorpheniramine, cetrizine, pyrilamine, prophenpyridamine; anti-histamine agents such as azelastine, emedastine and levocabastine; immunological drugs (such as vaccines, immune stimulants, and/or immunosuppressants); MAST cell stabilizer agents such as cromolyn sodium, ketotifen, lodoxamide, nedocrimil, olopatadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latrunculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cylclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor or antagonists thereof (such as those disclosed in U.S. Pat. No. 7,759,472 or U.S. patent application Ser. Nos. 12/465,051, 12/564,863, or 12/641,270, each of which is incorporated in its entirety by reference herein), transforming growth factor beta, somatotrapin, fibronectin, connective tissue growth factor, bone morphogenic proteins (BMPs); cytokines such as interleukins, CD44, cochlin, and serum amyloids, such as serum amyloid A.

Other therapeutic agents may include neuroprotective agents such as lubezole, nimodipine and related compounds, and including blood flow enhancers such as dorzolamide or betaxolol; compounds that promote blood oxygenation such as erythropoeitin; sodium channels blockers; calcium channel blockers such as nilvadipine or lomerizine; glutamate inhibitors such as memantine nitromemantine, riluzole, dextromethorphan or agmatine; acetylcholinsterase inhibitors such as galantamine; hydroxylamines or derivatives thereof, such as the water soluble hydroxylamine derivative OT-440; synaptic modulators such as hydrogen sulfide compounds containing flavonoid glycosides and/or terpenoids, such as *Ginkgo biloba*; neurotrophic factors such as glial cell-line derived neutrophic factor, brain derived neurotrophic factor; cytokines of the IL-6 family of proteins such as ciliary neurotrophic factor or leukemia inhibitory factor; compounds or factors that affect nitric oxide levels, such as nitric oxide, nitroglycerin, or nitric oxide synthase inhibitors; cannabinoid receptor agonsists such as WIN55-212-2; free radical scavengers such as methoxypolyethylene glycol thioester (MPDTE) or methoxypolyethlene glycol thiol coupled with EDTA methyl triester (MPSEDE); anti-oxidants such as astaxathin, dithiolethione, vitamin E, or metallocorroles (e.g., iron, manganese or gallium corroles); compounds or factors involved in oxygen homeostasis such as neuroglobin or cytoglobin; inhibitors or factors that impact mitochondrial division or fission, such as Mdivi-1 (a selective inhibitor of dynamin related protein 1 (Drp1)); kinase inhibitors or modulators such as the Rho-kinase inhibitor H-1152 or the tyrosine kinase inhibitor AG1478; compounds or factors that affect integrin function, such as the Beta 1-integrin activating antibody HUTS-21; N-acyl-ethanaolamines and their precursors, N-acyl-ethanolamine phospholipids; stimulators of glucagon-like peptide 1 receptors (e.g., glucagon-like peptide 1); polyphenol containing compounds such as resveratrol; chelating compounds; apoptosis-related protease inhibitors; compounds that reduce new protein synthesis; radiotherapeutic agents; photodynamic therapy agents; gene therapy agents; genetic modulators; auto-immune modulators that prevent damage to nerves or portions of nerves (e.g., demyelination) such as glatimir; myelin inhibitors such as anti-NgR Blocking Protein, NgR (310)ecto-Fc; other immune modulators such as FK506 binding proteins (e.g., FKBP51); and dry eye medications such as cyclosporine, cyclosporine A, delmulcents, and sodium hyaluronate.

Other therapeutic agents that may be used include: other beta-blocker agents such as acebutolol, atenolol, bisoprolol, carvedilol, asmolol, labetalol, nadolol, penbutolol, and pindolol; other corticosteroidal and non-steroidal anti-inflammatory agents such aspirin, betamethasone, cortisone, diflunisal, etodolac, fenoprofen, fludrocortisone, flurbipro-fen, hydrocortisone, ibuprofen, indomethacine, ketoprofen, meclofenamate, mefenamic acid, meloxicam, methylprednisolone, nabumetone, naproxen, oxaprozin, prednisolone, prioxicam, salsalate, sulindac and tolmetin; COX-2 inhibitors like celecoxib, rofecoxib and. Valdecoxib; other immune-modulating agents such as aldesleukin, adalimumab (HUMIRA®), azathioprine, basiliximab, daclizumab, etanercept (ENBREL®), hydroxychloroquine, infliximab (REMICADE®), leflunomide, methotrexate, mycophenolate mofetil, and sulfasalazine; other anti-histamine agents such as loratadine, desloratadine, cetirizine, diphenhydramine, chlorpheniramine, dexchlorpheniramine, clemastine, cyproheptadine, fexofenadine, hydroxyzine and promethazine; other anti-infective agents such as aminoglycosides such as amikacin and streptomycin; anti-fungal agents such as amphotericin B, caspofungin, clotrimazole, fluconazole, itraconazole, ketoconazole, voriconazole, terbinafine and nystatin; anti-malarial agents such as chloroquine, atovaquone, mefloquine, primaquine, quinidine and quinine; anti-mycobacterium agents such as ethambutol, isoniazid, pyrazinamide, rifampin and rifabutin; anti-parasitic agents such asalbendazole, mebendazole, thiobendazole, metronidazole, pyrantel, atovaquone, iodoquinaol, ivermectin, paromycin, praziquantel, and trimatrexate; other anti-viral agents, including anti-CMV or anti-herpetic agents such as acyclovir, cidofovir, famciclovir, gangciclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddl, 3TC, d4T, ddC, tenofovir and emtricitabine, delavirdine, efavirenz and nevirapine; other anti-viral agents such as interferons, ribavirin and trifluridiene; other anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; other antibacterials such as aztreonam, chloramphenicol, clindamycin, linezolid, nitrofurantoin and vancomycin; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprusside, phenoxybenzamine, epoprostenol, tolazoline, treprostinil and nitrate-based agents; anti-coagulant agents, including heparins and heparinoids such as heparin, dalteparin, enoxaparin, tinzaparin and fondaparinux; other anti-coagulant agents such as hirudin, aprotinin, argatroban, bivalirudin, desirudin, lepirudin, warfarin and ximelagatran; anti-platelet agents such as abciximab, clopidogrel, dipyridamole, optifibatide, ticlopidine and tirofiban; prostaglandin PDE-5 inhibitors and other prostaglandin agents such as alprostadil, carboprost, sildenafil, tadalafil and vardenafil; thrombin inhibitors; antithrombogenic agents; anti-platelet aggregating agents; thrombolytic agents and/or fibrinolytic agents such as alteplase, anistreplase, reteplase, streptokinase, tenecteplase and urokinase; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxy-progesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-fluorouracil (5-FU); immune modulating agents such as aldesleukin, imatinib, rituximab and tositumomab; mitotic inhibitors docetaxel, etoposide, vinblastine and vincristine; radioactive agents such as strontium-89; and other anti-neoplastic agents such as irinotecan, topotecan and mitotane.

The drugs carried by the drug delivery implant may be in any form that can be reasonably retained within the device and results in controlled elution of the resident drug or drugs over a period of time lasting up to several years. Certain embodiments utilize drugs that are readily soluble in ocular fluid, while other embodiments utilize drugs that are partially or scantily soluble in ocular fluid. It should be re-emphasized that "drug" as used herein includes active drugs, prodrugs and salts thereof, and drugs that are otherwise modified for purposes of storage, transmissibility through membranes, stability, and the like. The drug stored in a device may include excipients, stabilizers, agents that modify elution or dissolution rates, and any other materials or agents that assist in the stability and desired elution of the drug over time.

For example, the therapeutic agent may be in any form, including but not limited to a compressed pellet, a solid, a capsule, multiple particles, a liquid, an oil, a gel, a suspension, slurry, emulsion, and the like. In certain embodiments, drug particles are in the form of micro-pellets (e.g., micro-tablets), fine powders, or slurries, each of which has fluid-like properties, allowing for recharging by injection into the inner lumen(s) in the same manner as a liquid or oil. In some embodiments, the loading and/or recharging of a device is accomplished with a syringe/needle, through which the therapeutic agent is delivered. In some embodiments, they are delivered through a needle of about 23 gauge to about 32 gauge, including 23-25 gauge, 25 to 27 gauge, 27-29 gauge, 29-30 gauge, 30-32 gauge, and overlapping ranges thereof. In some embodiments, the needle is 23, 24, 25, 26, 27, 28, 29, 30, 31, or 32 gauge.

When more than one drug is desired for treatment of a particular pathology or when a second drug is administered such as to counteract a side effect of the first drug, some embodiments may utilize two agents of the same form. In other embodiments, agents in different form may be used. Likewise, should one or more drugs utilize an adjuvant, excipient, or auxiliary compound, for example to enhance stability or tailor the elution profile, that compound or compounds may also be in any form that is compatible with the drug and can be reasonably retained with the implant.

In some embodiments, treatment of particular pathology with a drug released from the implant may not only treat the pathology, but also induce certain undesirable side effects. In some cases, delivery of certain drugs may treat a pathological condition, but indirectly increase intraocular pressure. Steroids, for example, may have such an effect. In certain embodiments, a drug delivery implant that delivers a steroid to an ocular target tissue may induce an undesirable increase in intraocular pressure. In such embodiments, the drug delivery implant may include a shunt feature which reduces the undesirable increased intraocular pressure by transporting excess aqueous humor from the anterior chamber. Thus, in some embodiments, implants functioning both as drug delivery devices and shunts can serve to deliver a therapeutic agent, and simultaneously drain away accumulated fluid, thereby alleviating the side effect of the drug.

It will be understood that embodiments as described herein may include a drug mixed or compounded with a biodegradable material, excipient, or other agent modifying the release characteristics of the drug. Preferred biodegradable materials include those noted above, including copolymers of lactic acid and glycolic acid, also known as poly (lactic-co-glycolic acid) or PLGA. It will be understood by one skilled in the art that although some disclosure herein specifically describes use of PLGA, other suitable biodegradable materials may be substituted for PLGA or used in combination with PLGA in such embodiments. It will also be understood that in certain embodiments as described herein, the drug positioned within the lumen of the implant is not compounded or mixed with any other compound or material, thereby maximizing the volume of drug that is positioned within the lumen.

It may be desirable, in some embodiments, to provide for a particular rate of release of drug from a PLGA copolymer or other polymeric material. As the release rate of a drug from a polymer correlates with the degradation rate of that polymer, control of the degradation rate provides a means for control of the delivery rate of the drug. Variation of the average molecular weight of the polymer or copolymer chains which make up the PLGA copolymer or other polymer may be used to control the degradation rate of the copolymer, thereby achieving a desired duration or other release profile of therapeutic agent delivery to the eye. In certain other embodiments employing copolymers, rate of biodegradation of the copolymer may be controlled by varying the ratio of the monomers or oligomers in the copolymer. Still other embodiments may utilize combinations of varying the average molecular weights of the constituents of the copolymer and varying the constitution of the copolymer to achieve a desired biodegradation rate.

EXAMPLES

In many configurations of the bioresorbable implants disclosed herein, the protein drug concentration within the device will diminish over time during use. Because the elution rate is proportional to the concentration gradient between the inside and outside of the device, the elution rate will also decline over time. To accommodate such events, in several embodiments, the elution features and the initial protein drug concentration are selected such that a therapeutic elution rate will still be delivered at an extended time period (e.g., 3, 6, 9 months or longer).

Figure 21A:
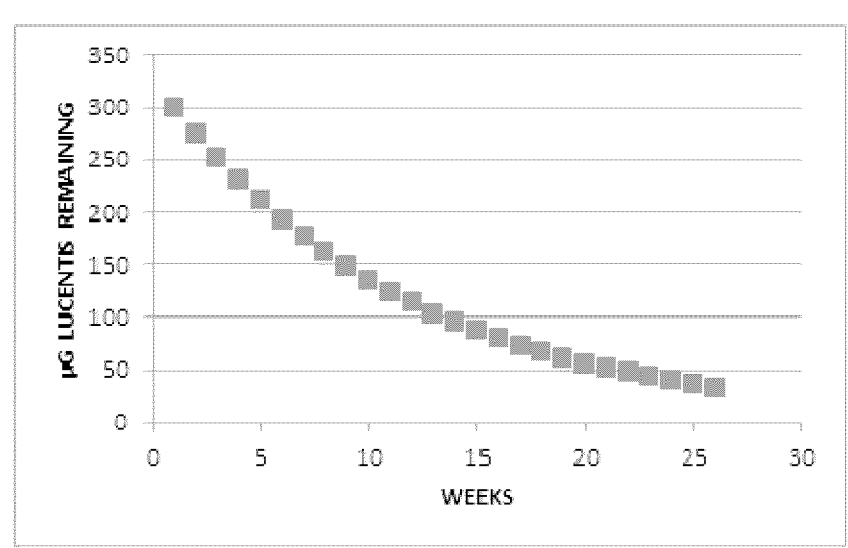
FIGS. 21A-21B depict drug concentration and elution data according to several embodiments herein.
Figure 21B:
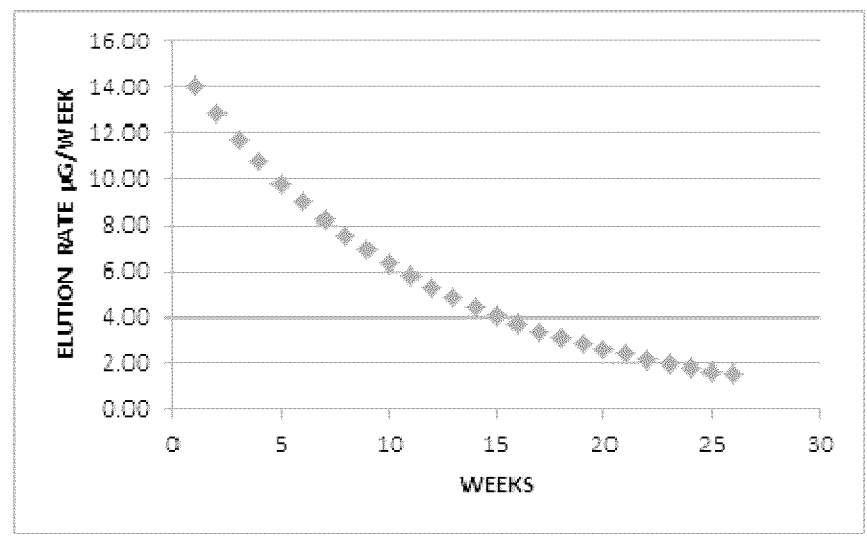

FIGS. 21A and 21B depict prophetic elution data related to elution from an implant according to several embodiments wherein the initial protein concentration inside the device is 300 mg/mL, the initial payload of protein is 300 micrograms, the total elution feature area and the wall thickness are dimensioned such that the initial elution rate through the elution features is 14 micrograms/week, and the dimensions of the elution features are fixed. In this hypothetical case, the concentration of drug protein within the device declines about nine-fold over six months (FIG. 21A) as drug elutes out through the elution features and the rate also decreases over time (FIG. 21B).

The rate of erosion may be determined by selecting the chemical structure of the bioresorbable material. Bioresorbable materials can be determined to be absorbable over days, weeks, or months. Chemical linkages within bioresorbable materials may be water-degradable (polymers, copolymers, and oligomers of glycolide, dl-lactide, 1-lactide, dioxanone, esters, carbonates, and trimethylene carbondate); or enzyme-degradable (such as peptides, amides, and polyetheramides); or poly(hydroxyacid)s, poly(orthocarbonate)s, poly(anydrides)s, poly(lactone)s, poly(aminoacid)s, poly(carbonate)s, and poly(phosphonate)s, or combinations of any of the above.

Figure 22A:
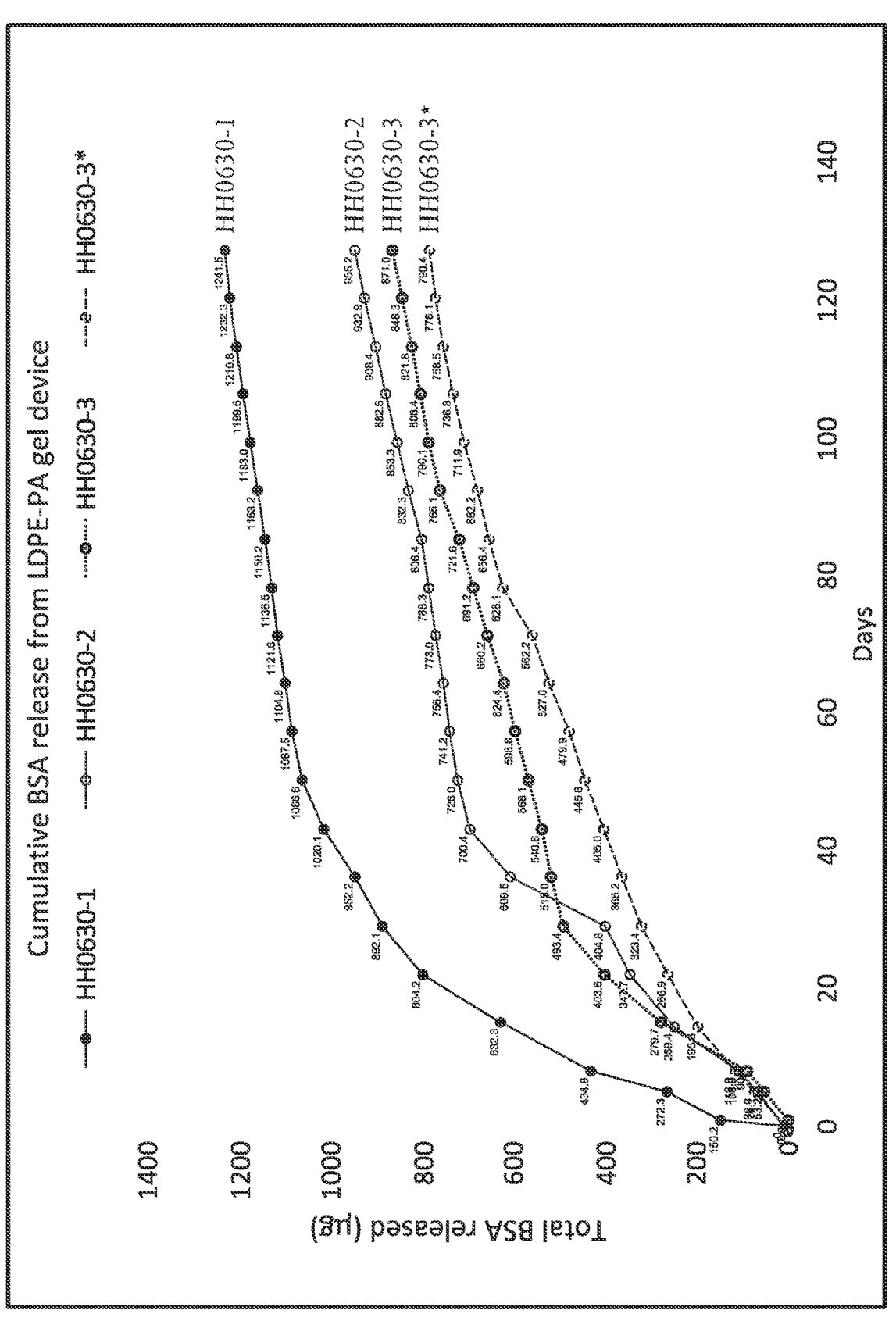
FIGS. 22A-22B depict drug elution data according to several embodiments herein.
Figure 22B:
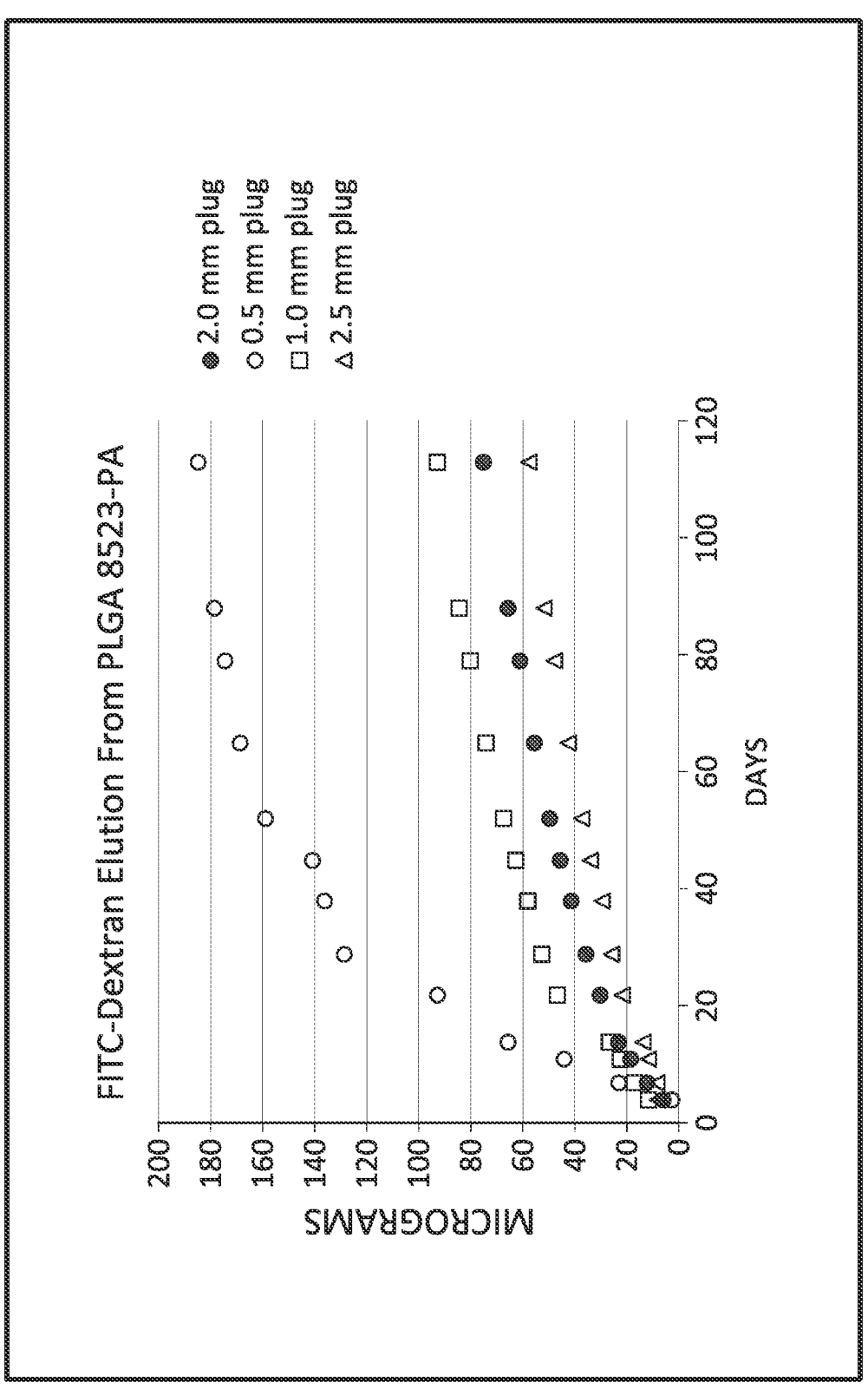

FIGS. 22A-22B depict drug elution data according to several embodiments herein. FIG. 21A depicts change in drug elution rate over time from an implant wherein tubes were approximately 1 inch long segments of LDPE, 0.040 inch (1 mm) ID, a hydrogel plug was polymerized form 5% acrylamide and 0.14% methylene bisacrylamide, lengths of the hydrogel plugs were trimmed to approximately 1-3 mm, the protein solution was bovine serum albumin (e.g., a surrogate for ranibizumab) initially at 150 mg/ml, and approximately 1 cm of each tube was filled with the BSA solution having a payload of approximately 1200 micrograms.

FIG. 22B depicts change in drug elution rate over time from an implant, wherein tubes were approximately 1 inch long segments of 350×500 micron PLG 8523, the hydrogel plug was polymerized from 7.5% acrylamide and 0.21% methylene bisacrylamide, lengths of the hydrogel plugs were trimmed to approximately 1-3 mm, the protein solution was 40 kD FITC-dextran (e.g., a surrogate for ranibizumab) initially at 200 mg/ml, and approximately 1.5 cm of each tube was filled with the FITC-dextran solution having a payload of approximately 300 micrograms.

While certain embodiments of the disclosure have been described, these embodiments have been presented by way of example only, and are not intended to limit the scope of the disclosure. Indeed, the novel methods, systems, and devices described herein may be embodied in a variety of other forms. For example, embodiments of one illustrated or described implant may be combined with embodiments of another illustrated or described shunt. Moreover, the implants described above may be utilized for other purposes. For example, the implants may be used to drain fluid from the anterior chamber to other locations of the eye or outside the eye. Furthermore, various omissions, substitutions and changes in the form of the methods, systems, and devices described herein may be made without departing from the spirit of the disclosure.

One or more of the features illustrated in the drawings and/or described herein may be rearranged and/or combined into a single component or embodied in several components. Additional components may also be added. While certain example embodiments have been described and shown in the accompanying drawings, it is to be understood that such embodiments are merely illustrative and not restrictive. Thus, the inventions are not limited to the specific constructions and arrangements shown and described, since various other modifications may occur to those ordinarily skilled in the art based on the present disclosure.

Various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Method step and/or actions disclosed herein can be performed in conjunction with each other, and steps and/or actions can be further divided into additional steps and/or actions.

It is to be understood that the claims are not limited to the precise configuration and components illustrated above. Various modifications, changes and variations may be made in the arrangement, operation and details of the methods and apparatus described above.

What is claimed is:

1. An ocular implant configured for implantation into an eye of a subject comprising:
   an elongate outer shell comprising a bioerodible material and shaped to define an interior lumen, the elongate outer shell comprising a proximal end and a distal end, the proximal end and the distal end each being rounded, wherein the interior lumen is a continuous interior lumen extending from the proximal end to the distal end,
   an internal plug positioned within the interior lumen;
   a drug positioned within the interior lumen, the drug at least partially dispersed or mixed within the internal plug creating an internal plug and drug mixture; and
   one or more orifices at or near the distal end of the elongate outer shell and one or more orifices at or near the proximal end of the elongate outer shell, wherein the drug is configured to pass through the internal plug to control elution of the drug,
   wherein the ocular implant is configured to be positioned within the vitreous cavity, and
   wherein the ocular implant is configured to elute the drug from the one or more orifices at or near the distal end and the one or more orifices at or near the proximal end.

2. The ocular implant of claim 1, wherein the internal plug is positioned adjacent a distal-most end of the interior lumen.

3. The ocular implant of claim 1, further comprising a coating surrounding at least a portion of the elongate outer shell.

4. The ocular implant of claim 1, wherein the proximal end comprises a cap.

5. The ocular implant of claim 1, wherein the elongate outer shell is configured to begin to bioerode after all or substantially all of the drug is eluted from the interior lumen of the ocular implant.

6. The ocular implant of claim 1, wherein the elongate outer shell is configured to begin to bioerode while at least a portion of the drug to be eluted from the interior lumen of the ocular implant remains in the interior lumen.

7. The ocular implant of claim 1, wherein the ocular implant is positioned inside a lumen of a 23-25 Gauge needle or cannula of a delivery device.

8. The ocular implant of claim 1, wherein the ocular implant is capsule-shaped.

9. The ocular implant of claim 1, wherein the drug is completely dispersed or mixed within the internal plug to create the internal plug and drug mixture.

10. The ocular implant of claim 9, wherein the internal plug and drug mixture fills the entire interior lumen.

11. The ocular implant of claim 1, wherein the drug comprises at least fifty percent of the internal plug and drug mixture.

12. The ocular implant of claim 1, wherein the internal plug and drug mixture is pre-formed.

13. The ocular implant of claim 1, wherein the distal end comprises more orifices than the proximal end.

14. The ocular implant of claim 1, wherein the continuous interior lumen allows for elution of the same drug from the same internal plug and drug mixture through the one or more orifices at or near the distal end and the one or more orifices at or near the proximal end.

15. The ocular implant of claim 1, wherein one or more orifices are positioned at the proximal end of the elongate outer shell.

16. The ocular implant of claim 1, wherein the interior lumen is unobstructed between the proximal end and the distal end thereby allowing elution of the drug through the one or more orifices at or near the distal end and the one or more orifices at or near the proximal end.

17. The ocular implant of claim 1, wherein the internal plug and drug mixture fills the entire lumen and wherein one or more orifices are positioned at the proximal end of the elongate outer shell.

\* \* \* \* \*